US012658311B2

(12) United States Patent
Wolf et al.

(10) Patent No.: US 12,658,311 B2
(45) Date of Patent: Jun. 16, 2026

(54) ANALYZING SURGICAL VIDEOS TO DETERMINE COMPLIANCE WITH SELECTED SURGICAL GUIDELINES

(71) Applicant: Theator Inc., Palo Alto, CA (US)

(72) Inventors: Tamir Wolf, Palo Alto, CA (US); Dotan Asselmann, Holon (IL)

(73) Assignee: Theator Inc., Palo Alto, CA (US)

( * ) Notice: Subject to any disclaimer, the term of this patent is extended or adjusted under 35 U.S.C. 154(b) by 345 days.

(21) Appl. No.: 18/196,329

(22) Filed: May 11, 2023

(65) Prior Publication Data

US 2023/0386680 A1 Nov. 30, 2023

Related U.S. Application Data

(60) Provisional application No. 63/411,758, filed on Sep. 30, 2022, provisional application No. 63/399,698, (Continued)

(51) Int. Cl.
G16H 40/20 (2018.01)
G06F 40/20 (2020.01)
(Continued)

(52) U.S. Cl.
CPC ............. G16H 40/20 (2018.01); G06Q 10/10 (2013.01); G06Q 30/018 (2013.01); (Continued)

(58) Field of Classification Search
CPC ........ G16H 70/20; G16H 40/20; G16H 10/60; G16H 15/00; G16H 30/40; G16H 40/67;

A61B 34/25; A61B 2034/252; G06F 16/71; G06F 16/735; G06F 3/048; G06F 3/0482; G06F 16/783; G06F 16/7837; G06F 16/7847; G06F 16/41; G06F 16/743;
(Continued)

(56) References Cited

U.S. PATENT DOCUMENTS 5,791,907 A 8/1998 Ramshaw et al.
8,886,577 B2 11/2014 Mangione-Smith
(Continued)

FOREIGN PATENT DOCUMENTS

CA 2575759 A1 2/2006
CA 3049148 A1 8/2018
(Continued)

OTHER PUBLICATIONS

Loukas, C. Video content analysis of surgical procedures. Surg Endosc 32, 553-568 (2018) . https://doi.org/10.1007/s00464-017-5878-1 (Year: 2018).
(Continued)

*Primary Examiner* — Sumati Lefkowitz
*Assistant Examiner* — Ryan P Potts
(74) *Attorney, Agent, or Firm* — Sterne, Kessler, Goldstein & Fox P.L.L.C.

(57) ABSTRACT

An apparatus, system, method, and computer-readable medium include aspects for using surgical video analysis. The aspects utilize intracorporeal video footage, image analysis, and notifications to optimize correspondences among medical procedure information, medical guidelines, and medical transaction information.

21 Claims, 19 Drawing Sheets

Related U.S. Application Data filed on Aug. 21, 2022, provisional application No. 63/389,130, filed on Jul. 14, 2022, provisional application No. 63/346,987, filed on May 30, 2022.

(51) Int. Cl.

| | |
|---|---|
| *G06Q 10/10* | (2023.01) |
| *G06Q 30/018* | (2023.01) |
| *G06Q 40/08* | (2012.01) |
| *G06T 7/00* | (2017.01) |
| *G06V 10/70* | (2022.01) |
| *G06V 10/774* | (2022.01) |
| *G06V 20/40* | (2022.01) |
| *G06V 20/52* | (2022.01) |
| *G16H 10/60* | (2018.01) |
| *G16H 15/00* | (2018.01) |
| *G16H 30/40* | (2018.01) |
| *G16H 40/67* | (2018.01) |
| *G16H 70/20* | (2018.01) |

(52) U.S. Cl.
CPC ............ *G06T 7/0012* (2013.01); *G06V 20/41* (2022.01); *G06V 20/44* (2022.01); *G06V 20/46* (2022.01); *G06V 20/52* (2022.01); *G16H 10/60* (2018.01); *G16H 15/00* (2018.01); *G16H 30/40* (2018.01); *G16H 40/67* (2018.01); *G16H 70/20* (2018.01); *G06F 40/20* (2020.01); *G06Q 40/08* (2013.01); *G06T 2207/10016* (2013.01); *G06V 10/70* (2022.01); *G06V 10/774* (2022.01); *G06V 2201/03* (2022.01); *G06V 2201/034* (2022.01)

(58) Field of Classification Search
CPC ........ G06F 40/20; G06Q 40/08; G06Q 10/10; G06Q 30/018; G06V 20/49; G06V 20/41; G06V 20/44; G06V 20/46; G06V 2201/03; G06V 10/70; G06V 20/52; G06V 20/40; G06V 10/82; G06V 10/74; G06V 10/761; G06V 20/48; G06V 10/84; G06V 10/77; G06V 10/766; G06V 10/764; G06V 10/762; G06V 10/768; G06V 10/86; G06V 10/87; G06V 10/75; G06V 10/774; G06V 2201/034; G06T 7/0012; G06T 2207/10016
See application file for complete search history.

(56) References Cited

U.S. PATENT DOCUMENTS

| | | | | |
|---|---|---|---|---|
| 9,788,907 | B1 | 10/2017 | Alvi et al. | |
| 9,836,654 | B1 * | 12/2017 | Alvi | G11B 27/34 |
| 9,877,633 | B2 | 1/2018 | Zhao et al. | |
| 10,058,393 | B2 | 8/2018 | Bonutti et al. | |
| 10,387,720 | B2 | 8/2019 | Johnson et al. | |
| 10,646,156 | B1 | 5/2020 | Schnorr | |
| 10,729,502 | B1 * | 8/2020 | Wolf | G16H 50/70 |
| 10,791,301 | B1 | 9/2020 | Garcia Kilroy et al. | |
| 2004/0062381 | A1 | 4/2004 | Shambaugh et al. | |
| 2004/0078236 | A1 | 4/2004 | Stoodley et al. | |
| 2004/0125121 | A1 | 7/2004 | Pea et al. | |
| 2005/0149361 | A1 | 7/2005 | Saus et al. | |
| 2006/0053249 | A1 | 3/2006 | Yamaki et al. | |
| 2006/0143060 | A1 | 6/2006 | Conry et al. | |
| 2006/0159325 | A1 | 7/2006 | Zeineh et al. | |
| 2007/0156344 | A1 | 7/2007 | Sender et al. | |
| 2007/0238981 | A1 | 10/2007 | Zhu et al. | |
| 2008/0243064 | A1 | 10/2008 | Stahler et al. | |
| 2009/0192823 | A1 | 7/2009 | Hawkins et al. | |
| 2009/0300507 | A1 | 12/2009 | Raghavan et al. | |
| 2010/0001149 | A1 | 1/2010 | Song et al. | |
| 2010/0036676 | A1 | 2/2010 | Safdi et al. | |
| 2010/0097398 | A1 | 4/2010 | Tsurumi | |
| 2010/0134609 | A1 | 6/2010 | Johnson | |
| 2011/0046476 | A1 | 2/2011 | Cinquin et al. | |
| 2011/0090367 | A1 | 4/2011 | White et al. | |
| 2011/0225000 | A1 | 9/2011 | Selim | |
| 2011/0264528 | A1 | 10/2011 | Whale | |
| 2011/0276340 | A1 | 11/2011 | DeBoer et al. | |
| 2011/0276348 | A1 | 11/2011 | Ahn et al. | |
| 2011/0306985 | A1 | 12/2011 | Inoue et al. | |
| 2012/0035963 | A1 | 2/2012 | Qian et al. | |
| 2012/0177256 | A1 | 7/2012 | Keefe et al. | |
| 2012/0179061 | A1 | 7/2012 | Ramanan et al. | |
| 2013/0132117 | A1 | 5/2013 | Barsoum et al. | |
| 2013/0297343 | A1 | 11/2013 | Hirose et al. | |
| 2014/0031659 | A1 | 1/2014 | Zhao et al. | |
| 2014/0081659 | A1 | 3/2014 | Nawana et al. | |
| 2014/0101550 | A1 | 4/2014 | Zises | |
| 2014/0220527 | A1 | 8/2014 | Li et al. | |
| 2014/0226888 | A1 | 8/2014 | Skidmore | |
| 2014/0270711 | A1 | 9/2014 | Maser et al. | |
| 2014/0276940 | A1 | 9/2014 | Seo | |
| 2014/0286533 | A1 | 9/2014 | Luo et al. | |
| 2014/0297301 | A1 | 10/2014 | Rock | |
| 2015/0046182 | A1 | 2/2015 | Kinney et al. | |
| 2015/0119705 | A1 | 4/2015 | Tochterman et al. | |
| 2015/0190208 | A1 | 7/2015 | Silveira | |
| 2016/0004911 | A1 | 1/2016 | Cheng et al. | |
| 2016/0067007 | A1 | 3/2016 | Piron et al. | |
| 2016/0191887 | A1 | 6/2016 | Casas | |
| 2016/0239617 | A1 | 8/2016 | Farooq et al. | |
| 2016/0253472 | A1 | 9/2016 | Pedersen et al. | |
| 2016/0259888 | A1 | 9/2016 | Liu et al. | |
| 2017/0046835 | A1 | 2/2017 | Tajbakhsh et al. | |
| 2017/0053543 | A1 * | 2/2017 | Agrawal | A61B 90/37 |
| 2017/0071679 | A1 | 3/2017 | Weir et al. | |
| 2017/0112577 | A1 | 4/2017 | Bonutti et al. | |
| 2017/0119258 | A1 | 5/2017 | Kotanko et al. | |
| 2017/0132785 | A1 * | 5/2017 | Wshah | G06N 3/082 |
| 2017/0177806 | A1 | 6/2017 | Fabian | |
| 2017/0249432 | A1 | 8/2017 | Grantcharov | |
| 2017/0300651 | A1 | 10/2017 | Strobridge | |
| 2017/0312031 | A1 | 11/2017 | Amanatullah et al. | |
| 2018/0065248 | A1 | 3/2018 | Barral et al. | |
| 2018/0078195 | A1 | 3/2018 | Sutaria et al. | |
| 2018/0110398 | A1 | 4/2018 | Schwartz et al. | |
| 2018/0122506 | A1 | 5/2018 | Grantcharov et al. | |
| 2018/0158361 | A1 | 6/2018 | Goll et al. | |
| 2018/0174311 | A1 | 6/2018 | Kluckner et al. | |
| 2018/0174616 | A1 | 6/2018 | Aguilar et al. | |
| 2018/0197624 | A1 | 7/2018 | Robaina et al. | |
| 2018/0247024 | A1 | 8/2018 | Divine et al. | |
| 2018/0247128 | A1 * | 8/2018 | Alvi | G16H 30/20 |
| 2018/0247560 | A1 | 8/2018 | Mackenzie et al. | |
| 2018/0303552 | A1 | 10/2018 | Ryan et al. | |
| 2018/0322949 | A1 | 11/2018 | Mohr et al. | |
| 2018/0350144 | A1 | 12/2018 | Rathod | |
| 2018/0366231 | A1 | 12/2018 | Wolf et al. | |
| 2018/0368930 | A1 | 12/2018 | Esterberg et al. | |
| 2019/0005848 | A1 | 1/2019 | Garcia Kilroy et al. | |
| 2019/0006047 | A1 | 1/2019 | Gorek et al. | |
| 2019/0060893 | A1 | 2/2019 | Evans et al. | |
| 2019/0122330 | A1 | 4/2019 | Saget et al. | |
| 2019/0125361 | A1 | 5/2019 | Shelton, IV et al. | |
| 2019/0201136 | A1 | 7/2019 | Shelton, IV et al. | |
| 2019/0201141 | A1 | 7/2019 | Shelton, IV et al. | |
| 2019/0206565 | A1 | 7/2019 | Shelton, IV | |
| 2019/0223961 | A1 | 7/2019 | Barral et al. | |
| 2019/0272917 | A1 | 9/2019 | Couture et al. | |
| 2019/0279765 | A1 | 9/2019 | Giataganas et al. | |
| 2019/0286652 | A1 | 9/2019 | Habbecke et al. | |
| 2019/0340963 | A1 | 11/2019 | Kishima et al. | |
| 2019/0347557 | A1 | 11/2019 | Khan | |
| 2019/0362834 | A1 | 11/2019 | Venkataraman et al. | |
| 2019/0362859 | A1 | 11/2019 | Bhat | |
| 2019/0365252 | A1 | 12/2019 | Fernald et al. | |
| 2019/0371456 | A1 | 12/2019 | Page et al. | |
| 2019/0380792 | A1 | 12/2019 | Poltaretskyi et al. | |

(56) References Cited

U.S. PATENT DOCUMENTS

| | | | |
|---|---|---|---|
| 2020/0030044 A1 | 1/2020 | Wang et al. | |
| 2020/0082934 A1 | 3/2020 | Venkataraman | |
| 2020/0168334 A1 | 5/2020 | Mowery | |
| 2020/0194111 A1 | 6/2020 | Venkataraman et al. | |
| 2020/0211720 A1 | 7/2020 | Goldberg | |
| 2020/0226751 A1 | 7/2020 | Jin et al. | |
| 2020/0237452 A1 | 7/2020 | Wolf et al. | |
| 2020/0258616 A1 | 8/2020 | Likosky et al. | |
| 2020/0268457 A1 | 8/2020 | Wolf et al. | |
| 2020/0268469 A1 | 8/2020 | Wolf et al. | |
| 2020/0268472 A1 | 8/2020 | Wolf et al. | |
| 2020/0273548 A1 | 8/2020 | Wolf et al. | |
| 2020/0273552 A1* | 8/2020 | Wolf | G06V 20/20 |
| 2020/0273557 A1* | 8/2020 | Wolf | G06V 20/41 |
| 2020/0273560 A1* | 8/2020 | Wolf | G06V 20/40 |
| 2020/0273561 A1 | 8/2020 | Wolf et al. | |
| 2020/0273575 A1 | 8/2020 | Wolf et al. | |
| 2020/0273581 A1 | 8/2020 | Wolf et al. | |
| 2020/0337648 A1 | 10/2020 | Saripalli et al. | |
| 2020/0367974 A1* | 11/2020 | Khalid | G06N 3/045 |
| 2021/0006752 A1 | 1/2021 | Kilroy et al. | |
| 2021/0012868 A1 | 1/2021 | Wolf et al. | |
| 2021/0015560 A1 | 1/2021 | Boddington et al. | |
| 2021/0043308 A1 | 2/2021 | Sugie et al. | |
| 2021/0158845 A1 | 5/2021 | Sethi et al. | |
| 2021/0290046 A1 | 9/2021 | Nazareth et al. | |
| 2021/0298869 A1 | 9/2021 | Wolf et al. | |
| 2021/0307840 A1 | 10/2021 | Wolf et al. | |
| 2021/0307864 A1 | 10/2021 | Wolf et al. | |
| 2021/0313052 A1 | 10/2021 | Makrinich et al. | |
| 2022/0165403 A1 | 5/2022 | Asselmann et al. | |
| 2022/0301674 A1 | 9/2022 | Wolf et al. | |

FOREIGN PATENT DOCUMENTS

| | | | |
|---|---|---|---|
| WO | 2015066565 A1 | 5/2015 | |
| WO | 2017031175 A1 | 2/2017 | |
| WO | 2018089816 A2 | 5/2018 | |
| WO | 2019040705 A1 | 2/2019 | |
| WO | 2019139478 A1 | 7/2019 | |
| WO | 2019226182 A1 | 11/2019 | |

OTHER PUBLICATIONS

Hall, Dr. Jena Mae, "Enhancing surgical education using video playback: A case study on the influence of video playback on the nature and experience of feedback between supervising surgeons and surgical residents", Queen's University, Kingston, Ontario, Canada, Sep. 2018, 162 pages. (Year: 2018).

Twinanda et al., RSDNet: Learning to Predict Remaining Surgery Duration from Laparoscopic Videos Without Manual Annotations, 38(4) IEEE Trans Med Imaging 1069-1078 (Oct. 25, 2018) (Year: 2018).

Bhatia et al., Real-Time Identification of Operating Room State from Video, Conference: Proceedings of the Twenty-Second AAAI Conference on Artificial Intelligence 1761-1766 (Jul. 2007) (Year: 2007).

"Video Analysis: An Approach for Use in Health Care"; Mackenzie et al.; Handbook of Human Factors and Ergonomics in Health Care and Patient Safety; Aug. 3, 2011 (Year: 2011).

Handbook of Human Factors Cover Pages (with copyright date) (Year: 2011).

Bernd Munzer et al. (2017). "EndoXplore: A Web-Based Video Explorer for Endoscopic Videos". 2017 IEEE International Symposium on Multimedia (ISM), p. 366-367. (Year: 2017).

Niitsu H, Hirabayashi N, Yoshinnitsu M, et al. Using the Objective Structured Assessment of Technical Skills (OSATS) global rating scale to evaluate the skills of surgical trainees in the operating room. Surg Today. 2013;43(3):271-275. doi:10.1007/s00595-012-0313-7 (Year: 2013).

A. Jin et al., "Tool Detection and Operative Skill Assessment in Surgical Videos Using Region-Based Convolutional Neural Networks," 2018 IEEE Winter Conference on Applications of Computer Vision (WACV), 2018, pp. 691-699, doi: 10.1109/VVACV .2018.00081. (Year: 2018).

Hassan, A., Ghafoor, M., Tariq, S.A. et al. High Efficiency Video Coding (HEVC)-Based Surgical Telennentoring System Using Shallow Convolutional Neural Network. J Digit Imaging 32, 1027-1043 (2019). https://doi.org/10.1007/s10278-019-00206-2 (Year: 2019).

Notification of Transmittal of the International Search Report and the Written Opinion of the International Searching Authority for International Application No. PCT/US2023/021921 mailed Oct. 16, 2023, 22 pages.

* cited by examiner

500

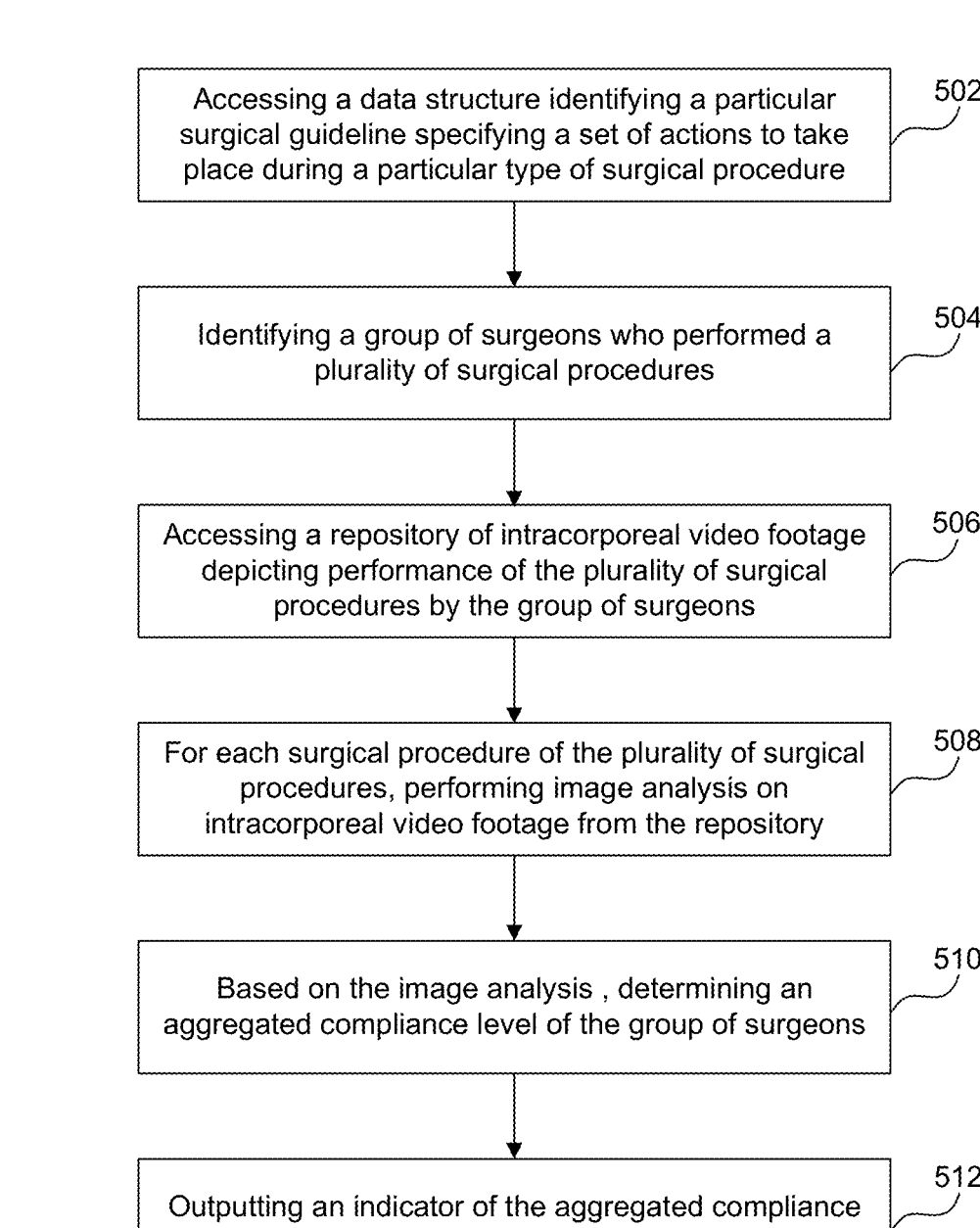

Accessing a data structure identifying a particular surgical guideline specifying a set of actions to take place during a particular type of surgical procedure — 502

Identifying a group of surgeons who performed a plurality of surgical procedures — 504

Accessing a repository of intracorporeal video footage depicting performance of the plurality of surgical procedures by the group of surgeons — 506

For each surgical procedure of the plurality of surgical procedures, performing image analysis on intracorporeal video footage from the repository — 508

Based on the image analysis , determining an aggregated compliance level of the group of surgeons — 510

Outputting an indicator of the aggregated compliance level — 512

FIG. 5

| Action 1 | Use of critical view of safety (CVS) technique |
|---|---|
| Action 2 | If the CVS is not achievable during a difficult LC, perform a bailout procedure, such as subtotal cholecystectomy |
| Action 3 | Use of intraoperative cholangiography |
| • • • | • • • |

804 Action 3

802 Action 1

Intracorporeal video stream 800

824 Action 3

822 Action 2

Intracorporeal video stream 820

842 Action 1

Intracorporeal video stream 840

900

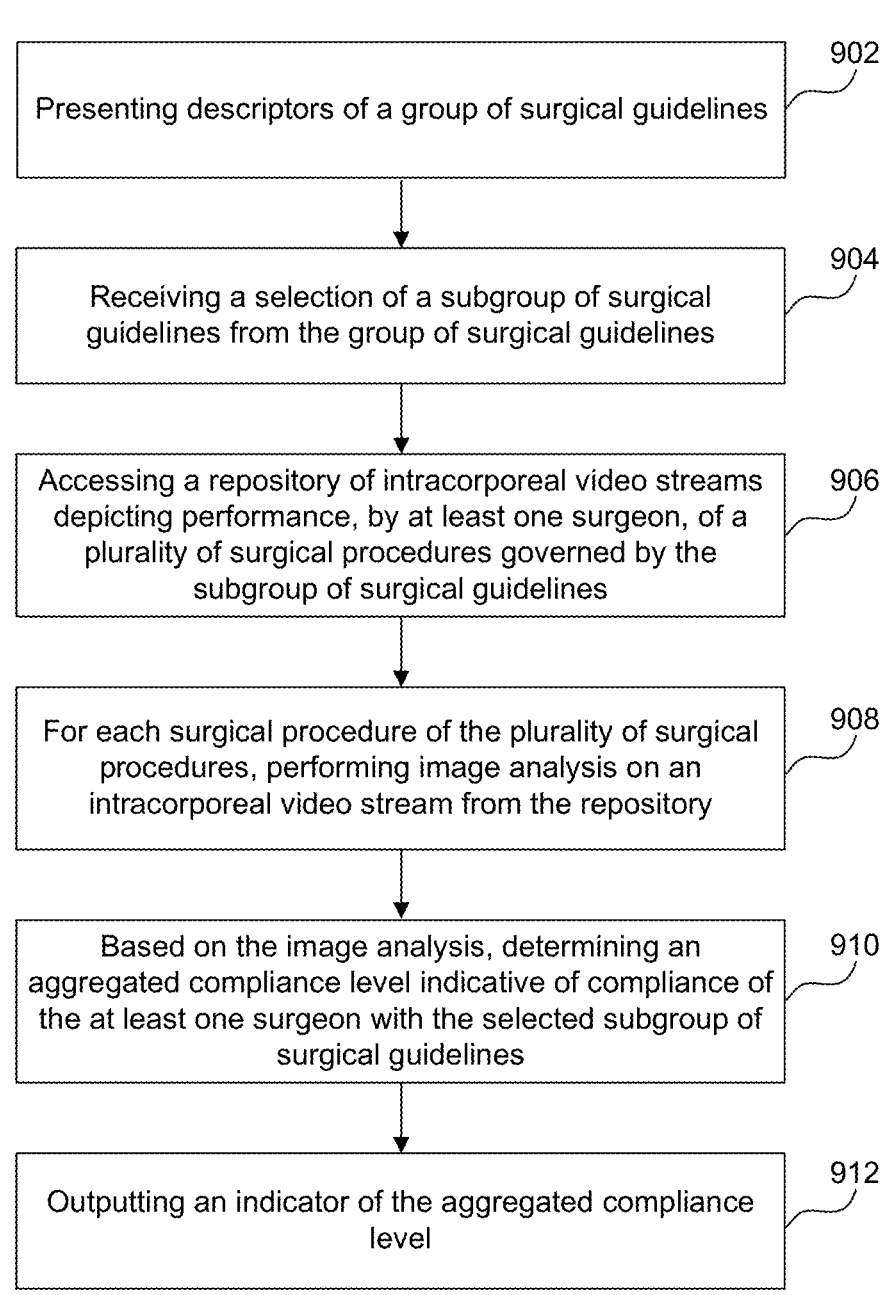

902

Presenting descriptors of a group of surgical guidelines

904

Receiving a selection of a subgroup of surgical guidelines from the group of surgical guidelines

906

Accessing a repository of intracorporeal video streams depicting performance, by at least one surgeon, of a plurality of surgical procedures governed by the subgroup of surgical guidelines

908

For each surgical procedure of the plurality of surgical procedures, performing image analysis on an intracorporeal video stream from the repository

910

Based on the image analysis, determining an aggregated compliance level indicative of compliance of the at least one surgeon with the selected subgroup of surgical guidelines

912

Outputting an indicator of the aggregated compliance level

FIG. 9

| Time | Guideline | Reduce risk of infection? |
|---|---|---|
| Preoperative | Preoperative antibiotics in high-risk patients | x |
| Surgical events | Use of critical view of safety (CVS) technique | x |
| | If the CVS is not achievable during a difficult LC, a bailout procedure, such as subtotal cholecystectomy | |
| | Clipping bile duct | x |
| | Use of intraoperative cholangiography | |
| Postoperative | Control of postoperative pain, nausea, and vomiting | |

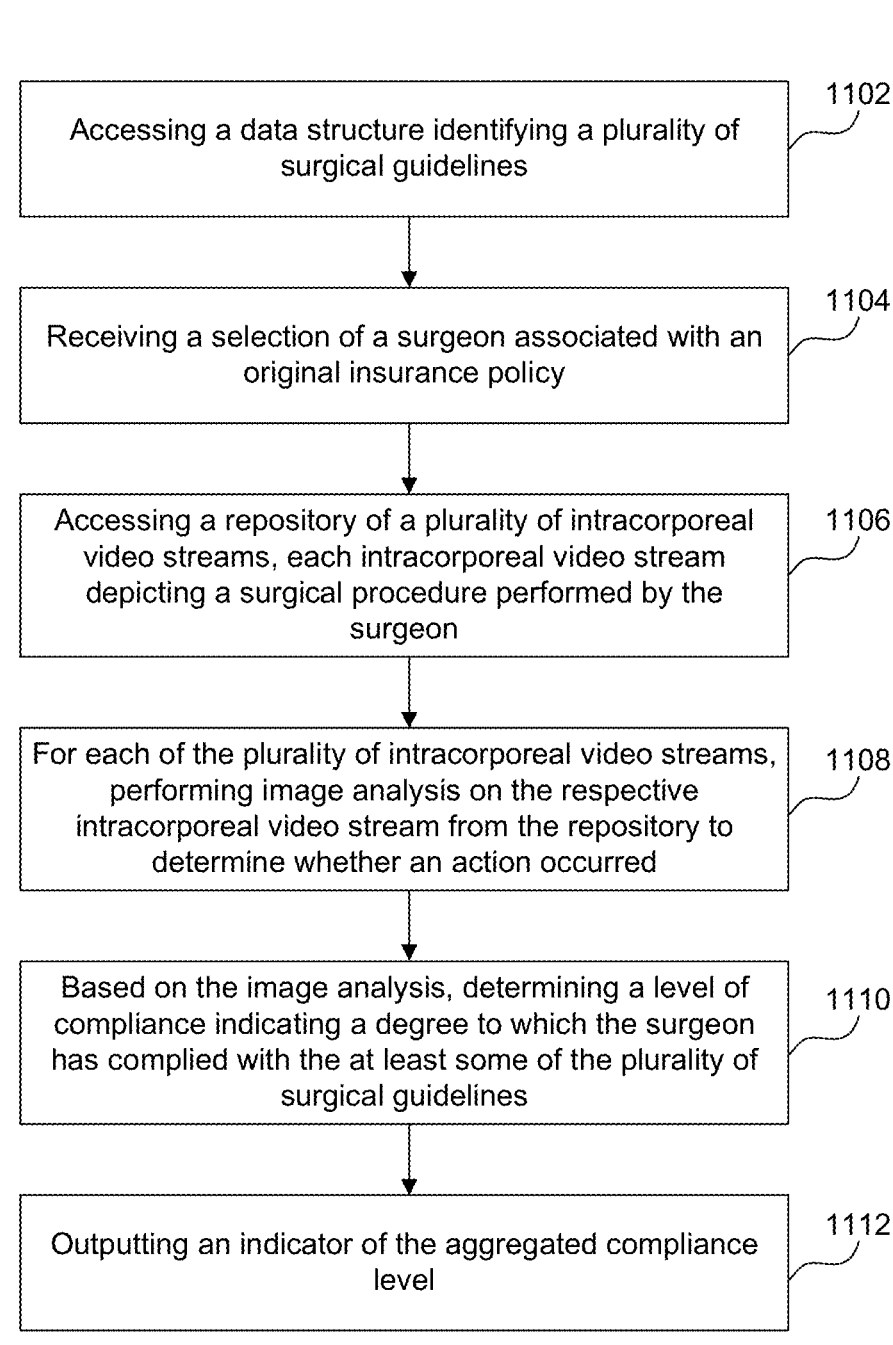

1102

Accessing a data structure identifying a plurality of surgical guidelines

1104

Receiving a selection of a surgeon associated with an original insurance policy

1106

Accessing a repository of a plurality of intracorporeal video streams, each intracorporeal video stream depicting a surgical procedure performed by the surgeon

1108

For each of the plurality of intracorporeal video streams, performing image analysis on the respective intracorporeal video stream from the repository to determine whether an action occurred

1110

Based on the image analysis, determining a level of compliance indicating a degree to which the surgeon has complied with the at least some of the plurality of surgical guidelines

1112

Outputting an indicator of the aggregated compliance level

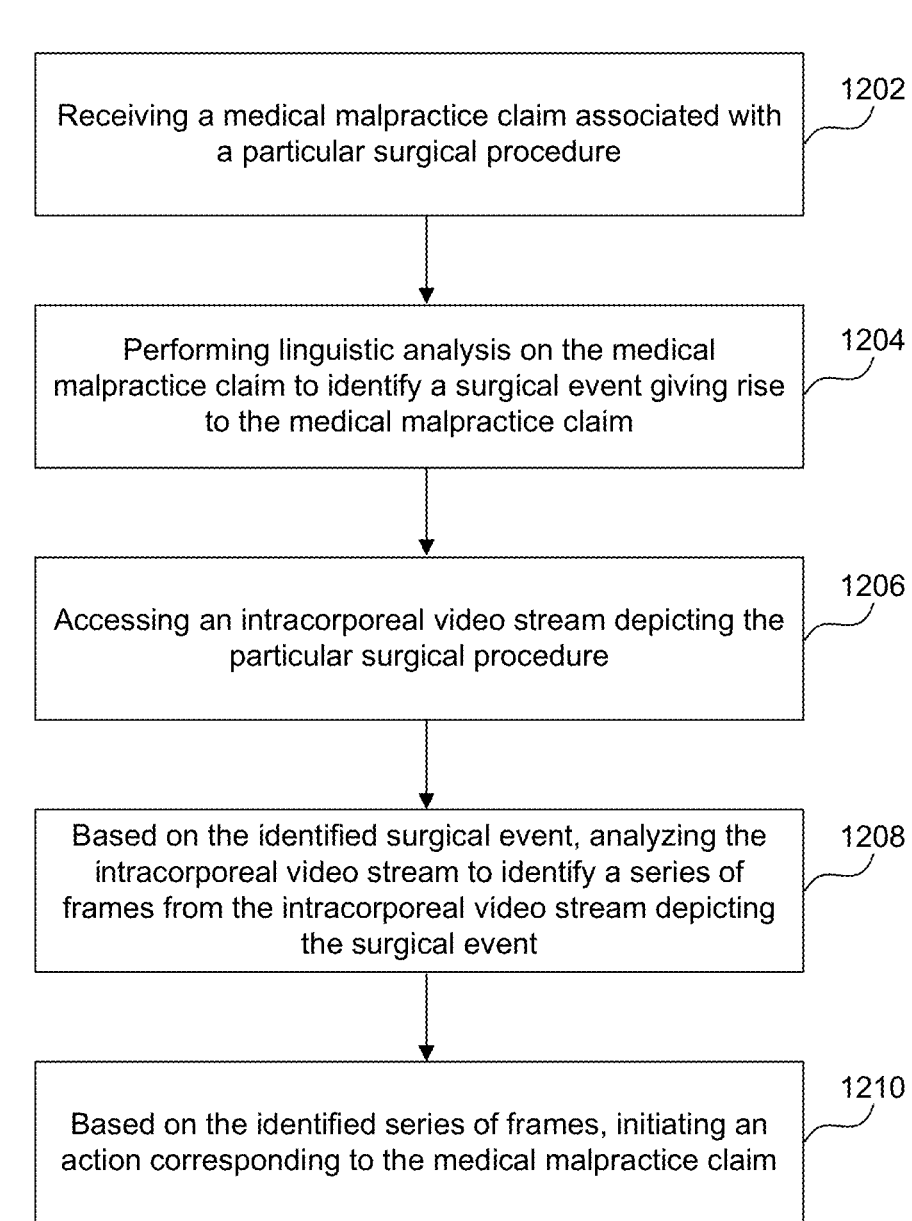

Receiving a medical malpractice claim associated with a particular surgical procedure          1202

Performing linguistic analysis on the medical malpractice claim to identify a surgical event giving rise to the medical malpractice claim          1204

Accessing an intracorporeal video stream depicting the particular surgical procedure          1206

Based on the identified surgical event, analyzing the intracorporeal video stream to identify a series of frames from the intracorporeal video stream depicting the surgical event          1208

Based on the identified series of frames, initiating an action corresponding to the medical malpractice claim          1210

Medical malpractice claim 1302

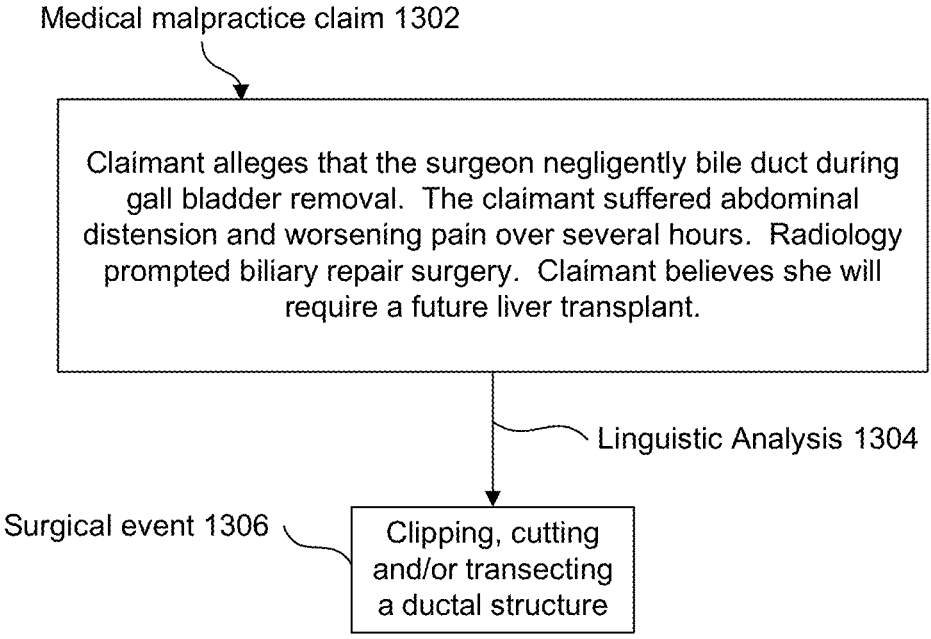

Claimant alleges that the surgeon negligently bile duct during gall bladder removal.  The claimant suffered abdominal distension and worsening pain over several hours.  Radiology prompted biliary repair surgery.  Claimant believes she will require a future liver transplant.

Linguistic Analysis 1304

Surgical event 1306

Clipping, cutting and/or transecting a ductal structure

FIG. 13

Intracorporeal
video stream
1402

Sequence of frames
depicting bile duct
injury
1404

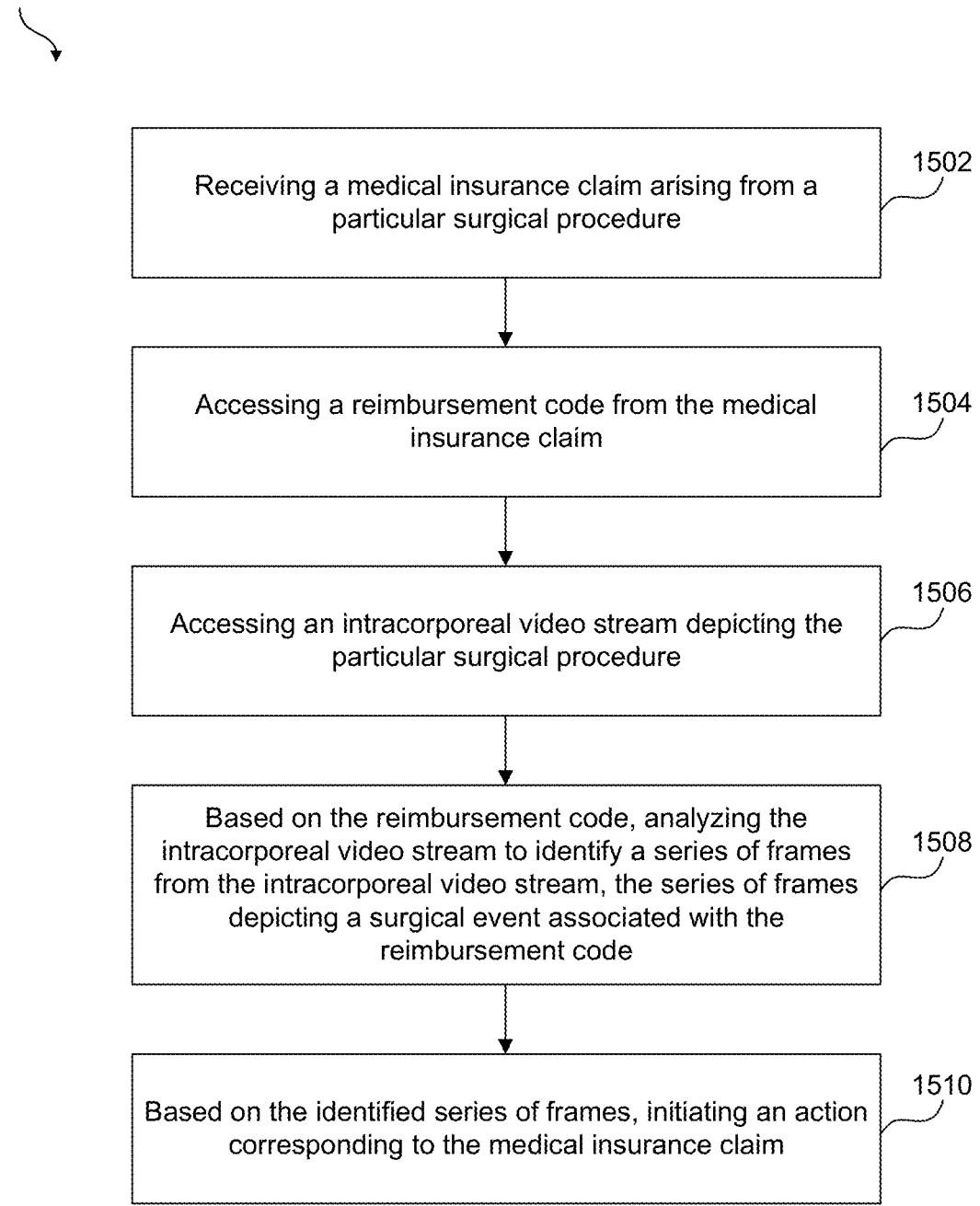

1500

Receiving a medical insurance claim arising from a particular surgical procedure — 1502

Accessing a reimbursement code from the medical insurance claim — 1504

Accessing an intracorporeal video stream depicting the particular surgical procedure — 1506

Based on the reimbursement code, analyzing the intracorporeal video stream to identify a series of frames from the intracorporeal video stream, the series of frames depicting a surgical event associated with the reimbursement code — 1508

Based on the identified series of frames, initiating an action corresponding to the medical insurance claim — 1510

Intracorporeal video stream
1602

CPT 47563 -- Laparoscopy, surgical; cholecystectomy with cholangiography

1604
Reimbursement code

1606

Sequence of frames depicting laparoscopic cholecystectomy with cholangiography

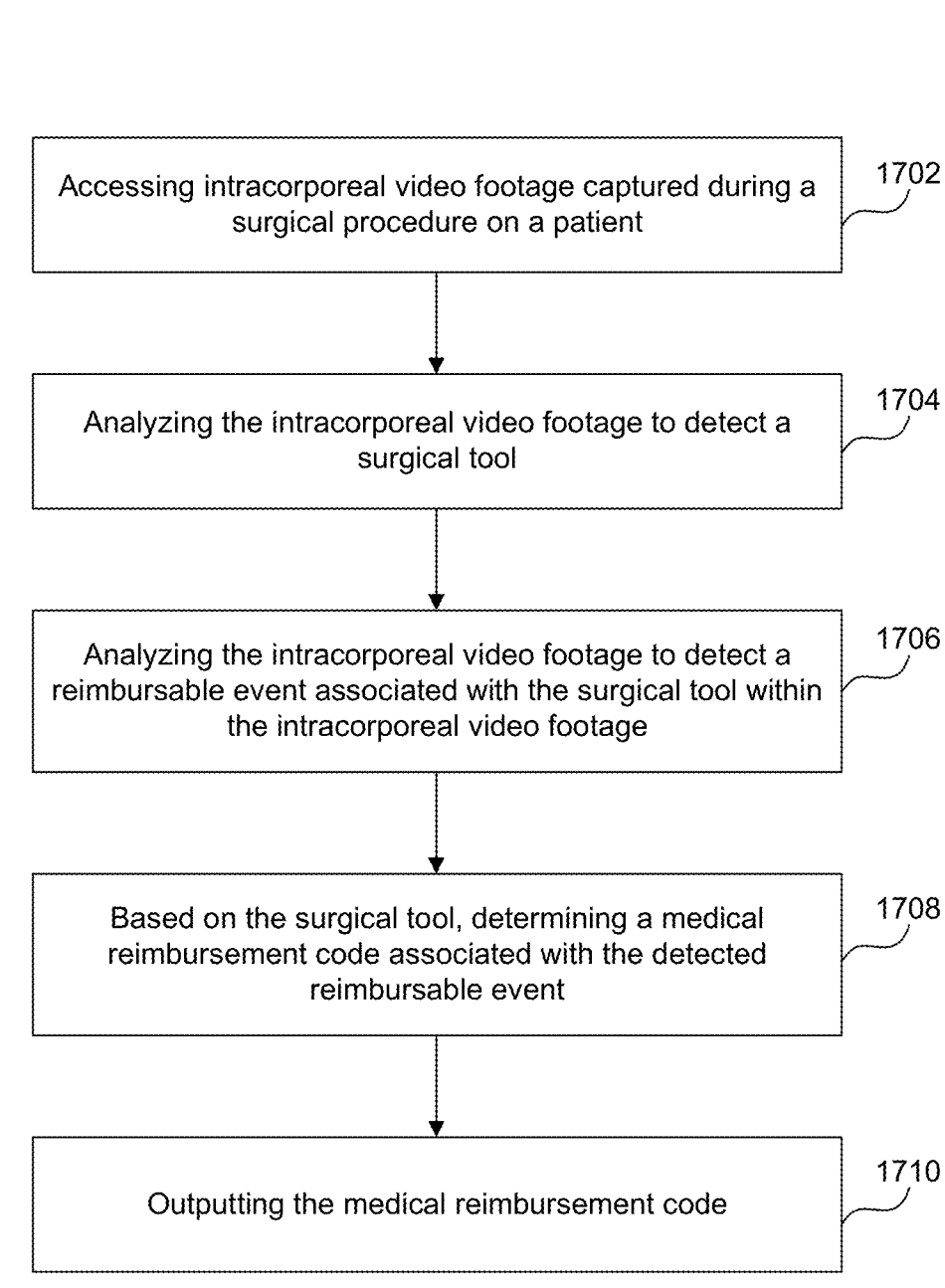

1700

Accessing intracorporeal video footage captured during a surgical procedure on a patient — 1702

Analyzing the intracorporeal video footage to detect a surgical tool — 1704

Analyzing the intracorporeal video footage to detect a reimbursable event associated with the surgical tool within the intracorporeal video footage — 1706

Based on the surgical tool, determining a medical reimbursement code associated with the detected reimbursable event — 1708

Outputting the medical reimbursement code — 1710

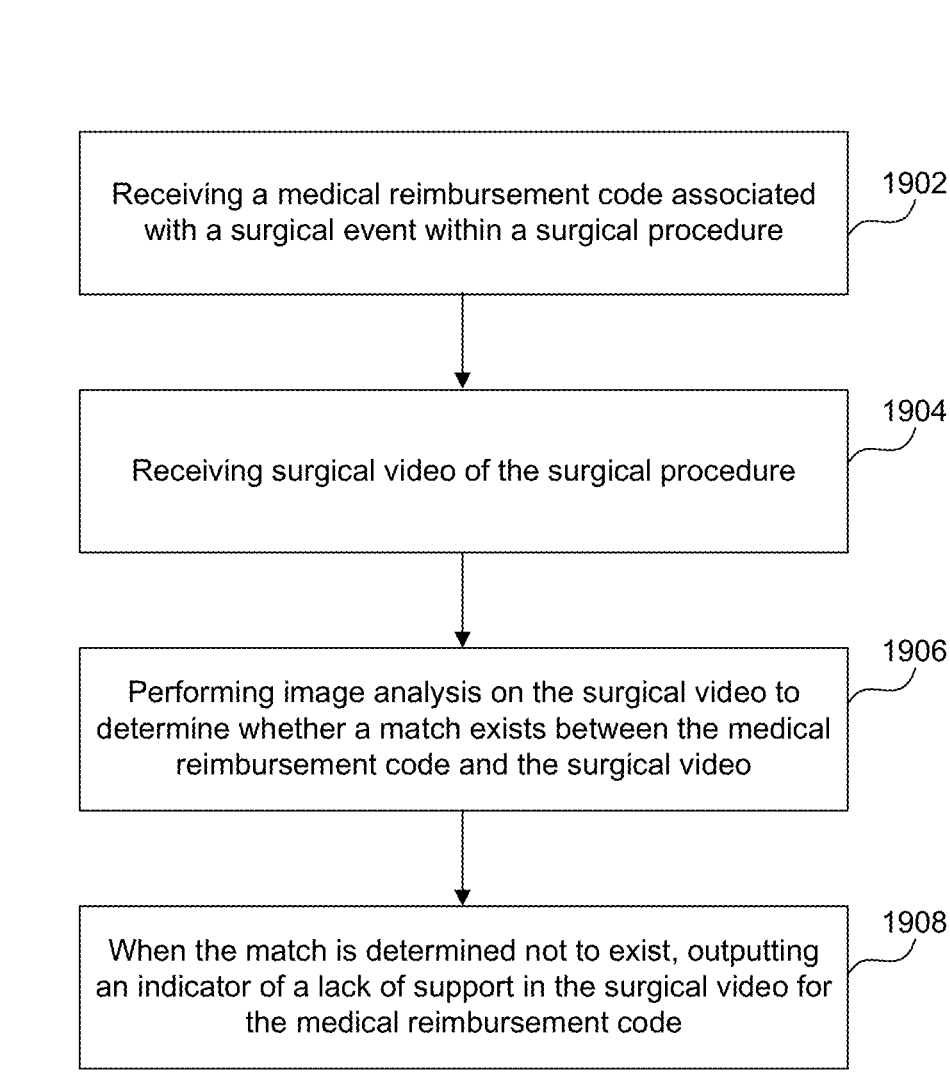

Receiving a medical reimbursement code associated with a surgical event within a surgical procedure — 1902

Receiving surgical video of the surgical procedure — 1904

Performing image analysis on the surgical video to determine whether a match exists between the medical reimbursement code and the surgical video — 1906

When the match is determined not to exist, outputting an indicator of a lack of support in the surgical video for the medical reimbursement code — 1908

FIG. 19

Computer System 2000

ANALYZING SURGICAL VIDEOS TO DETERMINE COMPLIANCE WITH SELECTED SURGICAL GUIDELINES

CROSS-REFERENCE TO RELATED APPLICATIONS

This application claims priority to U.S. Ser. No. 63/346,987, filed May 30, 2022 titled "USAGE AND ANALYSIS OF SURGICAL VIDEOS," U.S. Ser. No. 63/389,130, filed Jul. 14, 2022 titled "SYSTEMS AND METHODS FOR COMPLIANCE IMPROVEMENT IN SURGICAL PROCEDURES," U.S. Ser. No. 63/399,698, filed Aug. 21, 2022 titled "USAGE AND ANALYSIS OF SURGICAL VIDEOS FOR COMPLIANCE IMPROVEMENT IN SURGICAL PROCEDURES," and U.S. Ser. No. 63/411,758, filed Sep. 30, 2022 titled "SYSTEMS AND METHODS FOR COMPLIANCE IMPROVEMENT IN SURGICAL PROCEDURES." The contents of the foregoing applications are herein incorporated by reference.

BACKGROUND

Technical Field

Aspects of the present disclosure relate to components, systems, and methods for analyzing surgical footage. More particularly, aspects of the present disclosure relate to components, systems, and methods for analyzing surgical footage to improve compliance with medical guidelines.

Background

It is important for medical professional, such as surgeons, to follow medical guidelines when performing medical procedures. Accordingly, medical centers or departments are interested in determining whether a selected group of surgeons, such as those who share a particular specialty, comply with surgical guidelines. Medical centers or departments may also wish to check compliance with a customized set of guidelines chosen from a larger group of guidelines. For example, if a hospital has unusually high post-operative infection rates, the medical centers or departments may be particularly interested in guidelines that impact infection. Compliance with medical guidelines can also influence insurance premiums of medical professionals and medical centers and departments.

When medical professionals perform medical procedures, significant amounts of information, such as written, audio, and/or video data, is produced. If simplified, this information could prove useful when processing various medical transactions. For example, in addition to considering insurance premiums, medical malpractice and insurance claims are a common transactional component of the medical field. With the significant amount of information resulting from a medical procedure, processing these transactions can be tedious and error-prone.

SUMMARY

In an aspect, a non-transitory computer readable medium can contain instructions that, when executed by at least one processor, cause the at least one processor to execute operations to perform intracorporeal video analysis operations for monitoring compliance with surgical guidelines. In the aspect, descriptors of a group of surgical guidelines can be presented. A selection of a subgroup of surgical guidelines from the group of surgical guidelines can then be received. The subgroup can include at least one, but not all, of the surgical guidelines from the group of surgical guidelines. A repository of intracorporeal video streams can be accessed. The video streams can depict performance, by at least one surgeon, of a plurality of surgical procedures governed by the subgroup of surgical guidelines. For each surgical procedure of the plurality of surgical procedures, an image analysis can be performed on a particular intracorporeal video stream from the repository. The particular intracorporeal video stream can capture a respective surgical procedure. The imagine analysis can be used to determine whether at least one surgical guideline was followed or complied with. Based on this image analysis, an aggregated compliance level can be determined. The aggregated compliance level can indicate compliance, of the at least one surgeon, with the selected subgroup of surgical guidelines. Then, an indicator of the aggregated compliance level can be output.

System, device, and computer program product aspects are also disclosed.

Further features and advantages, as well as the structure and operation of various aspects, are described in detail below with reference to the accompanying drawings. It is noted that the specific aspects described herein are not intended to be limiting. Such aspects are presented herein for illustrative purposes only. Additional aspects will be apparent to persons skilled in the relevant art(s) based on the teachings contained herein.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

FIG. 5 is a flowchart of an example process for determining group compliance using surgical guidelines, according to some aspects of the present disclosure.

FIG. 9 is a flowchart of an example process for determining compliance with selected surgical guidelines, according to some aspects of the present disclosure.

FIG. 10 is an illustration of groups of surgical guidelines, according to some aspects of the present disclosure.

FIG. 11 is a flowchart of an example process of surgical video analysis for insurance premium adjustment, according to some aspects of the present disclosure.

FIG. 12 is a flowchart of an example process for correlating a medical malpractice claim with a portion of a video, according to some aspects of the present disclosure.

FIG. 13 is a flowchart of an example linguistic analysis performed on a medical malpractice claim to identify a surgical event, according to some aspects of the present disclosure.

FIG. 15 is a flowchart of an example process for correlating a medical claim code with a portion of a video, according to some aspects of the present disclosure.

FIG. 17 is a flowchart of an example process for analyzing surgical video to support insurance reimbursement, according to some aspects of the present disclosure.

FIG. 19 is a flowchart of an example process for analyzing surgical videos to identify a billing coding mismatch, according to some aspects of the present disclosure.

In the drawings, like reference numbers generally indicate identical or similar elements. Additionally, generally, the left-most digit(s) of a reference number identifies the drawing in which the reference number first appears.

Aspects of the present disclosure will be described with reference to the accompanying drawings.

DETAILED DESCRIPTION

Figure 1:
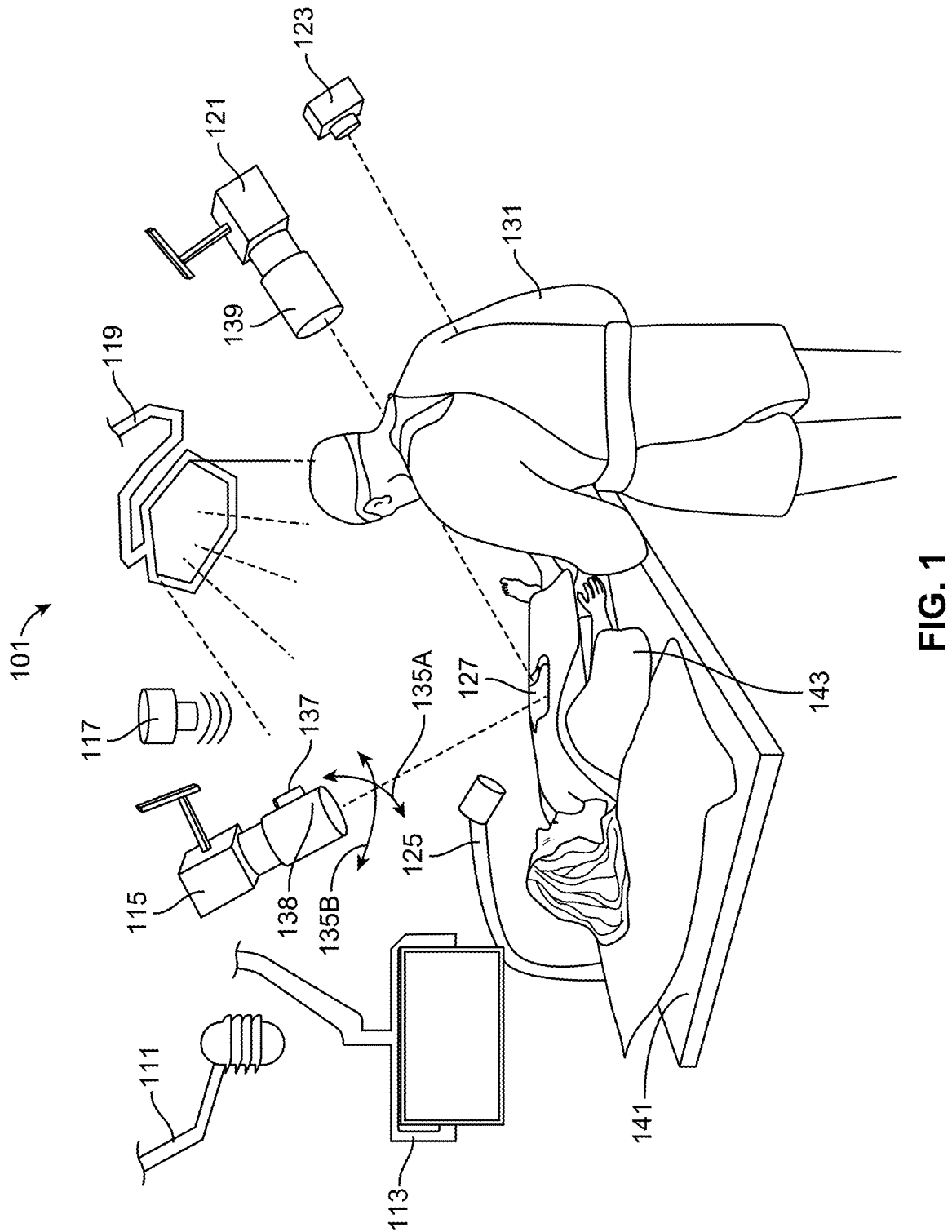
FIG. 1 is a perspective view of an example operating room, according to some aspects of the present disclosure.

FIG. 1 shows an example operating room 101, consistent with disclosed aspects. A patient 143 is illustrated on an operating table 141. Room 101 may include audio sensors, video/image sensors, chemical sensors, and other sensors, as well as various light sources (e.g., light source 119) for facilitating capture of video and audio data, as well as data from other sensors, during the surgical procedure. For example, room 101 may include one or more microphones (e.g., audio sensor 111), several cameras (e.g., overhead cameras 115, 121, and 123, and a tableside camera 125) for capturing video/image data during surgery. While some of the cameras (e.g., cameras 115, 123, and 125) may capture video/image data of operating table 141 (e.g., the cameras may capture the video/image data at a location 127 of a body of patient 143 on which a surgical procedure is performed), camera 121 may capture video/image data of other parts of operating room 101. For instance, camera 121 may capture video/image data of a surgeon 131 performing the surgery. In some cases, cameras may capture video/image data of surgical team personnel, such as an anesthesiologist, nurses, surgical tech and the like located in operating room 101. Additionally, operating room cameras may capture video/ image data of medical equipment located in the room. During surgery, some of the cameras (e.g., cameras 115, 121, 123, and 125) may capture intracorporeal video footage. In various aspects, one or more of cameras 115, 121, 123, and 125 may be movable. For example, as shown in FIG. 1, camera 115 may be rotated as indicated by arrows 135A showing a pitch direction, and arrows 135B showing a yaw direction for camera 115. In various aspects, pitch and yaw angles of cameras (e.g., camera 115) may be electronically controlled such that camera 115 points at a region-of-interest (ROI), of which video/image data needs to be captured. For example, camera 115 may be configured to track a surgical instrument (also referred to as a surgical tool) within location 127, an anatomical structure, a hand of surgeon 131, an incision, a movement of anatomical structure, and the like. In various aspects, camera 115 may be equipped with a laser 137 (e.g., an infrared laser) for precision tracking. In some cases, camera 115 may be tracked automatically via a computer-based camera control application that uses an image recognition algorithm for positioning the camera to capture video/image data of a ROI. For example, the camera control application may identify an anatomical structure, identify a surgical tool, hand of a surgeon, bleeding, motion, and the like at a particular location within the anatomical structure, and track that location with camera 115 by rotating camera 115 by appropriate yaw and pitch angles. In some aspects, the camera control application may control positions (i.e., yaw and pitch angles) of various cameras 115, 121, 123, and 125 to capture video/image date from different ROIs during a surgical procedure. Additionally or alternatively, a human operator may control the position of various cameras 115, 121, 123, and 125, and/or the human operator may supervise the camera control application in controlling the position of the cameras.

Cameras 115, 121, 123, and 125 may further include zoom lenses for focusing in on and magnifying one or more ROIs. In an example aspect, camera 115 may include a zoom lens 138 for zooming closely to a ROI (e.g., a surgical tool in the proximity of an anatomical structure). Camera 121 may include a zoom lens 139 for capturing video/image data from a larger area around the ROI. For example, camera 121 may capture video/image data for the entire location 127. In some aspects, video/image data obtained from camera 121 may be analyzed to identify a ROI during the surgical procedure, and the camera control application may be configured to cause camera 115 to zoom towards the ROI identified by camera 121.

In various aspects, the camera control application may be configured to coordinate the position, focus, and magnification of various cameras during a surgical procedure. For example, the camera control application may direct camera 115 to track an anatomical structure and may direct camera 121 and 125 to track a surgical instrument. Cameras 121 and 125 may track the same ROI (e.g., a surgical instrument) from different view angles. For example, video/image data obtained from different view angles may be used to determine the position of the surgical instrument relative to a surface of the anatomical structure, to determine a condition of an anatomical structure, to determine pressure applied to an anatomical structure, or to determine any other information where multiple viewing angles may be beneficial. By way of another example, bleeding may be detected by one camera, and one or more other cameras may be used to identify the source of the bleeding.

In various aspects, control of position, orientation, settings, and/or zoom of cameras 115, 121, 123, and 125 may be rule-based and follow an algorithm developed for a given surgical procedure. For example, the camera control application may be configured to direct camera 115 to track a surgical instrument, to direct camera 121 to location 127, to direct camera 123 to track the motion of the surgeon's hands, and to direct camera 125 to an anatomical structure. The algorithm may include any suitable logical statements determining position, orientation, settings and/or zoom for cameras 115, 121, 123, and 125 depending on various events during the surgical procedure. For example, the algorithm may direct at least one camera to a region of an anatomical structure that develops bleeding during the procedure. Some non-limiting examples of settings of cameras 115, 121, 123, and 125 that may be controlled (for example by the camera control application) may include image pixel resolution, frame rate, image and/or color correction and/or enhancement algorithms, zoom, position, orientation, aspect ratio, shutter speed, aperture, focus, and so forth.

In various cases, when a camera (e.g., camera 115) tracks a moving or deforming object (e.g., when camera 115 tracks a moving surgical instrument, or a moving/pulsating anatomical structure), a camera control application may determine a maximum allowable zoom for camera 115, such that the moving or deforming object does not escape a field of view of the camera. In an example aspect, the camera control application may initially select the first zoom for camera 115, evaluate whether the moving or deforming object escapes the field of view of the camera, and adjust the zoom of the camera as necessary to prevent the moving or deforming object from escaping the field of view of the camera. In various aspects, the camera zoom may be readjusted based on a direction and a speed of the moving or deforming object.

Figure 2:
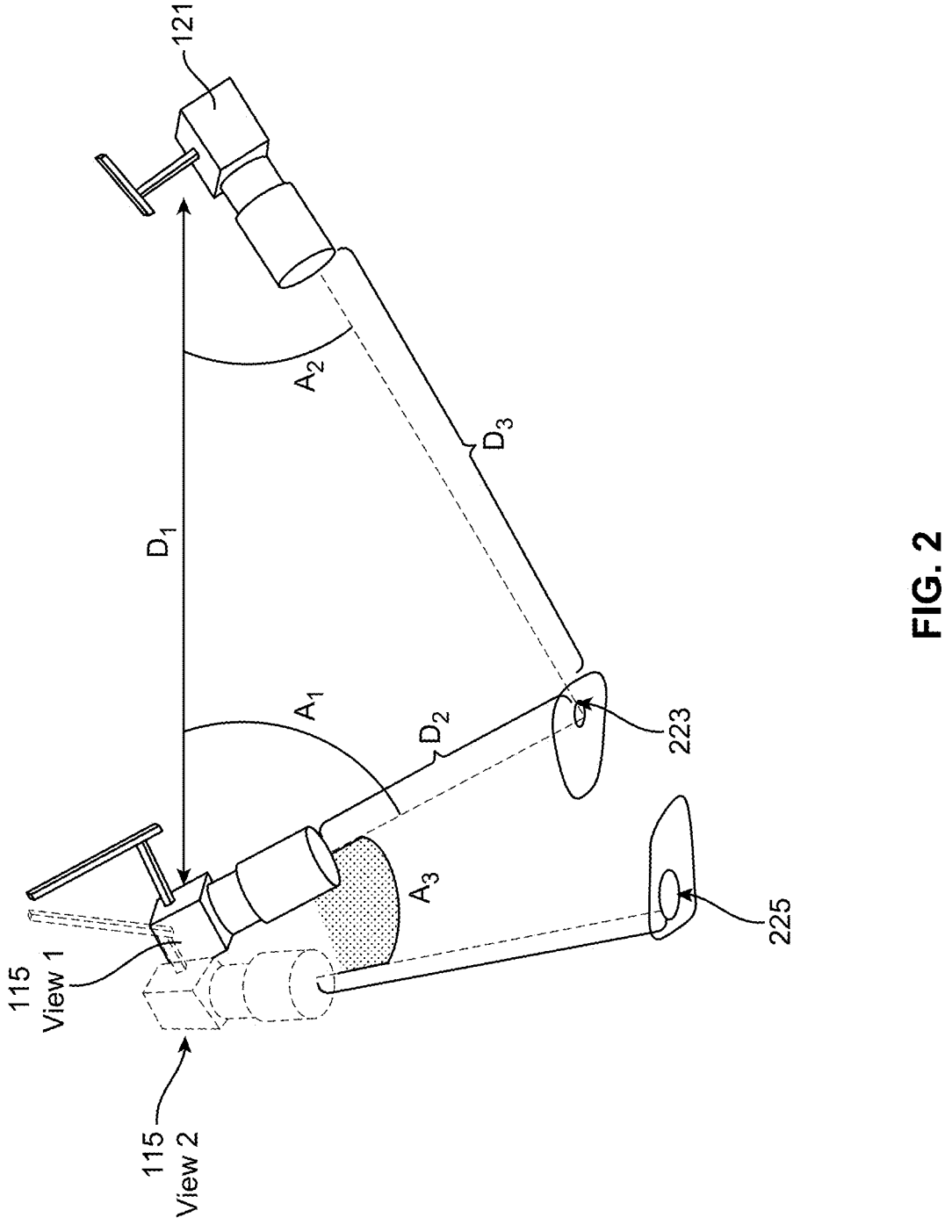
FIG. 2 is a perspective view of cameras, according to some aspects of the present disclosure.

In various aspects, one or more image sensors may include moving cameras 115, 121, 123, and 125. Cameras 115, 121, 123, and 125 may be used for determining sizes of anatomical structures and determining distances between different ROIs, for example using triangulation. For example, FIG. 2 shows exemplary cameras 115 and 121 supported by movable elements such that the distance between the two cameras is $D_1$, as shown in FIG. 2. Both cameras point at ROI 223. By knowing the positions of cameras 115 and 121 and the direction of an object relative to the cameras (e.g., by knowing angles $A_1$ and $A_2$, as shown in FIG. 2, for example based on correspondences between pixels depicting the same object or the same real-world point in the images captured by 115 and 121), distances $D_2$ and $D_3$ may be calculated using, for example, the law of sines and the known distance between the two cameras $D_1$. In an example aspect, when camera 115 rotates by a small angle $A_3$ (measured in radians), to point at ROI 225, the distance between ROI 223 and ROI 225 may be approximated (for small angles $A_3$) by $A_3D_2$. More accuracy may be obtained using another triangulation process.

In some aspects, the operating room may include sensors embedded in various components depicted or not depicted in FIG. 1. Examples of such sensors may include: audio sensors; image sensors; motion sensors; positioning sensors; chemical sensors; temperature sensors; barometers; pressure sensors; proximity sensors; electrical impedance sensors; electrical voltage sensors; electrical current sensors; or any other detector capable of providing feedback on the environment or a surgical procedure, including, for example, any kind of medical or physiological sensor configured to monitor patient 143.

In various aspects, temperature sensors may include infrared cameras (e.g., an infrared camera 117) for thermal imaging. Infrared camera 117 may allow measurements of the surface temperature of an anatomic structure at different points of the structure. Similar to visible cameras 115, 121, 123, and 125, infrared camera 117 may be rotated using yaw or pitch angles, and may be used to capture intracorporeal video footage. Additionally or alternatively, camera 117 may include an image sensor configured to capture image from any light spectrum, include infrared image sensor, hyperspectral image sensors, and so forth.

FIG. 1 includes a display screen 113 that may show views from different cameras 115, 121, 123, and 125, as well as other information. For example, display screen 113 may show a zoomed-in image of a tip of a surgical instrument and a surrounding tissue of an anatomical structure in proximity to the surgical instrument.

Figure 3:
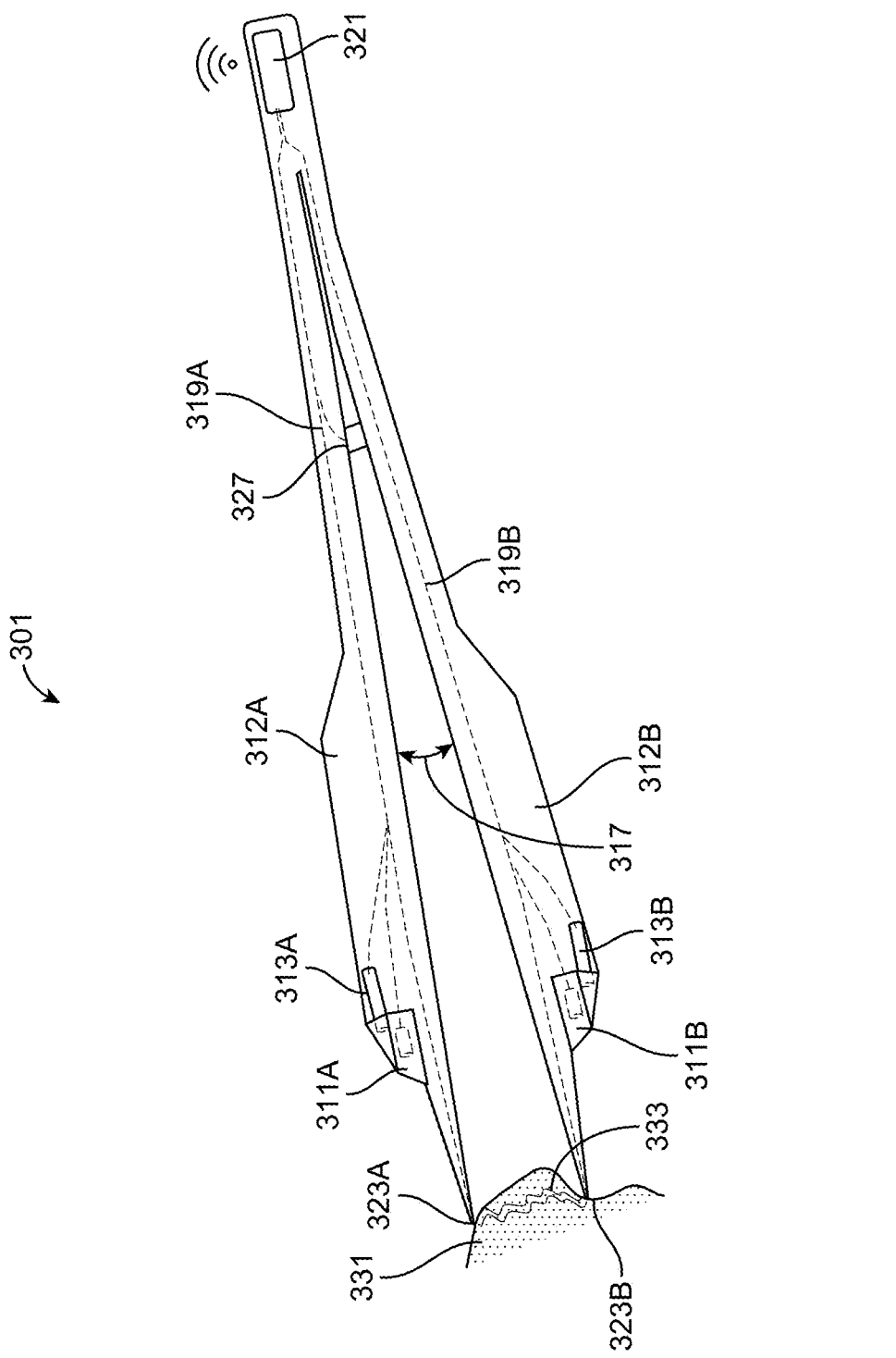
FIG. 3 is a perspective view of an example of a surgical instrument, according to some aspects of the present disclosure.

FIG. 3 shows an example aspect of a surgical instrument 301 that may include multiple sensors and light-emitting sources. Consistent with the present aspects, a surgical instrument may refer to a medical device, a medical instrument, an electrical or mechanical tool, a surgical tool, a diagnostic tool, and/or any other instrumentality that may be used during a surgery. As shown, instrument 301 may include cameras 311A and 311B, light sources 313A and 313B as well as tips 323A and 323B for contacting tissue 331. During surgery, cameras 311A and 311B may capture intracorporeal video footage. Cameras 311A and 311B may be connected via data connection 319A and 319B to a data transmitting device 321. In an example aspect, device 321 may transmit data to a data-receiving device using a wireless communication or using a wired communication. In an example aspect, device 321 may use WiFi, Bluetooth, NFC communication, inductive communication, or any other suitable wireless communication for transmitting data to a data-receiving device. The data-receiving device may include any form of receiver capable of receiving data transmissions. Additionally or alternatively, device 321 may use optical signals to transmit data to the data-receiving device (e.g., device 321 may use optical signals transmitted through the air or via optical fiber). In some aspects, device 301 may include local memory for storing at least some of the data received from cameras 311A and 311B. Additionally, device 301 may include a processor for compressing video/image data before transmitting the data to the data-receiving device.

In various aspects, for example when device 301 is wireless, it may include an internal power source (e.g., a battery, a rechargeable battery, and the like) and/or a port for recharging the battery, an indicator for indicating the amount of power remaining for the power source, and one or more input controls (e.g., buttons) for controlling the operation of device 301. In some aspects, control of device 301 may be accomplished using an external computing device (e.g., a smartphone, tablet, smart glasses) communicating with device 301 via any suitable connection (e.g., WiFi, Bluetooth, and the like). In an example aspect, input controls for device 301 may be used to control various parameters of sensors or light sources. Additionally, instrument 301 may be configured to measure data related to various properties of tissue 331 via tips 323A and 323B and transmit the measured data to device 321. For example, tips 323A and 323B may be used to measure the electrical resistance and/or impedance of tissue 331, the temperature of tissue 331, mechanical properties of tissue 331 and the like. To determine elastic properties of tissue 331, for example, tips 323A and 323B may be first separated by an angle 317 and applied to tissue 331. The tips may be configured to move such as to reduce angle 317, and the motion of tips may result in pressure on tissue 331. Such pressure may be measured (e.g., via a piezoelectric element 327 that may be located between a first branch 312A and a second branch 312B of instrument 301), and based on the change in angle 317 (i.e., strain) and the measured pressure (i.e., stress), the elastic properties of tissue 331 may be measured. Furthermore, based on angle 317 distance between tips 323A and 323B may be measured, and this distance may be transmitted to device 321. Such distance measurements may be used as a length scale for various video/image data that may be captured by various cameras 115, 121, 123, and 125, as shown in FIG. 1.

Instrument 301 is only one example of possible surgical instrument, and other surgical instruments such as scalpels, graspers (e.g., forceps), clamps and occluders, needles, retractors, cutters, dilators, suction tips, and tubes, sealing devices, irrigation and injection needles, scopes and probes, and the like, may include any suitable sensors and light-emitting sources. In various cases, the type of sensors and light-emitting sources may depend on a type of surgical instrument used for a surgical procedure. In various cases, these other surgical instruments may include a device similar to device 301, as shown in FIG. 3, for collecting and transmitting data to any suitable data-receiving device.

Consistent with disclosed aspects, a method may involve accessing at least one video of a surgical procedure. The video may include any form of recorded visual media including recorded images and/or sound. The video may be stored as a video file such as an Audio Video Interleave (AVI) file, a Flash Video Format (FLV) file, QuickTime File Format (MOV), MPEG (MPG, MP4, M4P, etc.), a Windows Media Video (WMV) file, a Material Exchange Format (MXF) file, or any other suitable video file formats, for example as described above.

A surgical procedure may include any medical procedure involving manual or operative procedures on a patient's body. Surgical procedures may include cutting, abrading, suturing, or other techniques that involve physically changing body tissues and organs. A video of a surgical procedure may include any series of still images that were captured during the surgical procedure. In some aspects, at least a portion of the surgical procedure may be depicted in one or more of the still images included in the video. For example, the video of the surgical procedure may be recorded by an image capture device, such as a camera, in an operating room or in a cavity of a patient. Accessing the video of the surgical procedure may include retrieving the video from a storage device (such as one or more memory units, a video server, a cloud storage platform, or any other storage platform), receiving the video from another device through a communication device, capturing the video using image sensors, or any other means for electronically accessing data or files.

Some aspects of the present disclosure may involve causing the at least one video to be output for display. Outputting the at least one video may include any process by which the video is produced, delivered, or displayed using a computer or at least one processor. As used herein, "display" may refer to any manner in which a video may be presented to a user for playback. In some aspects, outputting the video may include presenting the video using a display device, such as a screen (e.g., an OLED, QLED LCD, plasma, CRT, DLPT, electronic paper, or similar display technology), a light projector (e.g., a movie projector, a slide projector), a 3D display, screen of a mobile device, electronic glasses or any other form of visual and/or audio presentation. In other aspects, outputting the video for display may include storing the video in a location that is accessible by one or more other computing devices. Such storage locations may include a local storage (such as a hard drive of flash memory), a network location (such as a server or database), a cloud computing platform, or any other accessible storage location. The video may be accessed from a separate computing device for display on the separate computing device. In some aspects, outputting the video may include transmitting the video to an external computing device. For example, outputting the video for display may include transmitting the video through a network to a user device for playback on the user device.

Figure 4:
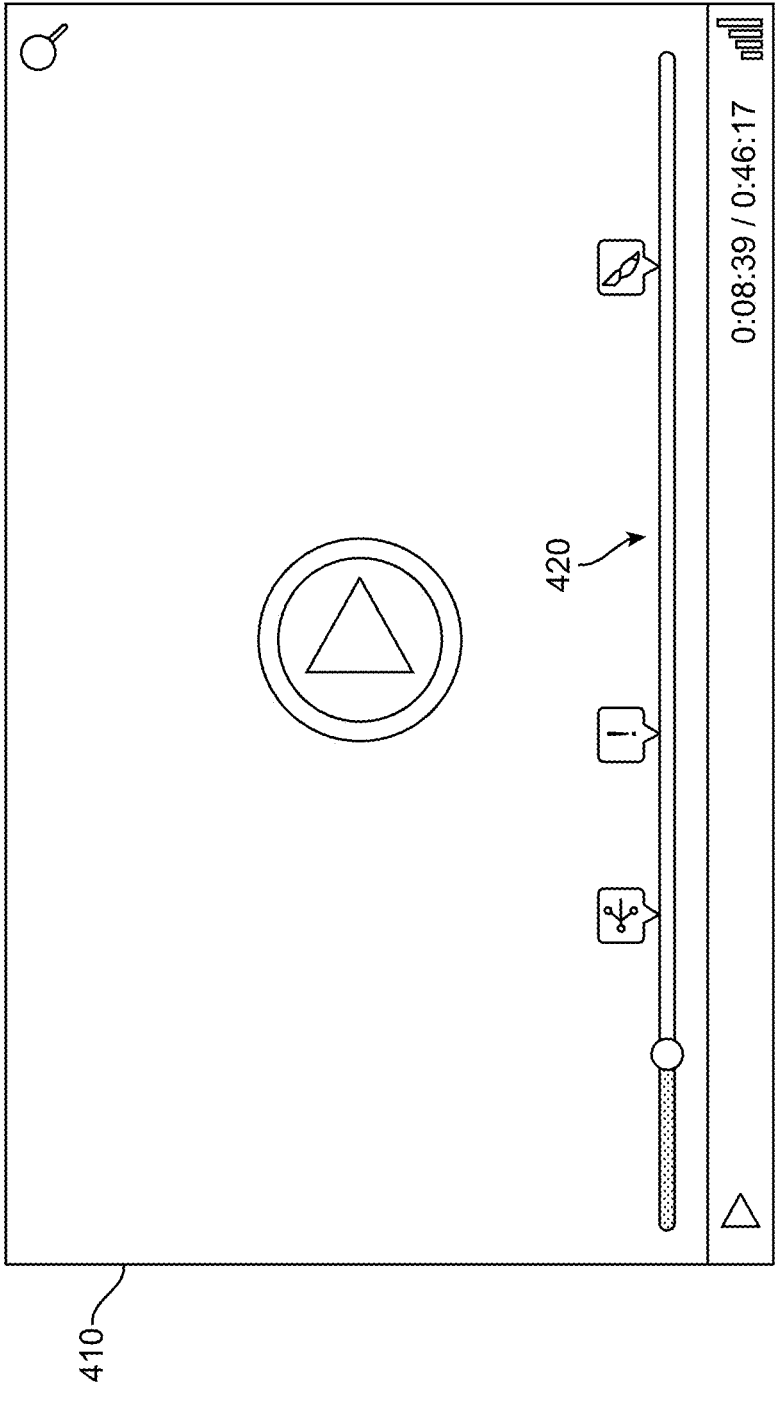
FIG. 4 is an illustration of a video of a surgical procedure with an overlaid timeline, according to some aspects of the present disclosure.

FIG. 4 illustrates presenting video in a video playback region 410, which may sequentially display one or more frames of the video. A timeline 420 may be overlaid on the video.

In some embodiments, machine learning algorithms (also referred to as machine learning models in the present disclosure) may be trained using training examples, for example in the cases described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recurrent neural network algorithms, linear machine learning models, non-linear machine learning models, ensemble algorithms, and so forth. For example, a trained machine learning algorithm may comprise an inference model, such as a predictive model, a classification model, a data regression model, a clustering model, a segmentation model, an artificial neural network (such as a deep neural network, a convolutional neural network, a recurrent neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters may be set manually by a person or automatically by an process external to the machine learning algorithm (such as a hyper parameter search algorithm), and the parameters of the machine learning algorithm may be set by the machine learning algorithm based on the training examples. In some implementations, the hyper-parameters may be set based on the training examples and the validation examples, and the parameters may be set based on the training examples and the selected hyper-parameters. For example, given the hyper-parameters, the parameters may be conditionally independent of the validation examples.

In some embodiments, trained machine learning algorithms (also referred to as machine learning models and trained machine learning models in the present disclosure) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value corresponding to the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value corresponding to an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs, for example in the cases described below. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

In some embodiments, generative models may be configured to generate new content, such as textual content, visual content, auditory content, graphical content, and so forth. In some examples, generative models may generate new content without input. In other examples, generative models may generate new content based on an input. In one example, the new content may be fully determined from the input, where every usage of the generative model with the same input will produce the same new content. In another example, the new content may be associated with the input but not fully determined from the input, where every usage of the generative model with the same input may product a different new content that is associated with the input. In some examples, a generative model may be a result of training a machine learning generative algorithm with training examples. An example of such training example may include a sample input, together with a sample content associated with the sample input. Some non-limiting examples of such generative models may include Deep Generative Model (DGM), Generative Adversarial Network model (GAN), auto-regressive model, Variational AutoEncoder (VAE), transformers based generative model, artificial neural networks based generative model, hard-coded generative model, and so forth.

Some non-limiting examples of audio data may include audio recordings, audio stream, audio data that includes speech, audio data that includes music, audio data that includes ambient noise, digital audio data, analog audio data, digital audio signals, analog audio signals, mono audio data, stereo audio data, surround audio data, audio data captured using at least one audio sensor, audio data generated artificially, and so forth. In one example, audio data may be generated artificially from textual content, for example using text-to-speech algorithms. In another example, audio data may be generated using a generative machine learning model. In some embodiments, analyzing audio data (for example, by the methods, steps and modules described herein) may comprise analyzing the audio data to obtain a preprocessed audio data, and subsequently analyzing the audio data and/or the preprocessed audio data to obtain the desired outcome. One of ordinary skill in the art will recognize that the followings are examples, and that the audio data may be preprocessed using other kinds of preprocessing methods. In some examples, the audio data may be preprocessed by transforming the audio data using a transformation function to obtain a transformed audio data, and the preprocessed audio data may comprise the transformed audio data. For example, the transformation function may comprise a multiplication of a vectored time series representation of the audio data with a transformation matrix. For example, the transformation function may comprise convolutions, audio filters (such as low-pass filters, high-pass filters, band-pass filters, all-pass filters, etc.), linear functions, nonlinear functions, and so forth. In some examples, the audio data may be preprocessed by smoothing the audio data, for example using Gaussian convolution, using a median filter, and so forth. In some examples, the audio data may be preprocessed to obtain a different representation of the audio data. For example, the preprocessed audio data may comprise: a representation of at least part of the audio data in a frequency domain; a Discrete Fourier Transform of at least part of the audio data; a Discrete Wavelet Transform of at least part of the audio data; a time/frequency representation of at least part of the audio data; a spectrogram of at least part of the audio data; a log spectrogram of at least part of the audio data; a Mel-Frequency Spectrum of at least part of the audio data; a sonogram of at least part of the audio data; a periodogram of at least part of the audio data; a representation of at least part of the audio data in a lower dimension; a lossy representation of at least part of the audio data; a lossless representation of at least part of the audio data; a time order series of any of the above; any combination of the above; and so forth. In some examples, the audio data may be preprocessed to extract audio features from the audio data. Some non-limiting examples of such audio features may include: auto-correlation; number of zero crossings of the audio signal; number of zero crossings of the audio signal centroid; MP3 based features; rhythm patterns; rhythm histograms; spectral features, such as spectral centroid, spectral spread, spectral skewness, spectral kurtosis, spectral slope, spectral decrease, spectral roll-off, spectral variation, etc.; harmonic features, such as fundamental frequency, noisiness, inharmonicity, harmonic spectral deviation, harmonic spectral variation, tristimulus, etc.; statistical spectrum descriptors; wavelet features; higher level features; perceptual features, such as total loudness, specific loudness, relative specific loudness, sharpness, spread, etc.; energy features, such as total energy, harmonic part energy, noise part energy, etc.; temporal features; and so forth. In some examples, analyzing the audio data may include calculating at least one convolution of at least a portion of the audio data, and using the calculated at least one convolution to calculate at least one resulting value and/or to make determinations, identifications, recognitions, classifications, and so forth.

In some embodiments, analyzing audio data (for example, in the cases described below) may comprise analyzing the audio data and/or the preprocessed audio data using one or more rules, functions, procedures, artificial neural networks, speech recognition algorithms, speaker recognition algorithms, speaker diarization algorithms, audio segmentation algorithms, noise cancelling algorithms, source separation algorithms, inference models, and so forth. Some non-limiting examples of such inference models may include: an inference model preprogrammed manually; a classification model; a data regression model; a result of training algorithms, such as machine learning algorithms and/or deep learning algorithms, on training examples, where the training examples may include examples of data instances, and in some cases, a data instance may be labeled with a corresponding desired label and/or result; and so forth.

Some non-limiting examples of image data may include images, grayscale images, color images, 2D images, 3D images, videos, 2D videos, 3D videos, frames, footages, data derived from other image data, and so forth. In some embodiments, analyzing image data (for example in the cases described below) may comprise analyzing the image data to obtain a preprocessed image data, and subsequently analyzing the image data and/or the preprocessed image data to obtain the desired outcome. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may comprise the transformed image data. For example, the transformed image data may comprise one or more convolutions of the image data. For example, the transformation function may comprise one or more image filters, such as low-pass filters, high-pass filters, band-pass filters, all-pass filters, and so forth. In some examples, the transformation function may comprise a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may comprise: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may comprise information based on and/or related to the extracted edges. In some examples, the image data may be preprocessed to extract image features from the image data. Some non-limiting examples of such image features may comprise information based on and/or related to: edges; corners; blobs; ridges; Scale Invariant Feature Transform (SIFT) features; temporal features; and so forth. In some examples, analyzing the image data may include calculating at least one convolution of at least a portion of the image data, and using the calculated at least one convolution to calculate at least one resulting value and/or to make determinations, identifications, recognitions, classifications, and so forth.

In some embodiments, analyzing image data (for example in the cases described below) may comprise analyzing the image data and/or the preprocessed image data using one or more rules, functions, procedures, artificial neural networks, object detection algorithms, face detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth. In some embodiments, analyzing image data (for example in the cases described below) may comprise analyzing pixels, voxels, point cloud, range data, etc. included in the image data.

A convolution may include a convolution of any dimension. A one-dimensional convolution is a function that transforms an original sequence of numbers to a transformed sequence of numbers. The one-dimensional convolution may be defined by a sequence of scalars. Each particular value in the transformed sequence of numbers may be determined by calculating a linear combination of values in a subsequence of the original sequence of numbers corresponding to the particular value. A result value of a calculated convolution may include any value in the transformed sequence of numbers. Likewise, an n-dimensional convolution is a function that transforms an original n-dimensional array to a transformed array. The n-dimensional convolution may be defined by an n-dimensional array of scalars (known as the kernel of the n-dimensional convolution). Each particular value in the transformed array may be determined by calculating a linear combination of values in an n-dimensional region of the original array corresponding to the particular value. A result value of a calculated convolution may include any value in the transformed array. In some examples, an image may comprise one or more components (such as color components, depth component, etc.), and each component may include a two dimensional array of pixel values. In one example, calculating a convolution of an image may include calculating a two dimensional convolution on one or more components of the image. In another example, calculating a convolution of an image may include stacking arrays from different components to create a three dimensional array, and calculating a three dimensional convolution on the resulting three dimensional array. In some examples, a video may comprise one or more components (such as color components, depth component, etc.), and each component may include a three dimensional array of pixel values (with two spatial axes and one temporal axis). In one example, calculating a convolution of a video may include calculating a three dimensional convolution on one or more components of the video. In another example, calculating a convolution of a video may include stacking arrays from different components to create a four dimensional array, and calculating a four dimensional convolution on the resulting four dimensional array. In some examples, audio data may comprise one or more channels, and each channel may include a stream or a one-dimensional array of values. In one example, calculating a convolution of audio data may include calculating a one dimensional convolution on one or more channels of the audio data. In another example, calculating a convolution of audio data may include stacking arrays from different channels to create a two dimensional array, and calculating a two dimensional convolution on the resulting two dimensional array.

FIG. 5 is a flowchart of an example process 500 for determining group compliance using surgical guidelines, according to some aspects of the present disclosure. It is to be appreciated that not all steps can be needed to perform the disclosure provided herein. Further, some of the steps can be performed simultaneously, or in a different order than shown in FIG. 5, as will be understood by a person of ordinary skill in the art.

Process 500 can be implemented by devices and systems described in FIGS. 1-4 and using operations caused by computer system 2000. Process 500 can also be understood with reference to FIGS. 6-8. However, process 500 is not limited to these example aspects.

Medical centers or departments may be interested in determining whether a selected group of surgeons, such as those who share a particular specialty, comply with surgical guidelines. Intracorporeal video footage may be analyzed to determine a group compliance level. For example, in some aspects, a non-transitory computer readable medium can contain instructions that, when executed by at least one processor, cause the at least one processor to execute operations to perform intracorporeal video analysis for monitoring compliance with surgical guidelines. In one example, a compliance level (such as the group compliance level, an aggregated compliance level, an individual compliance level of a particular surgeon, a compliance level for a particular surgical procedure, etc.) may be a numerical value. In another example, the compliance level may be a discrete value. In another example, the compliance level may be a continuous numerical value. In yet another example, the compliance level may be on a categorical scale (such as 'High', 'Medium', low', 'None', and so forth).

In 502, a data structure identifying a particular surgical guideline is accessed. For example, at least part of the data structure may be read from memory, may be received from an external computing device (e.g., using a digital communication device), and so forth. The particular surgical guideline may specify a set of actions that are to take place during a particular type of surgical procedure. The data structure may identify a plurality of surgical guidelines, with each surgical guideline specifying a set of actions to take place during a type of surgical procedure. For example, such set of actions may include a single action, at least two actions, between three and five actions, between six and ten actions, more than ten actions, and so forth. In one example, such surgical guideline may further specify one or more actions to be avoided during the respective type of surgical procedure. In one example, the surgical guideline may further indicate, for each action of the set of actions, a level indicative of the importance and/or criticality of the respective action.

Figures 6, 7:
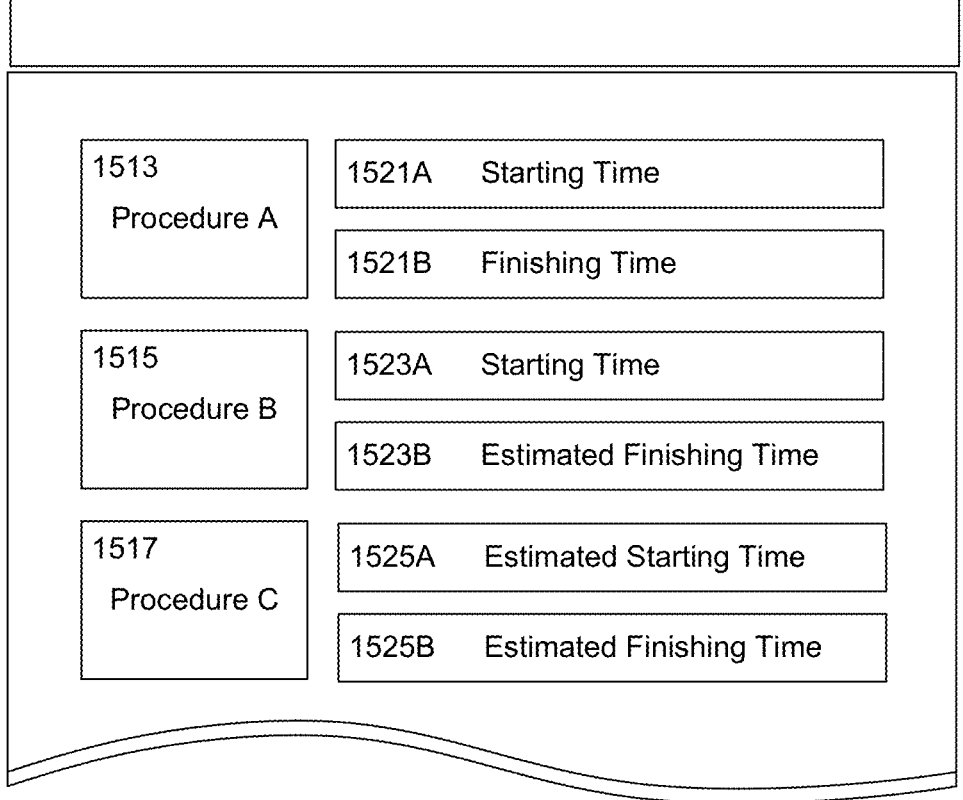
FIG. 6 is an illustration of a surgical guideline, according to some aspects of the present disclosure.
FIG. 7 is an illustration of a schedule of surgical procedures, according to some aspects of the present disclosure.

FIG. 6 illustrates a particular surgical guideline, according to some aspects of the present disclosure. As illustrated, the particular surgical guideline specifies a set of actions, Action 1, Action 2, and Action 3, related to an example surgical procedure, laparoscopic cholecystectomy.

Returning to FIG. 5, in 504, a group of surgeons who performed a plurality of surgical procedures is identified. For example, the group of surgeons can be identified from a memory, from an external computing device (e.g., using a digital communication device), received from a user (e.g., via a user interface), by accessing a database, by accessing a data-structure associating surgical procedures with surgeons who performed the surgical procedures, and so forth. In one example, at least one of the plurality of surgical procedures are of the particular type of surgical procedure described above in relation to 502. In one example, at least two but not all surgeries of the plurality of surgical procedures are of the particular type of surgical procedure described above in relation to 502. In another example, all surgeries of the plurality of surgical procedures are of the particular type of surgical procedure described above in relation to 502. The group of surgeons can represent surgeons who share a particular specialty. A medical specialty is a branch of medical practice that is focused on a defined group of patients, diseases, skills, or philosophy. Examples include those branches of medicine that deal exclusively with children (paediatrics), cancer (oncology), laboratory medicine (pathology), or primary care (family medicine). The group of surgeons can belong to the same entity or can belong to separate entities. For example, the group of surgeons can belong to the same medical institution, or to the same department in the same medical institution.

The plurality of surgical procedures can be understood with reference to FIG. 7. FIG. 7 is an illustration showing an example schedule that may include a listing of procedures such as procedures A-C (e.g., surgical procedures, or any other suitable medical procedures that may be performed in an operating room for which the schedule is used). For each procedure A-C, a corresponding starting and finishing times may be determined. For example, for a past procedure A, a starting time 1521A and a finishing time 1521B may be the actual starting and finishing times. (Since procedure A is completed, the schedule may be automatically updated to reflect actual times). For a current procedure B, a starting time 1523A may be actual and a finishing time 1523B may be estimated (and recorded as an estimated time). Additionally, for procedure C, that is scheduled to be performed in the future, a starting time 1525A and a finishing time 1525B may be estimated and recorded. It should be noted that the schedule is not limited to displaying and/or holding listings of procedures and starting/finishing times for the procedures, but may include various other data of an example surgical procedure Returning to FIG. 5, in 506, a repository of intracorporeal video footage is accessed. A repository may refer to any storage location or set of storage locations where video footage may be stored electronically. For example, the repository may include a memory device, such as a hard drive and/or flash drive. In some aspects, the repository may be a network location such as a server, a cloud storage location, a shared network drive, or any other form of storage accessible over a network. The repository may include a database of surgical video footage captured at various times and/or locations. In some aspects, the repository may store additional data besides the surgical video footage. The repository may be a searchable repository, a sorted repository, an indexed repository, or any other repository as would be appreciated by a person of ordinary skill in the art. The intracorporeal video footage may depict performance of the plurality of surgical procedures by the group of surgeons. The repository of intracorporeal video footage can be understood with reference to FIG. 7, described above.

Figures 8A, 8B, 8C:
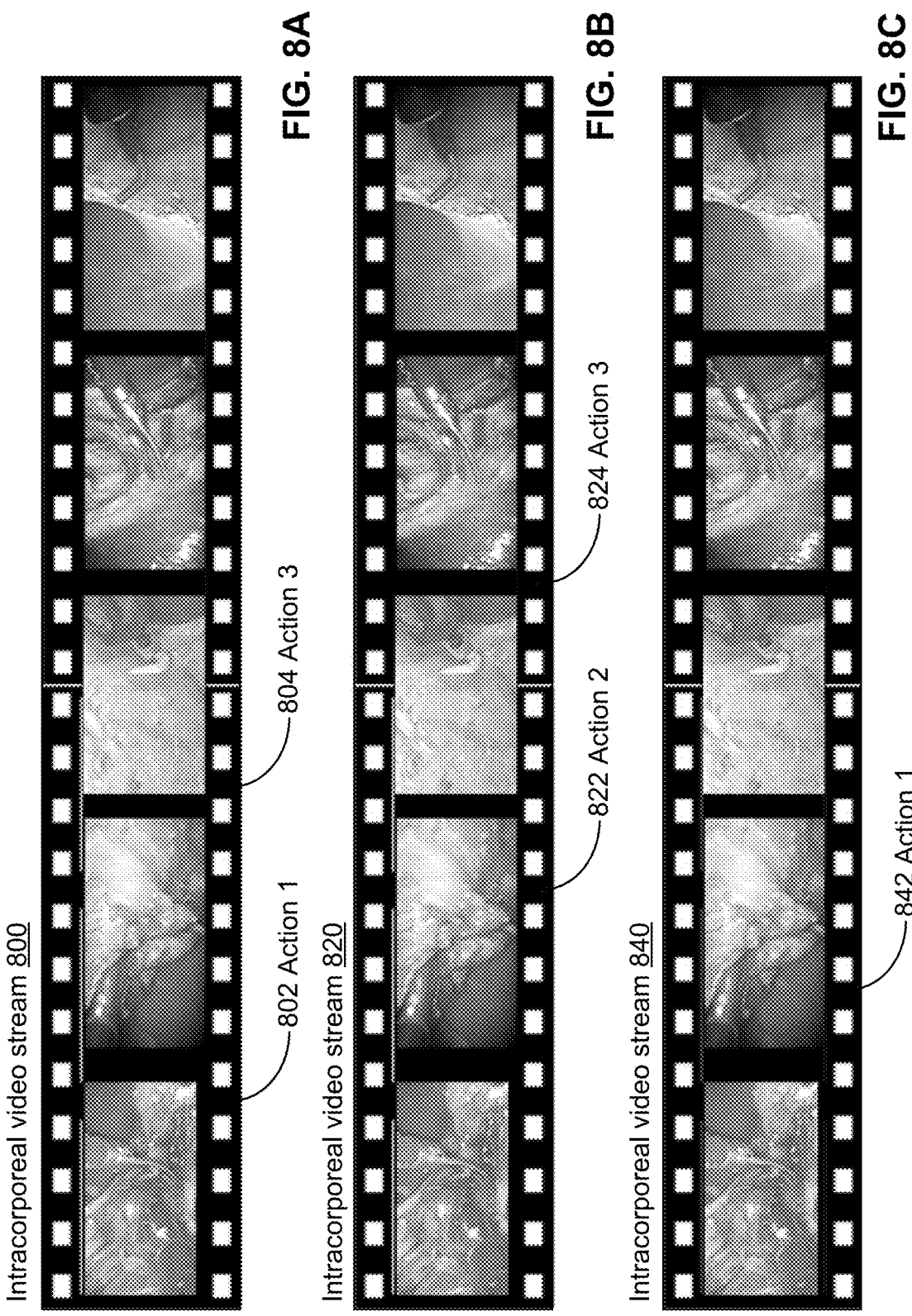
FIGS. 8A-8C are illustrations of intracorporeal video streams, according to some aspects of the present disclosure.

At step 506, repository may be accessed to retrieve footage depicting a type of surgical procedure. For example, with reference to FIGS. 8A-8C, the intracorporeal video footage may depict performance of a laparoscopic cholecystectomy. The intracorporeal video footage depict performance of a laparoscopic cholecystectomy by the group of surgeons identified in step 504. FIGS. 8A-8C are illustrations of intracorporeal video streams, according to some aspects of the present disclosure.

Returning to FIG. 5, in 508, for each surgical procedure of depicted in the video retrieved in step 506, an image analysis is performed on the intracorporeal video footage. Respective intracorporeal video footage can capture respective surgical procedures.

The image analysis is used to determine, at least, whether a respective action from the set of actions specified in the particular surgical guidelines occurred during performance of the respective surgical procedure. In some aspects, a visual action recognition algorithm may be used to analyze the intracorporeal video footage to determine whether a respective action occurred during a respective surgical procedure. Turning back to the example in FIG. 8A-C, FIG. 8A illustrates intracorporeal video stream 800, including action 1 802 and action 3 804. FIG. 8B illustrates intracorporeal video stream 820, including action 2 822 and action 3 824. FIG. 8C illustrates intracorporeal video stream 840, including action 1 842.

To conduct the image analysis, a machine learning model may be trained using training examples to analyze surgical images and/or videos to determine whether particular actions occurred. For example, a sample surgical image and/or a sample surgical video of a sample surgical procedure, together with a label indicating whether a sample action occurred in the sample surgical procedure, can be used as a training example. The trained machine learning model may be used to analyze the intracorporeal video footage to determine whether the respective action occurred during the respective surgical procedure. The machine learning model can also be trained to determine other metrics.

To conduct the image analysis, a convolution of at least part of the intracorporeal video footage may be calculated to obtain a result value of the calculated convolution. Further, determining whether the respective action occurred in the respective surgical procedure may be based on the result value of the calculated convolution of at least part of the intracorporeal video footage. For example, when the result value is a first numerical value, it may be determined that the respective action occurred in the respective surgical procedure, and when the result value is a second numerical value, it may be determined that the respective action did not occur in the respective surgical procedure.

In an aspect, the set of actions can include a first action and a second action. In this aspect, the image analysis can determine whether the first action occurred. Another analysis can then analyze other data, such as non-video data, to determine whether the second action occurred. In another example, analyzing both the image data and the non-video data, for example using a multimodal artificial neural network, may determine whether a particular action included in the set of actions occurred. Accordingly, determining the aggregated compliance level can be based on performing the image analysis and performing an analysis of the non-video data. In some examples, the non-video data may include audio data captured during the surgical procedures. Further, the audio data may be analyzed (for example, using pattern recognition algorithms, using speech recognition algorithms, using speaker diarisation algorithms, etc.) to determine whether the second action occurred. For example, the action may include one medical practitioner informing another medical practitioner of an event (such as an event that occurred, an action that is about to take place, and so forth). In some other examples, the non-video data may include sensor data captured using a sensor included in a medical appliance, such as blood pressure, body temperature, friction, surface tension, electrical impedance, electrical flow, electrical resistance, electrical capacity, and so forth. Further, the sensor data may be analyzed (for example, using a pattern recognition algorithm, using an artificial neural network, etc.) to determine whether the second action occurred. In some other examples, the non-video data may include textual data (such as medical records of patients undergoing the surgeries, postoperative reports, and so forth). Further, the textual data may be analyzed (for example, using Natural Language Processing (NLP) algorithms, using artificial neural networks, etc.) to determine whether the second action occurred. In some other examples, the non-video data may include structured data (for example, from a database, from structured text files, from a data-structure, and so forth). Further, the structured data may be analyzed (for example, by encoding information from fields of the structured data in a vector, and analyzing the vector using a machine learning model) to determine whether the second action occurred.

The second action may include an action that typically occurs during a surgical procedure but is not typically captured in an intracorporeal video footage, such as actions occurring extracorporeal (e.g., actions related to anesthesia, transfusions, administration of drugs, surgical counting, etc.) or actions occurring intracorporeal but outside the field of view of the intracorporeal video footage. In another aspect, the second action may include an action that typically occurs before a surgical procedure, such as a surgeon preparing for a surgery (e.g., reviewing patient information, refreshing on a surgical technique, etc.), preparing the patient (e.g., administrating drugs, performing medical tests, etc.), and so forth. In another aspect, the second action may include an action that typically occurs after a surgical procedure, such as administrating drugs, conducting medical tests, and so forth.

In 510, based on the image analysis from 508, an aggregated compliance level is determined for the group of surgeons. The aggregated compliance level indicates a degree to which the group of surgeons adhered to the particular surgical guideline in performing the plurality of surgical procedures. In one example, in 510, based on the determinations of whether the respective action from the set of actions specified in the particular surgical guideline occurred in the different surgical procedures, the aggregated compliance level of the group of surgeons may be determined.

In some aspects, an aggregated compliance level may be determined based on a statistical function of the compliance levels determined for each surgical procedure of the plurality of surgical procedures. The compliance level of a particular surgical procedure may be a numerical value, a continuous numerical value, a discrete numerical value, a discrete grade (e.g., "Good," "Med.," and "Low"), and so forth. Another example of such aggregated compliance level may include a ratio of occurred actions of a particular surgical procedure for a total set of actions specified in a particular surgical guideline. In one example, the particular surgical guideline may further indicate, for each action, a level indicative of the importance and/or criticality of the respective action, for example as described above in relation to 502. Further, the ratio of occurred actions of a particular surgical procedure for a total set of actions specified in a particular surgical guideline may be a weighted ratio with weights selected based on the levels corresponding to the actions, for example giving higher weight to more important and/or critical actions.

In some aspects, a machine learning model may be trained using training examples to determine a compliance level based on whether actions occurred. An aspect of such training example may include information indicative of whether sample actions occurred in a sample surgical procedure, together with a label indicative of a sample compliance level related to the sample surgical procedure. The trained machine learning model may be used to determine the compliance level for a particular surgical procedure based on whether actions of a set of actions specified in a particular surgical guideline occurred in the particular surgical procedure.

In some aspects, a statistical measure of the determined compliance levels may be calculated to obtain the aggregated compliance level of the group of surgeons. Some non-limiting examples of such statistical measure may include mean, median, mode, or any other statistical function.

In aspects where the data structure identifies a plurality of surgical guidelines, the aggregated compliance level can indicate an overall compliance level of the group of surgeons to each surgical guideline in the plurality of surgical guidelines. Additionally, based on the image analysis from 508, an individual compliance level of a respective surgeon from the group of surgeons can be determined. The individual compliance level can indicate a degree to which the respective surgeon adhered to the particular surgical guideline in performing the plurality of surgical procedures. For example, the individual compliance level may be determined as described above in relation to the aggregated compliance level, when applied for a group of surgeons that includes only the respective surgeon.

In some aspects, the set of actions of 502 may include at least one conditional action to be performed only when a specified situation is encountered. For example, in laparoscopic cholecystectomy, a conditional action may include performing a total cholecystectomy only in cases where a Critical View of Safety is reached. In another example, in laparoscopic cholecystectomy, a conditional action may include performing subtotal cholecystectomy in cases in which the surgeon is unable to achieve a Critical View of Safety. The image analysis of 508 may further determine whether a condition associated with a conditional action was satisfied. For example, the condition may include a successful completion of an action. Further, 510 may increase the aggregated compliance level when the action of a conditional action is performed in surgical procedures where the condition of the conditional action is satisfied. Further, 510 may decrease the aggregated compliance level when the action of a conditional action is performed in surgical procedures where the condition of the conditional action is not satisfied. Further, 510 may decrease the aggregated compliance level when the action of a conditional action is not performed in surgical procedures where the condition of the conditional action is satisfied.

In some aspects, the aggregated compliance level can be determined based in part on a non-video data source. For example, the non-video data source can be data indicating use of a software application, such as a software application designed to guide the surgeon through a checklist for the type of surgery.

In 512, an indicator of the aggregated compliance level is output. For example, the indicator may be stored in memory, may be transmitted to an external computing device, may be presented to an individual (e.g., via a user interface, visually, audibly, textually, graphically, etc.), and so forth. An additional indicator can be output when compliance levels are determined for respective surgeons. The additional indicator can indicate the individual compliance level of the respective surgeon. For example, the indicator and/or the additional indicator may be provided to an individual associated with the group of surgeons, such as a department head, a quality leader, an insurer, and so forth.

In some aspects of process 500, the group of surgeons can be determined as surgeons of a medical institution. Accordingly, the plurality of surgical procedures can be determined as surgeries of a particular type typically performed by the group of surgeons. Records describing the plurality of surgical procedures, such as the intracorporeal video footage, can then be accessed. It is also possible for a second data structure to be accessed. The second data structure can contain universal aggregate data for the particular type of surgery. Then, based on the aggregated compliance level and the universal aggregate data for the particular type of surgery, an institutional deficiency can be identified in a performance factor describing performance (e.g., safety and efficacy) of the particular type of surgery. In this way, a suggested surgical guideline for addressing the institutional deficiency can be provided based on the deficiency and the particular type of surgery. In some aspects, the suggested surgical guidelines can also be based on existing surgical guidelines that the medical institution follows. The suggested surgical guidelines can include a reference medical institution that currently follows the suggested surgical guidelines. Some non-limiting examples of such performance factor may include durations of surgeries, outcomes, readmission rates, costs, and so forth. In some examples, a machine learning model may be trained using training examples to suggest surgical guidelines based on institutional deficiencies and/or based on surgical guidelines that are currently followed and/or based on records associated with surgeries. An example of such training example may include a sample institutional deficiency and/or a sample surgical guideline that is currently followed and/or a sample record associated with a sample surgery, together with a label indicative of a suggested surgical guideline for addressing the sample institutional deficiency. The trained machine learning model may be used to analyze the institutional deficiency and/or other information to determine the suggested surgical guidelines.

Where the group of surgeons belongs to the same entity (such as a medical institution), recommendations and corrective actions for the entity may be determined. In that embodiment, image analysis is performed before and after a recommendation is provided, for example, to determine an improvement as result of the recommendation. First, image analysis is performed on the intracorporeal video footage capturing the respective surgical procedure to detect a first set of intraoperative actions performed during the particular type of surgical procedure. Based on the detected first set of intraoperative actions, a series of video frames can be determined. The determined series of frames depict a failure to comply with a surgical guideline during the particular type of surgical procedure. For example, the intraoperative actions may be detected as described above, for example using a visual action recognition algorithm or a trained machine learning model. In one example, the series of video frames may depict a failure to comply with a surgical guideline by performing a first action before a successful completion of the second action. In this example, the determined series of video frames may include depiction of the first action and the second action showing the first action taking place before the second action. In another example, the series of video frames may depict a failure to comply with a surgical guideline by performing a particular action when it should be avoided based on the status of the patient or the surgery. In this example, the determined series of video frames may include depiction of the particular action. In some examples, a machine learning model may be trained to select frames of a surgical video that depicts a failure to comply with a surgical guideline based on actions detected in the surgical video. An example of such training example may include a sample surgical video of a sample surgery and a sample set of actions performed in the sample surgery, together with a label indicating a sample selection of frames of the sample surgical video that depicts a failure to comply with a particular surgical guideline. The trained machine learning model may be used to analyze the first set of intraoperative actions to determine the series of video frames. Based on the determined series of video frames, a suggested surgical guideline recommendation can be provided to the entity. In some examples, a machine learning model may be trained using training examples to suggest surgical guidelines based on frames of surgical videos. An example of such training example may include sample selected frames of a sample surgical video, together with a label indicating a suggested surgical guideline. The trained machine learning model may be used to analyze the determined series of video frames to select a suggested surgical guideline, and a recommendation for the entity to follow the suggested surgical guideline may be provided. In some examples, the provided recommendation for the entity to follow the suggested surgical guideline may include the determined series of video frames. In some examples, the provided recommendation for the entity to follow the suggested surgical guideline may include information determined based on an analysis of the determined series of video frames.

Then, an image analysis can be performed on a second intracorporeal video footage that is captured after the recommendation. The second intracorporeal video footage depicts performance of the same particular type of surgical procedure as was analyzed before the recommendation. This second image analysis can be used to detect a second set of intraoperative actions. This image analysis can be conducted as described above in relation to the first set of intraoperative actions and the intracorporeal video footage capturing the respective surgical procedure. Based on the detected second set of intraoperative actions, and/or on an analysis of the second intracorporeal video, a subsequent compliance level, with the specific surgical guideline, can be determined. The subsequent compliance level can be determined as described above for step 510.

This subsequent compliance level can be used to initiate a corrective action. The corrective action can be selected such that it is based on more than one subsequent recommendation. In some aspects, the corrective action can include providing a reference video stream demonstrating proper adherence to the selected surgical guideline. In some aspects, the corrective action can include automatic adjustment of an insurance premium of an associated insurance policy. In some aspects, the corrective action can include automatically notifying a supervisor of the group of surgeons or the entity. In some aspects, the corrective action can include providing a reminder to the entity, to remind the group of surgeons to follow the specific surgical guideline during a preparation for a future surgical procedure.

In some aspects of process 500, the plurality of surgical procedures can be divided into subgroups. Then, for each surgical procedure of a particular subgroups, image analysis can be performed on a particular intracorporeal video footage from the repository, where the video footage captures a particular surgical procedure. This analysis can determine a failure type describing a failure to perform a particular action in the particular surgical procedure (continuing the running example, such as a failure to use a Critical View of Safety during a laparoscopic cholecystectomy), where the particular action is included in the set of actions specified in the particular surgical guideline. Using the determined failure types, a statistical measure can be determined, and an additional indicator indicative of the measure can be output. The statistical measure describing occurrence the determined failure types among the identified group of surgeons. In an example, the statistical measure can be a frequency or percentage of times the failure types at a particular medical institution. In some aspects, the failure type can be not attempting an action or can be attempting but not successfully completing the action.

In this way, using the techniques described above with respect to method 500 in FIG. 5, medical centers or departments can determining a degree to which surgeons having a particular specialty comply with surgical guidelines.

In some examples, a data structure identifying a particular surgical guideline specifying a set of actions to take place during a laparoscopic cholecystectomy may be accessed. For example, the surgical guideline illustrated by FIG. 6 may be accessed as described in relation to 502. For example, the set of actions may include 'Use of Critical View of Safety (CVS) technique' (Action 1), 'If the CVS is not achievable, perform a bailout procedure such as subtotal cholecystectomy' (Action 2), and 'Use of at least one of intraoperative cholangiography or laparoscopic ultrasound' (Action 3).

Further, a group of surgeons who performed a plurality of surgical procedures may be identified, for example as described in relation to 504. In one example, at least two but not all surgeries of the plurality of surgical procedures are laparoscopic cholecystectomy. In another example, all surgeries of the plurality of surgical procedures are laparoscopic cholecystectomy. Further, a repository of intracorporeal video footage depicting performance of the plurality of surgical procedures by the group of surgeons may be accessed, for example as described above in relation to 506. Further, for each laparoscopic cholecystectomy of the plurality of surgical procedures, image analysis may be performed on intracorporeal video footage from the repository, where the intracorporeal video footage may capture the respective laparoscopic cholecystectomy. The image analysis may be used to determine at least whether a respective action from the set of actions specified in the particular surgical guideline occurred in the respective laparoscopic cholecystectomy, for example as described above in relation to 508. Further, based on the image analysis and/or based on the determinations of whether the respective action from the set of actions specified in the particular surgical guideline occurred in the different laparoscopic cholecystectomies, an aggregated compliance level of the group of surgeons may be determined, for example as described above in relation to 510. The aggregated compliance level may indicate a degree to which the group of surgeons adhered to the particular surgical guideline in performing the laparoscopic cholecystectomies. Further, an indicator of the aggregated compliance level may be outputted, for example as described above in relation to Step 512.

Medical centers or departments may wish to check compliance with a customized set of guidelines chosen from a larger group of guidelines. For example, if a hospital has unusually high post-operative infection rates, guidelines that impact infection may be selected for analysis. Once selected, the surgical video streams of one or more surgical procedures may be compared with the guidelines. In some aspects, a non-transitory computer readable medium can contain instructions that, when executed by at least one processor, cause the at least one processor to execute operations to perform intracorporeal video analysis operations for monitoring compliance with surgical guidelines.

FIG. 9 is a flowchart of an example process 900 for determining compliance with selected surgical guidelines, according to some aspects of the present disclosure. It is to be appreciated that not all steps can be needed to perform the disclosure provided herein. Further, some of the steps can be performed simultaneously, or in a different order than shown in FIG. 9, as will be understood by a person of ordinary skill in the art.

Process 900 can be implemented by devices, systems, and operations described in FIGS. 1-8 and using operations caused by computer system 2000. Process 900 can also be understood with reference to FIG. 10. However, process 900 is not limited to these example aspects.

In 902, descriptors of a group of surgical guidelines is presented. In one example, the descriptors and/or the group of surgical guidelines may be read from memory, may be received from an external computing device (for example, using a digital communication device), may be received from an individual (for example, via a user interface), may be generated (for example, using a generative machine learning model), and so forth.

A category for each surgical guideline can be presented as at least one descriptor. An example of such category may include importance (such as "Mandatory," "Highly Recommended," "Recommended," and so forth). In another example, the category may relate to an entity related to the guideline (such as an entity enforcing, suggesting, or supporting the guideline). Some other non-limiting examples of such category may include "Safety," "Quality," "Efficiency," and so forth.

Links to medical articles supporting the group of surgical guidelines can be presented as at least one descriptor. Another descriptor can include a predicted effect to comply with for each surgical guideline. For example, the predicted effect can be an intraoperative outcome or a postoperative outcome.

The descriptors may be presented to an individual, may be presented visually, may be presented audibly, may be presented textually, may be presented graphically, or may be presented via a user interface.

FIG. 10 is an illustration of groups of surgical guidelines, including descriptors, according to some aspects of the present disclosure. For example, surgical guidelines can be divided into a "Preoperative" group, a "Surgical events" group, and a "Postoperative" group. In addition, the guidelines include descriptors indicating whether the respective guideline reduces risk of infection.

Returning to FIG. 9, in 904, a selection of a subgroup of surgical guidelines from the group of surgical guidelines is received. The subgroup can include at least one, but not all, of the surgical guidelines from the group of surgical guidelines. The selection may be received from an individual, may be read from a memory, may be received from an external computing device (e.g., using a digital communication device), or may be received via a user interface. In another example, the group of surgical guidelines may be analyzed to select the subgroup of surgical guidelines from the group of surgical guidelines. For example, a machine learning model may be trained using training examples to select a subset of guidelines for a medical entity based on data associated with the medical entity. An example of such training example may include sample data associated with a sample medical entity, together with a label indicating a sample selection of a sample subset of a sample plurality of guidelines. The trained machine learning model may be used to select the subgroup of surgical guidelines from the group of surgical guidelines, for example based on data associated with a particular medical entity. Some non-limiting examples of such data associated with the medical entity may include size of the medical entity, number of surgeries (of a particular type) performed by the medical entity in a selected time period, number of surgeons affiliated with the medical entity, complications in past surgeries performed by the medical entity, medical insurance associated with the medical entity, level of experience of surgeons associated with the medical entity, and so forth. Some non-limiting examples of such medical entity may include a medical center, a department, a group of surgeons working together, and so forth.

As shown in FIG. 10, the groups of surgical procedures can also include a subgroup of surgical guidelines, such as those surgical guidelines aimed at reducing risk of infection. For example, the guidelines of "Preoperative antibiotics in high-risk patients[,]" "Use of critical view of safety (CVS) technique[,]" and "Clipping bile duct[,]" can be selected as a subgroup of surgical guidelines, related to reducing risk of infection, even though they fall under different groups of guidelines. Note that this subgroup of surgical guidelines does not need to include a surgical guideline from all groups (e.g., no guidelines from "Postoperative" are included in the subgroup), and does not need to include all surgical guidelines from a particular group (e.g., some guidelines from "Surgical events" are excluded from the subgroup).

Returning to FIG. 9, in 906, a repository of intracorporeal video streams can be accessed. A repository may refer to any storage location or set of storage locations where video footage may be stored electronically. For example, the repository may include a memory device, such as a hard drive and/or flash drive. In another example, the repository may be controlled in one or more external computing devices, and accessing the repository may include communicating with the one or more external computing devices using a digital communication device. In some aspects, the repository may be a network location such as a server, a cloud storage location, a shared network drive, or any other form of storage accessible over a network. The repository may include a database of surgical video footage captured at various times and/or locations. In some aspects, the repository may store additional data besides the surgical video footage. The repository may be a searchable repository, a sorted repository, an indexed repository, or any other repository as would be appreciated by a person of ordinary skill in the art. The video streams can depict performance, by at least one surgeon, of a plurality of surgical procedures governed by the subgroup of surgical guidelines.

In some aspects, the at least one surgeon can include a plurality of surgeons. In such aspects, 908 and 910 can be repeated for each of the plurality of surgeons.

In 908, for each surgical procedure of the plurality of surgical procedures, an image analysis can be performed on a particular intracorporeal video stream from the repository. The particular intracorporeal video stream can capture a respective surgical procedure. The image analysis can be used to determine whether at least one surgical guideline was followed or complied with. Such image analysis was described above with respect to step 508 in FIG. 5.

In 910, based on the image analysis in 908, an aggregated compliance level can be determined. The aggregated compliance level can indicate compliance, of the at least one surgeon, with the selected subgroup of surgical guidelines. The aggregated compliance level can be determined using a variety of formulas and statistical techniques as was described above with respect to step 510 in FIG. 5.

In some aspects, the plurality of surgical procedures were performed over a period of time, such that the aggregated compliance level reflects an overall compliance of the subgroup of surgical guidelines over that period of time.

In some aspects, the aggregated compliance level can be compared to a threshold to determine whether the surgeon is in violation of policies or guidelines. For example, when an aggregated compliance level is less than a threshold, one or more recommendations for improving compliance of a specific surgical guideline from the subgroup of surgical guidelines can be presented. In one example, the recommendations may be selected as described above.

The subgroup of surgical guidelines can include both guidelines that are not video associated and those that are. For example, turning to FIG. 10, "Preoperative antibiotics" and "Control of postoperative pain" describe actions conducted in support of the surgery that may not be captured in surgical video, while "Use of critical view of safety (CVS) technique" and "Clipping bile duct" may be captured in surgical video. In other examples, the guidelines that are not video associated may include actions conducted while a surgery is ongoing, for example as described above.

In such aspects, the image analysis is performed on the intracorporeal video stream to determine compliance with the video-associated medical guideline. Additionally, at least one record of at least one non-surgical action to support the respective surgical procedure can be retrieved. The at least one non-surgical action can include an action performed before, during or after the respective surgical procedure. The at least one non-surgical action can include at least one of a record keeping action, usage of a monitoring device, preparation, or debrief. Other non-limiting examples of such non-surgical action are described above. This at least one record can be analyzed to determine compliance with the second non-video-associated medical guideline, for example as described above. In this aspect, the aggregated compliance level is determined based on the determined compliance with the first video-associated guideline and the determined compliance with the second non-video-associated guideline.

In 912, an indicator of the aggregated compliance level can be output. For example, the indicator may be stored in memory, may be transmitted to an external computing device, may be presented to an individual (e.g., via a user interface, visually, audibly, textually, graphically, etc.), and so forth. For example, the indicator may be provided to an individual associated with the at least one surgeon, such the at least one surgeon, a manager of the at least one surgeon, a department head, a quality leader, an insurer, and so forth.

In aspects where the subgroup of surgical guidelines includes both guidelines associated with video and those that are not, the indicator can include a first indicator reflecting a compliance level to the first video-associated medical guideline and a second indicator reflecting a compliance level to the non-video-associated medical guideline.

In some aspects of process 900, an image analysis can be performed on a particular intracorporeal video stream from the repository to detect intraoperative actions performed during a particular surgical procedure, for example as described above in relation to process 500. First, image analysis may be performed on the intracorporeal video footage capturing the respective surgical procedure to detect a first set of intraoperative actions performed during the particular surgical procedure. Based on the detected first set of intraoperative actions, a series of video frames can be determined, for example as describe above. The determined series of frames may depict a failure to comply with a particular surgical guideline during the particular surgical procedure. The series of video frames can include at least one detected intraoperative action that took place prior to the failure to comply with the particular surgical guideline. Based on the video frames, a suggested surgical guideline recommendation can be provided to an entity. This determination may be made as described above, for example using a machine learning model. The recommendation may be selected and/or generated as described above in relation to process 500.

Then, an image analysis can be performed on a second intracorporeal video footage that is captured after the recommendation. The second intracorporeal video footage depicts performance of the same particular type of surgical procedure as was analyzed before the recommendation. This second image analysis can be used to detect a second set of intraoperative actions. This image analysis can be conducted as described above. Based on the detected second set of intraoperative actions, a subsequent compliance level, with the specific surgical guideline, can be determined. The subsequent compliance level can be determined as described above. This subsequent compliance level can be used to initiate a corrective action. In some examples, the corrective action may be selected of a plurality of alternative corrective actions, for example based on the recommendation and the subsequent compliance level. In some examples, a textual content aimed to cause an individual to initiate the corrective action may be generated, for example using a Large Language Model (LLM) or other generative models, for example based on the recommendation and the subsequent compliance level. In some examples, a machine learning model may be trained using training examples to select corrective actions based on recommendations and subsequent compliance levels. An example of such training example may include a sample recommendation and a sample subsequent compliance level, together with a label indicating a sample corrective action. The trained machine learning model may be used to analyze the recommendation and the subsequent compliance level to select the corrective action to be initiated. In some examples, corrective action can be selected such that it is based on more than one subsequent recommendation. In some aspects, the corrective action can include providing a reference video stream demonstrating proper adherence to the selected surgical guideline. In some aspects, the corrective action can include automatic adjustment of an insurance premium of an associated insurance policy. In some aspects, the corrective action can include automatically notifying a supervisor of surgeons or the entity. In some aspects, the corrective action can include providing a reminder to the entity, to remind the surgeons to follow the specific surgical guideline during a preparation for a future surgical procedure.

As mentioned above, a specific reference video stream demonstrating adherence to the particular surgical guideline can be selected from the repository. The specific reference video stream can be selected based on one or more characteristics of the particular surgical procedure. For example, the one or more characteristics can be determined as duration, duration of a particular step, complexity level, association with a specific anatomical abnormality, characteristics of the patient undergoing the surgical procedure (e.g., age, gender, blood type, anatomical characteristics, medical condition, etc.), characteristics of the surgeon performing the surgical procedure, and so forth. Additional intracorporeal video streams can also be analyzed to identify other surgical procedures in which the particular surgical guideline was not complied with.

In such aspects of process 900, possible or likely reasons for the failure to comply with the particular surgical guideline can be determined. The failure can be analyzed in view of the other surgical procedures. In some aspects, one or more commonalities among the particular surgical procedure and the other surgical procedures may be identified. For example, a particular action preceding the failure, a common characteristic of the surgical procedures, and so forth, may be identified. Commonalities may be determined, for example, using machine learning, RANdom Sample Consensus (RANSAC) and/or clustering algorithms (such as K-means clustering). The prevalence of each commonality of the one or more commonalities in a second group of surgical procedures in which the particular surgical guideline was complied with may be determined. Any commonality having a low prevalence in the second group may be determined to be a likely reason for the failure.

In other aspects, a plurality of potential reasons may be examined to determine the likely reason for the failure. For example, the intracorporeal video streams of the particular surgical procedure and/or the other surgical procedures may be analyzed to determine whether a particular potential reason is a likely reason for the failure. For example, a machine learning model may be trained using training examples to determine whether a particular potential reason is a likely reason for a failure based on surgical images and/or videos. An example of such training example may include a sample surgical image and/or a sample surgical video of a sample surgical procedure, together with a label indicating whether the particular potential reason is a likely reason for a sample failure in the sample surgical procedure. The trained machine learning model may be used to analyze the intracorporeal video streams of the particular surgical procedure and/or the other surgical procedures to determine whether a particular potential reason is a likely reason for the failure.

Then, the series of video frames depicting the failure to comply with the particular surgical guideline and the specific reference video stream demonstrating adherence to the particular surgical guideline can be output. The series of video frames may be identified by using the image analysis described above to determine when the relevant actions occurred in the video. These video frames and video stream can be presented to a user, via a user interface. The user interface can simultaneously present the outputted video frames and video stream. In some aspects, the simultaneous presentation can be in an aligned timing sequence. In aspects where possible or likely reasons for failure are determined, an indication of the reasons can also be output.

In aspects where the user interface is simultaneously presenting the outputted video frames and video stream, the user interface can be configured to modify at least one of the output series of video frames and the specific reference video stream to match one or more display parameters. For example, at least one of the series of video frames and the specific reference video stream may be transformed so that the two outputs appear substantially from the same angle. In another example, at least one of the series of video frames and the specific reference video stream may be transformed so that the same anatomical structure appears in the same region of the two outputs and/or in the same scale.

In this way, using the techniques descried with respect to FIG. 9, medical centers can check compliance with a customized set of guidelines chosen from a larger group of guidelines.

In some examples, descriptors of a group of surgical guidelines may be presented, for example as illustrated in FIG. 10. Further, a selection of a subgroup of surgical guidelines from the group of surgical guidelines may be received, for example from an individual via a user interface. The subgroup including at least one but not all of the surgical guidelines from the group of surgical guidelines. For example, the subgroup may include 'Use of critical view of safety (CVS) technique' and 'Clipping bile duct'. Further, a repository of intracorporeal video streams depicting performance, by at least one surgeon, of a plurality of surgical procedures governed by the subgroup of surgical guidelines may be accessed. For example, the intracorporeal video streams may depict performance of laparoscopic cholecystectomy by a particular surgeon. Further, for each surgical procedure of the plurality of surgical procedures, image analysis may be performed on an intracorporeal video stream capturing the respective surgical procedure from the repository, for example as described in relation to 908. The image analysis may be used to determine whether at least one surgical guideline was completed. Further, based on the image analysis, an aggregated compliance level indicative of compliance of the particular surgeon with the selected subgroup of surgical guidelines may be determined, for example as described above in relation to 910. Further, an indicator of the aggregated compliance level may be provided, for example to the individual, to the particular surgeon, to a third entity, and so forth.

In an embodiment, physician, medical department or medical institute insurance premiums may be dynamically adjusted based on the level of compliance with surgical guidelines determined through video analysis. This dynamic adjustment can improve reliability and performance of the distributed computer system by reducing the number of computing interactions needed to determine a new insurance premium.

FIG. 11 is a flowchart of an example process 1100 of surgical video analysis for insurance premium adjustment, according to some aspects of the present disclosure. It is to be appreciated that not all steps can be needed to perform the disclosure provided herein. Further, some of the steps can be performed simultaneously, or in a different order than shown in FIG. 11, as will be understood by a person of ordinary skill in the art.

Process 1100 can be implemented by devices, systems, and operations described in FIGS. 1-10 and using operations caused by computer system 2000. However, process 1100 is not limited to these example aspects.

In 1102, a data structure identifying a plurality of surgical guidelines can be accessed. Each surgical guideline of the plurality of surgical guidelines can specify a set of actions to take place during a type of surgical procedure.

The plurality of surgical guidelines can be received, for example, via a selection. For example, the selection may be received from an individual, may be read from a memory, may be received from an external computing device (e.g., using a digital communication device), or may be received via a user interface. In another example, a group of alternative surgical guidelines and/or data associated with a medical entity may be analyzed to select the plurality of surgical guidelines from the group of alternative surgical guidelines. For example, a machine learning model may be trained using training examples to select a subset of guidelines for a medical entity based on data associated with the medical entity. An example of such training example may include sample data associated with a sample medical entity and/or a sample group of alternative guidelines, together with a label indicating a sample selection of a sample subset of a sample plurality of guidelines of the sample group of alternative guidelines. The trained machine learning model may be used to select the plurality of surgical guidelines, for example based on data associated with a selected surgeon (such as the surgeon selected in 1104) and/or data associated with an insurance policy (such as the insurance policy of 1104) and/or a group of alternative guidelines.

In 1104, a selection of a surgeon covered by an original insurance policy can be received. For example, the selection may be received from an individual, may be read from a memory, may be received from an external computing device (e.g., using a digital communication device), or may be received via a user interface.

In 1106, a repository of a plurality of intracorporeal video streams can be accessed. A repository may refer to any storage location or set of storage locations where video footage may be stored electronically. For example, the repository may include a memory device, such as a hard drive and/or flash drive. In some aspects, the repository may be a network location such as a server, a cloud storage location, a shared network drive, or any other form of storage accessible over a network. The repository may include a database of surgical video footage captured at various times and/or locations. In some aspects, the repository may store additional data besides the surgical video footage. The repository may be a searchable repository, a sorted repository, an indexed repository, or any other repository as would be appreciated by a person of ordinary skill in the art. Each intracorporeal video stream can depict a surgical procedure performed by the surgeon.

In 1108, for each of the plurality of intracorporeal video streams, an image analysis can be performed on the respective intracorporeal video stream, for example as described above in relation to 508 and/or 908. The image analysis can be used to determine whether at least one action from the set of actions specified in a surgical guideline occurred. The surgical guideline can govern the surgical procedure depicted in the respective intracorporeal video stream.

In some aspects, for a particular intracorporeal video stream of the plurality of intracorporeal video streams, a convolution of at least part of the particular intracorporeal video stream can be calculated to obtain a result value. Further, the result value can then be used to determine whether the at least one action from the set of actions occurred. For example, when the result value is a first numerical value, it may be determined that a particular action occurred, and when the result value is a second numerical value, it may be determined that the particular action didn't occurred.

In some aspects, for a particular intracorporeal video stream of the plurality of intracorporeal video streams, a machine learning model can be used to analyze the particular intracorporeal video stream. The machine learning model can be used to determine whether the at least one action from the set of actions occurred. For example, the machine learning model may be a machine learning model trained using training examples to determine whether actions occur from intracorporeal video streams. An example of such training example may include a sample intracorporeal video stream, together with a label indicating whether a sample action occurred in the sample intracorporeal video stream.

In 1110, based on the image analysis in 1108, a level of compliance indicating a degree to which the surgeon complied with at least some of the plurality of surgical guidelines can be determined, for example as described above with respect to process 500 and process 900.

The plurality of intracorporeal video streams can depict a plurality of surgical procedures performed during a time period, such that the level of compliance reflects an adherence to the plurality of surgical guidelines during that time period. Additionally, a data structure including a reference compliance level can be accessed. This reference compliance level can reflect an adherence to the plurality of surgical guidelines during a previous time period. Further, the adjustment to the insurance premium may be based on a difference between the aggregated compliance level and the reference compliance level. For example, an amount of the adjustment to the insurance premium may be a function of the difference between the aggregated compliance level and the reference compliance level. Some non-limiting examples of such function may include a linear function, a non-linear function, a polynomial function, an exponential function, a continuous function, a discontinuous function, and so forth. In another example, a limitation may be added to and/or removed from the insurance policy based on the difference between the aggregated compliance level and the reference compliance level.

The original insurance policy can cover a plurality of surgeons. In this aspect, 1106-1110 can be repeated for each of the plurality of surgeons. Accordingly, an aggregated compliance level can be determined based on the level of compliance for each of the plurality of surgeons.

In 1112, information based on the level of compliance can be output. This output can enable a determination of an adjustment to an insurance premium of the original insurance policy. For example, outputting the information based on the level of compliance may include presenting the information based on the level of compliance to an individual to enable the individual to adjust the insurance premium, for example via a user interface. In another example, outputting the information based on the level of compliance may include transmitting a digital signal encoding the information based on the level of compliance to an external computing device to enable the external computing device to adjust the insurance premium, for example using a digital communication device. In yet another example, outputting the information based on the level of compliance may include storing the information based on the level of compliance in a digital memory to enable other software processes and/or algorithms to access the information based on the level of compliance and adjust the insurance premium. The adjustment to the insurance premium can be by an amount that is based on the determined level of compliance of the surgeon. For example, the adjustment to the insurance premium can be by an amount that is a function of the determined level of compliance of the surgeon. Some non-limiting examples of such function may include a linear function, a non-linear function, a polynomial function, an exponential function, a continuous function, a discontinuous function, and so forth. An indication of the adjustment can also be provided as an output. A condition of the adjustment can also be determined based on the plurality of intracorporeal video streams and an indication of the condition can be output. An example of the adjustment may be, for instance, that the adjustment may be valid as long as the surgeon works no longer than 11 hours a day or does not perform surgeries of a particular type, and so forth. For example, when the plurality of intracorporeal video streams shows the surgeon is at higher risk when using a specific surgical technique, the condition may be that the surgeon does not use the specific surgical technique. In one example, a machine learning model may be trained using training examples to determine conditions for an insurance policy based on intracorporeal video streams. An example of such training example, may include sample intracorporeal video streams, together with a label indicating a sample selection of conditions for a sample insurance policy. The trained machine learning model may be used to analyze the plurality of intracorporeal video streams to determine the condition of the adjustment.

The adjustment to the insurance premium can be based on the determined level of compliance and one or more other metrics. For example, the one or more other metrics can include complexity levels of the surgical procedures depicted in the plurality of intracorporeal video streams and/or characteristics of a patient undergoing a surgical procedure (e.g., weight, age, mobility, medical conditions, etc.) depicted in one of the plurality of intracorporeal video streams. In another example, the one or more other metrics can include characteristics of a medical equipment used in a surgical procedure (e.g., use of a correct or incorrect type of equipment, use of a specific equipment configuration, use of a specific equipment attachment, etc.) depicted in one of the plurality of intracorporeal video streams or on practitioners other than the selected surgeon performing or otherwise involved with the surgical procedures depicted in the plurality of intracorporeal video streams. In yet another example, the one or more other metrics can be a temporal trend. The temporal trend indicates the degree to which the surgeon has complied with at least some of the plurality of surgical guidelines has changed over time (e.g., whether they are improving in conformance to the guidelines, etc.). In a further example, the one or more other metrics can include a likely reason for the failure to comply with a particular surgical guideline during a particular surgical procedure. In another example, the one or more other metrics can be a failure type related to a failure to comply with a particular surgical guideline during a particular surgical procedure. In some examples, a machine learning model may be trained using training examples to determine adjustment to the insurance premium based on a level of compliance and/or one or more other metrics. An example of such training example may include a sample level of compliance and/or sample additional data, together with a label indicative of a sample adjustment to a sample insurance premium. The trained machine learning model may be used to analyze the determined level of compliance and/or the one or more other metrics to determine the adjustment to the insurance premium.

In aspects involving a plurality of surgeons and an aggregated compliance level, the aggregated compliance level can be output to enable the determination of the adjustment to the insurance premium.

In aspects involving a reference compliance level, the determination of the adjustment to the insurance premium can be based on a difference between the aggregated compliance level and the reference compliance level.

In some aspects, the level of compliance may only be output when the difference between the determined level of compliance and a historic level of compliance is above a selected threshold value.

In some examples, 1110 may include determining, based on the image analysis in 1108, that the surgeon complied with a particular surgical guideline of the plurality of surgical guidelines in a first subset of the plurality of intracorporeal video streams, and that the surgeon failed to comply with the particular surgical guideline in a second subset of the plurality of intracorporeal video streams. Further, a temporal relation between the first and second subsets of the plurality of intracorporeal video streams may be determined. Some non-limiting examples of such temporal relation may include all the intracorporeal video streams of the first subset precede all the intracorporeal video streams of the second subset, at least one of the intracorporeal video streams of the first subset precedes all the intracorporeal video streams of the second subset, all the intracorporeal video streams of the first subset precede at least one of the intracorporeal video streams of the second subset, at least one of the intracorporeal video streams of the first subset precedes at least one of the intracorporeal video streams of the second subset, all the intracorporeal video streams of the second subset precede all the intracorporeal video streams of the first subset, at least one of the intracorporeal video streams of the second subset precedes all the intracorporeal video streams of the first subset, all the intracorporeal video streams of the second subset precede at least one of the intracorporeal video streams of the first subset, at least one of the intracorporeal video streams of the second subset precede at least one of the intracorporeal video streams of the first subset, and so forth. Further, the adjustment to the insurance premium of the original insurance policy may be determined based on the temporal relation between the first and second subsets of the plurality of intracorporeal video streams. For example, when the temporal relation is a first relation, the adjustment may be a first adjustment, and when the temporal relation is a second relation, the adjustment may be a second adjustment.

The second adjustment may differ from the first adjustment. In another example, when all the intracorporeal video streams of the second subset precede all the intracorporeal video streams of the first subset, the adjustment may be a first adjustment, and when all the intracorporeal video streams of the first subset precede all the intracorporeal video streams of the second subset, the adjustment may be a second adjustment. The second adjustment may differ from the first adjustment.

Medical malpractice occurs when a medical or health care professional, through a negligent act or omission, deviates from standards in their profession, thereby causing injury or death to a patient. The negligence might arise from errors in diagnosis, treatment, aftercare or health management. Surgeons are usually required to carry insurance to protect surgeons from bearing the full cost of defending against a negligence claim made by a patient, and damages awarded in such a civil lawsuit. When a patient alleges medical malpractice, an insurance provider must assess the patient's allegations to determine whether they have sufficient merit to warrant a settlement or other compensation.

Embodiments expedite processing of medical malpractice claims. In an embodiment, a malpractice claim may be analyzed to identify, in a video corresponding to the claim, a video portion relevant to resolving the claim. In some aspects, a non-transitory computer readable medium can contain instructions that, when executed by at least one processor, cause the at least one processor to execute operations to perform intracorporeal video analysis using a medical malpractice claim.

FIG. 12 is a flowchart of an example process 1200 for correlating a medical malpractice claim with a portion of a video, according to some aspects of the present disclosure. It is to be appreciated that not all steps can be needed to perform the disclosure provided herein. Further, some of the steps can be performed simultaneously, or in a different order than shown in FIG. 12, as will be understood by a person of ordinary skill in the art.

Process 1200 can be implemented by devices, systems, and operations described in FIGS. 1-11 and using operations caused by computer system 2000. Process 1200 can also be understood with reference to FIGS. 13-14. However, process 1200 is not limited to these example aspects.

In 1202, a medical malpractice claim alleging damage from a particular surgical procedure is received. For example, the medical malpractice claim may be read from memory, may be received from an external computing device (e.g., using a digital communication device), may be received from an individual (e.g., through a user interface), may be obtained by analyzing an image of at least one page with an Optical Character Recognition algorithm, may be obtained from a database, and so forth.

FIG. 13 a flowchart 1300 depicting an example medical malpractice claim 1302. As depicted, medical malpractice claim 1302 alleges that a surgeon performed gall bladder removal surgery negligently.

Returning to FIG. 12, in 1204, a linguistic analysis is performed on the medical malpractice claim. The linguistic analysis is used to identify a surgical event giving rise to the medical malpractice claim. In one example, the linguistic analysis may be based on operative language used in the medical malpractice claim. In one example, the linguistic analysis may be conducted using a natural language processing such as bag of words, probabilistic context-free grammar, or a Large Language Model. In one example, a machine learning model may be trained using training examples to identify surgical events giving rise to medical malpractice claims based on textual content of the medical malpractice claims. An example of such training example may include a sample textual content of a sample medical malpractice claim, together with a label indicative of a sample surgical event giving rise to the sample medical malpractice claim. The trained machine learning model may be used to analyze the medical malpractice claim and identify the surgical event giving rise to the medical malpractice claim.

In some aspects, the surgical event can be a failure to perform a required intracorporeal action or can be a manner of performing a required intracorporeal action.

Flowchart 1300 of FIG. 13 shows an example linguistic analysis 1304 performed on medical malpractice claim 1302. This linguistic analysis can be performed as described for 1204, and can be used to identify a surgical event 1306. For example, when linguistic analysis 1304 is performed on medical malpractice claim 1302, it is identified that a bile duct was damaged. Further, damaging a bile duct is known to be associated with clipping, cutting and/or transecting a ductal structure. Therefore, clipping, cutting and/or transecting a ductal structure is identified as surgical event 1306. Surgical event 1306 can then be used throughout subsequent operations.

Returning to FIG. 12, in 1206, an intracorporeal video stream depicting the particular surgical procedure is accessed. For example, the intracorporeal video stream may be read from memory, may be received from an external computing device (e.g., using a digital communication device), may be captured using an image sensor, may be obtain from a repository (for example, as described above), and so forth.

Figure 14:
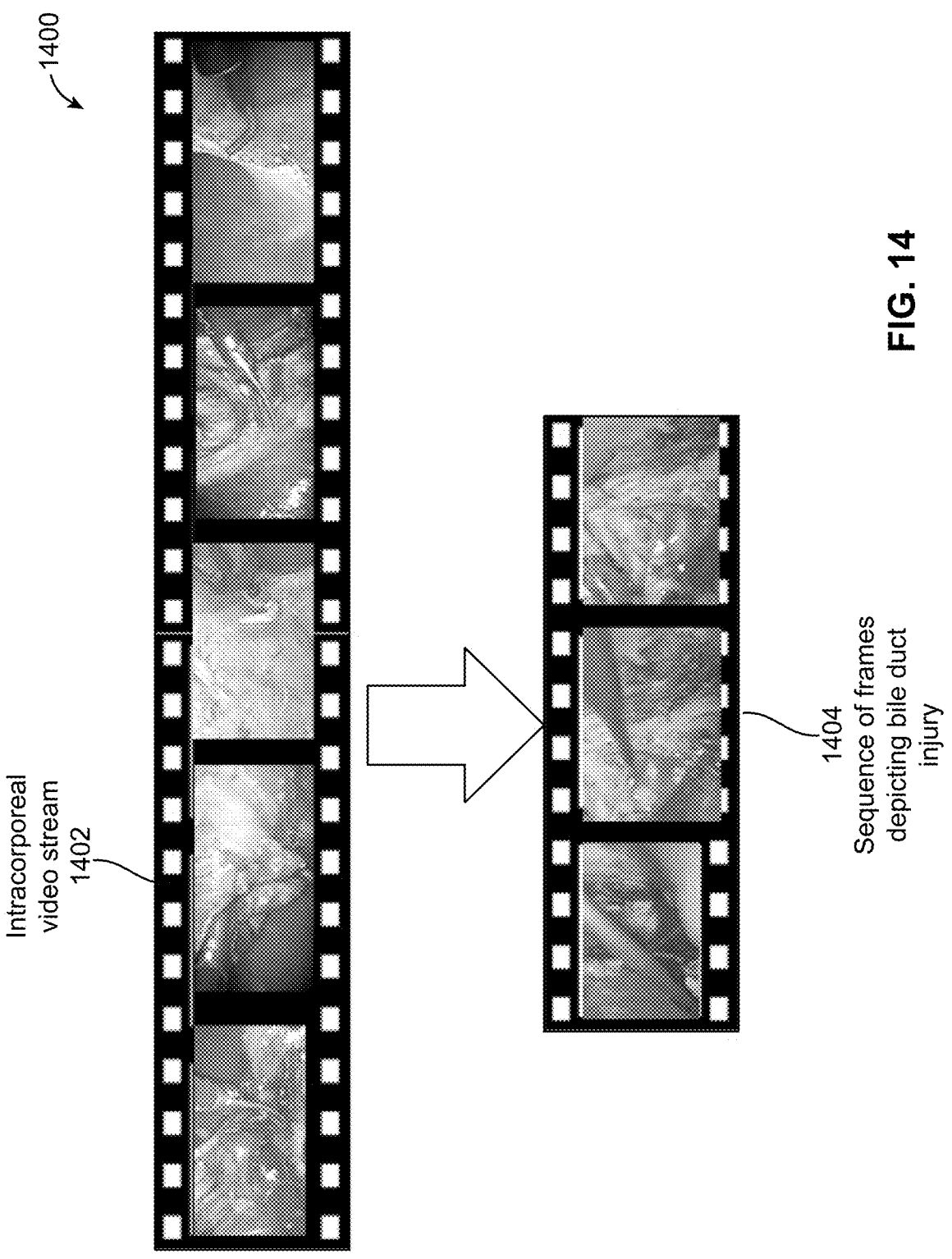
FIG. 14 is an illustration of intracorporeal video streams, according to some aspects of the present disclosure.

FIG. 14 is an illustration 1400 of intracorporeal video streams, according to some aspects of the present disclosure. Illustration 1400 includes an intracorporeal video stream 1402.

Returning to FIG. 12, in 1208, based on the identified surgical event in 1204, the intracorporeal video stream is analyzed to identify a series of frames from the intracorporeal video stream that depicts the surgical event. In another example, textual content of the medical malpractice claim and the intracorporeal video stream may be analyzed (for example, using a multimodal model) to identify a series of frames from the intracorporeal video stream that depicts a surgical event associated with the medical malpractice claim.

In some aspects, a machine learning model may be trained using training examples to identify the series of frames corresponding to surgical events in videos based on surgical events and/or operative language and/or other information. An example of such training example may include a sample surgical event and/or a sample operative language and/or a sample other information corresponding to the sample surgical event, and a sample surgical video, together with a label indicating frames of the sample surgical video that corresponds to the sample surgical event. In one example, the trained machine learning model may be used to analyze the intracorporeal video stream based on the identified surgical event and/or the identified operative language and/or the other information to identify the series of frames from the intracorporeal video stream that depicts the surgical event. In another example, the trained machine learning model may be used to analyze textual content of the medical malpractice claim and the intracorporeal video to identify the series of frames from the intracorporeal video stream that depicts a surgical event associated with the medical malpractice claim.

In some examples, a convolution of at least part of the intracorporeal video stream may be calculated to obtain a result value. Further, based on the identified surgical event and the result value, it may be determined whether to include a particular frame of the intracorporeal video stream in the series of frames from the intracorporeal video stream that depicts the surgical event. In one example, the at least part of the intracorporeal video stream may be at least part of the particular frame of the intracorporeal video stream. In one example, when the identified surgical event is a particular event and the result value is a first numerical value, the particular frame may be included in the series of frames, and when the identified surgical event is the particular event and the result value is a second numerical value, the particular frame may be excluded from the series of frames. In another example, the textual content of the medical malpractice claim may be analyzed to determine a mathematical object, for example using an NLP algorithm or a text embedding algorithm. Further, based on the mathematical object and the result value, it may be determined whether to include a particular frame of the intracorporeal video stream in the series of frames from the intracorporeal video stream that depicts the surgical event. For example, when the mathematical object is a particular numerical value and the result value is a first numerical value, the particular frame may be included in the series of frames, and when the numerical value is the particular numerical value and the result value is a second numerical value, the particular frame may be excluded from the series of frames. In another example, when the mathematical object is a first numerical value and the result value is a particular numerical value, the particular frame may be included in the series of frames, and when the numerical value is a second numerical value and the result value is the particular numerical value, the particular frame may be excluded from the series of frames. In yet another example, when the mathematical object is a first numerical value and the result value is a second numerical value, the particular frame may be included in the series of frames, and when the numerical value is a third numerical value and the result value is a fourth numerical value, the particular frame may be excluded from the series of frames.

In some aspects, a video search query is determined based on the reimbursement code and/or the identified surgical event. Accordingly, the analysis in 1208 uses the video search query to search in the intracorporeal video stream for the series of frames corresponding to the surgical event. For example, the video search query may include a short video depicting the identified surgical event in a different surgical procedure, and searching using the video search query may include searching the intracorporeal video stream for frames similar to the frames of the short video. In another example, the video search query may include an indication of one or more elements of the identified surgical event, such as medical equipment or anatomical structure, and searching using the video search query may include searching the intracorporeal video stream for frames depicting the one or more elements. In yet another example, the video search query may include an indication of a portion of the intracorporeal video stream (e.g., the portion between two other events depicted in the intracorporeal video stream), and searching using the video search query may include searching only for frames in the portion of the intracorporeal video stream. In one example, a data-structure associating reimbursement codes and/or surgical events with video search queries may be accessed based on the reimbursement code and/or the identified surgical event to obtain the video search query. In another example, a machine learning model may be trained using training examples to generate video search queries based on reimbursement codes and/or surgical events. An example of such training example may include a sample reimbursement code and/or a sample surgical event, together with a sample video search query. The trained machine learning model may be used to analyze the reimbursement code and/or the identified surgical event to generate the video search query.

In some aspects, a second series of frames depicting a prerequisite to the surgical event can be output and used in subsequent operations. For example, when the surgical event is clipping and/or cutting an anatomical structure, the prerequisite may include reaching CVS before the clipping and/or cutting the anatomical structure. In one example, the prerequisite may be determined based on the surgical event. For example, a data-structure associating surgical events with prerequisites may be accessed based on the identified surgical event to determine the prerequisite. In one example, the prerequisite may be determined based on the surgical event and the medical malpractice claim. For example, a data-structure associating surgical events and/or medical malpractice claims with prerequisite may be accessed based on the surgical event and/or the medical malpractice claim to determine the prerequisite. In one example, the medical malpractice claim may indicate a damage to a bile duct, the surgical event may be clipping and/or cutting an anatomical structure, and the prerequisite may be a prerequisite known to reduce the risk of damage to the bile duct in clipping and/or cutting an anatomical structure, such as reaching CVS. In one example, the second series of frames depicting the determined prerequisite may be identified by analyzing the intracorporeal video stream using a machine learning model. The machine learning model may be a machine learning model trained using training examples. An example of such training example may include a sample prerequisite and a sample surgical video, together with a label indicating a series of frames from the sample surgical video depicting the sample prerequisite.

With reference to illustration 1400 of FIG. 14, a series of frames 1404 from intracorporeal video stream 1402 can be identified based on, for example, surgical event 1306 of FIG. 3. For example, it can be determined that series of frames 1404 depicts bile duct damage.

Returning to FIG. 12, in 1210, based on the identified series of frames in 1208, an action corresponding to the medical malpractice claim is initiated.

In some aspects, the action includes providing an indication whether a correlation exists between the series of frames and the medical malpractice claim. In one example, the series of frames may be analyzed to determine whether a correlation exists between the series of frames and the medical malpractice claim. For example, a machine learning model may be trained using training examples to determine whether correlations exist between surgical footage and medical malpractice claims. An example of such training example may include a sample surgical footage and a sample medical malpractice claim, together with a label indicative of whether a correlation exists between the sample surgical footage and the sample medical malpractice claim. The trained machine learning model may be used to analyze the series of frames and the medical malpractice claim to determine whether a correlation exists between the series of frames and the medical malpractice claim.

In some aspects, the action includes automatically determining whether a basis exists for the medical malpractice claim. In one example, the series of frames may be analyzed to determine whether a basis exists for the medical malpractice claim. For example, a machine learning model may be trained using training examples to determine whether a basis exists for medical malpractices claims from surgical footage. An example of such training example may include a sample surgical footage and a sample medical malpractice claim, together with a label indicative of whether a basis exists for the sample medical malpractice claim. The trained machine learning model may be used to analyze the series of frames and the medical malpractice claim to determine whether a basis exists for the medical malpractice claim.

In other aspects, the action includes transmitting the series of frames to an entity for consideration. For example, the series of frames may be transmitted to an external computing device associated with the entity using a digital communication device. In some aspects, the action may include presenting the series of frames to an individual for consideration. For example, the series of frames may be presented via a user interface, using a display screen, using an extended reality appliance, and so forth.

When the action is initiated, a recommendation related to the medical malpractice claim can be determined and the recommendation can be output. In one example, the recommendation may be determined based on an analysis of the medical malpractice claim and/or on an analysis the intracorporeal video stream depicting the particular surgical procedure and/or on an analysis of the identified series of frames from the intracorporeal video stream. In some examples, a machine learning model may be trained using training examples to generate recommendation related to medical malpractice claims based on the medical malpractice claims and/or surgical footage. An example of such training example may include a sample medical malpractice claim and a sample surgical footage, together with a sample recommendation related to the sample medical malpractice claim. The trained machine learning model may be used to analyze the medical malpractice claim and/or the intracorporeal video stream depicting the particular surgical procedure and/or the identified series of frames from the intracorporeal video stream to generate the recommendation. In some examples, a convolution of at least part of the intracorporeal video stream or at least part of the series of frames may be calculated to obtain a result value. Further, the recommendation may be generated based on the result value. For example, a function of the result value may be used as an input to a generative model (such as an LLM) to generate the recommendation.

The recommendation can be determined by accessing a textual medical record related to the medical malpractice claim, where the recommendation is based on the textual medical record. The textual medical record can be, for example, at least one of a postoperative report of the particular surgical procedure or an electronic medical record of a patient on who the particular surgical procedure was performed. For example, the textual medical record may be analyzed to determine a mathematical object, for example using text embedding algorithm, and the mathematical object may be used to generate the recommendation. For example, a function of the mathematical object may be used as an input to a generative model (such as an LLM) to generate the recommendation. Determining the recommendation can also be based on a time elapsed since the particular surgical procedure, a patient treated by the particular surgical procedure (e.g., a patient's age, medical condition, etc.), or a surgeon performing the particular surgical procedure. In some examples, the recommendation may be based on information related to the medical malpractice claim, such as any combination of an analysis of the medical malpractice claim and/or an analysis of the textual medical record related to the medical malpractice claim and/or an analysis of the intracorporeal video stream depicting the particular surgical procedure and/or the time elapsed since the particular surgical procedure and/or the patient treated by the particular surgical procedure and/or the surgeon performing the particular surgical procedure and/or whether the surgeon is currently affiliated with the medical facility where the particular surgical procedure was performed. For example, a machine learning model may be trained using training examples to generate recommendation related to medical malpractice claims based on such information associated with the medical malpractice claims. An example of such training example may include a sample information associated with a sample medical malpractice claim, together with a sample recommendation related to the sample medical malpractice claim. The trained machine learning model may be used to generate the recommendation based on any combination of the medical malpractice claim and/or the textual medical record related to the medical malpractice claim and/or the intracorporeal video stream depicting the particular surgical procedure and/or the time elapsed since the particular surgical procedure and/or the patient treated by the particular surgical procedure and/or the surgeon performing the particular surgical procedure and/or whether the surgeon is currently affiliated with the medical facility where the particular surgical procedure was performed. For example, a machine learning model may be trained using training examples to generate recommendation related to medical malpractice claims based on such information associated with the medical malpractice claims.

In some aspects, determining the recommendations can include analyzing the intracorporeal video stream and the textual medical record based on the medical malpractice claim to determine a likelihood that a complication alleged in the medical malpractice claim is a result of an error made during the particular surgical procedure. In these aspects, the recommendation can be based on the determined likelihood. For example, a multimodal regression model may be used to analyze the intracorporeal video stream and/or the textual medical record and/or the medical malpractice claim to determine the likelihood that the complication alleged in the medical malpractice claim is the result of the error made during the particular surgical procedure. In one example, the multimodal regression model may be a machine learning model trained using training examples. An example of such training example may include a sample intracorporeal video stream depicting a sample surgical procedure and/or a sample textual medical record associated with the sample surgical procedure and/or a sample medical malpractice claim associated with the sample surgical procedure to determine the likelihood that a sample complication alleged in the sample medical malpractice claim is a result of an error made during the sample surgical procedure.

The particular surgical procedure can be performed at a medical facility, and the recommendation can be determined based on the medical facility the surgeon was affiliated with at the time of the particular surgical procedure, for example using a machine learning model as described above. In these aspects, determining the recommendation can also be based on whether the surgeon is currently affiliated with the medical facility.

In some examples, the recommendation can be a recommendation related to a decision whether or not to settle the medical malpractice claim. For example, a machine learning model may be trained using training examples to determine whether to recommend to settle medical malpractice claims based on information associated with the medical malpractice claims. Such information associated with the medical malpractice claims are described above. An example of such training example may include information associated with a sample medical malpractice claim, together with a sample recommendation on whether or not to settle the sample medical malpractice claim.

In some examples, the recommendation may include an indication of expected litigation costs associated with a prospective litigation of the medical malpractice claim. For example, a multimodal regression model may be used to analyze information associated with the medical malpractice claim to determine the expected litigation costs associated with the prospective litigation of the medical malpractice claim. Such information associated with the medical malpractice claims are described above. In one example, the multimodal regression model may be a machine learning model trained using training examples. An example of such training example may include sample information associated with a sample medical malpractice claim, together with a label indicating expected litigation costs associated with prospective litigation of the sample medical malpractice claim.

In some examples, the recommendation may include an indication of a predicted likelihood of success associated with a prospective litigation of the medical malpractice claim. For example, a multimodal regression model may be used to analyze information associated with the medical malpractice claim to determine the predicted likelihood of success associated with the prospective litigation of the medical malpractice claim. Such information associated with the medical malpractice claims are described above. In one example, the multimodal regression model may be a machine learning model trained using training examples. An example of such training example may include sample information associated with a sample medical malpractice claim, together with a label indicating a predicted likelihood of success associated with prospective litigation of the sample medical malpractice claim.

In some examples, the recommendation may include an indication a predicted compensation associated with a prospective lawsuit associated with the medical malpractice claim. For example, a multimodal regression model may be used to analyze information associated with the medical malpractice claim to determine the predicted compensation associated with the successful lawsuit associated with the medical malpractice claim. Such information associated with the medical malpractice claims are described above. In one example, the multimodal regression model may be a machine learning model trained using training examples. An example of such training example may include sample information associated with a sample medical malpractice claim, together with a label indicating a predicted compensation associated with a successful lawsuit associated with the sample medical malpractice claim.

In this way, video can be quickly determined to speed processing of medical malpractice claims.

Health insurance or medical insurance is a type of insurance that covers the whole or a part of the risk of a person incurring medical expenses. Medical expenses are often described in payment and billing contexts using standard claim codes. Some non-limiting examples of claim code sets may include the Current Procedural Terminology (CPT), Level II HCPCS, ICD9, ICD10, and so forth.

To obtain full reimbursement for all medical procedures, surgeons or other medical entities may be required to include codes in their bills for each surgical event in a procedure for which insurance reimbursement is sought. When questions arise about whether the codes are accurate, proof may be required. Intracorporeal video footage may be analyzed to detect reimbursable events, and image data demonstrating that the reimbursable surgical event actually occurred may be output. In some aspects, a non-transitory computer readable medium can contain instructions that, when executed by at least one processor, cause the at least one processor to execute operations to perform intracorporeal video analysis for identifying image data depicting a reimbursable event.

In addition to using video to expedite processing of medical malpractice claims, embodiments may expedite processing of medical insurance claims. To expedite processing of medical insurance claims, a medical claim code may be analyzed to identify, in a video corresponding to the claim, a video portion relevant to resolving the claim. In some aspects, a non-transitory computer readable medium can contain instructions that, when executed by at least one processor, cause the at least one processor to execute operations to perform intracorporeal video analysis using a medical insurance claim.

FIG. 15 is a flowchart of an example process for correlating a medical claim code with a portion of a video, according to some aspects of the present disclosure. It is to be appreciated that not all steps can be needed to perform the disclosure provided herein. Further, some of the steps can be performed simultaneously, or in a different order than shown in FIG. 15, as will be understood by a person of ordinary skill in the art.

Process 1500 can be implemented by devices, systems, and operations described in FIGS. 1-14 and using operations caused by computer system 2000. Process 1500 can also be understood with reference to FIG. 16. However, process 1500 is not limited to these example aspects.

In 1502, a medical insurance claim is received. The medical insurance claim arises from a particular surgical procedure. For example, the medical insurance claim may be read from memory, may be received from an external computing device (e.g., using a digital communication device), may be received from an individual (e.g., through a user interface), may be obtained by analyzing an image of at least one page with an Optical Character Recognition algorithm, may be obtained from a database, and so forth.

In 1504, a reimbursement code from the medical insurance claim is accessed. A reimbursement code can be a standardized code determined for every respective feature of every respective surgical procedure. Additional, a reimbursement code can be a standardized code determined for every respective piece of equipment used in every respective surgical procedure.

Figure 16:
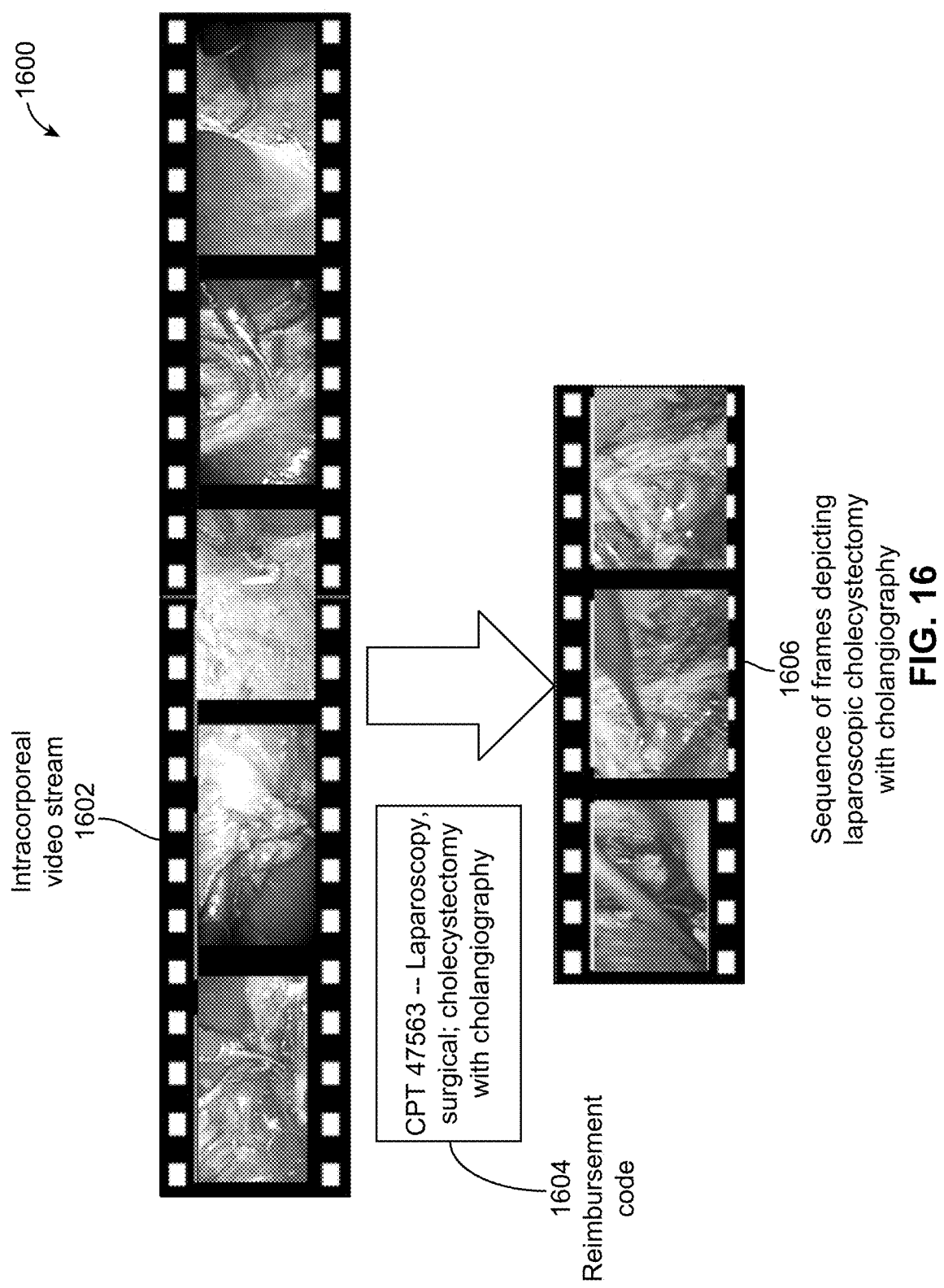
FIG. 16 is an illustration of an example process for correlating a medical claim code with a portion of a video, according to some aspects of the present disclosure.

FIG. 16 is an illustration of an example process 1600 for correlating a medical claim code 1604 with a portion of a video 1606, according to some aspects of the present disclosure. As shown in process 1600, a reimbursement code can be, for example, reimbursement code 1604. Reimbursement code 1604 can correspond to a medical insurance claim. In this example, reimbursement code 1604 is directed towards laparoscopic surgery and cholecystectomy with cholangiography.

Returning to FIG. 15, in 1506, an intracorporeal video stream depicting the particular surgical procedure is accessed. For example, the intracorporeal video stream may be read from memory, may be received from an external computing device (e.g., using a digital communication device), may be captured using an image sensor, may be accessed in a repository as described above, and so forth. In one example, at the time of accessing the intracorporeal video stream depicting the particular surgical procedure, the particular surgical procedure may be completed or in progress.

Process 1600 illustrates an example intracorporeal video stream as intracorporeal video stream 1602.

Returning to FIG. 15, in 1508, based on the reimbursement code from 1504, the intracorporeal video stream is analyzed to identify a series of frames from the intracorporeal video stream. The series of frames depicts a surgical event related to the reimbursement code. In some examples, a machine learning model may be trained using training examples to identify frames depicting events in videos based on reimbursement codes. An example of such training example may include a sample surgical video and a sample reimbursement code, together with a label indicating a sample selection of frames depicting events associated with the sample reimbursement code in the sample surgical video. The trained machine learning model may be used to analyze the reimbursement code from 1504 and the intracorporeal video stream to identify the series of frames from the intracorporeal video stream. In some examples, a data-structure associating reimbursement codes with surgical events may be accessed based on the reimbursement code from 1504 to determine a particular surgical event. Further, the intracorporeal video stream may be analyzed to identify particular frames from the intracorporeal video stream depicting the particular surgical event, and the particular frames may be included in the identified series of frames. In some examples, a convolution of at least part of a particular frame of the intracorporeal video stream may be calculated to obtain a result value. Further, based on the result value, it may be determined whether to include the particular frame in the identified series of frames. In one example, when the result value is a first numerical value, the particular frame may be included in the identified series of frames, and when the result value is a second numerical value, the particular frame may be excluded from the identified series of frames. In another example, a threshold may be selected based on the reimbursement code from 1504, the particular frame may be included in the identified series of frames when the result value is above the selected threshold, and the particular frame may be excluded from the identified series of frames when the result value is below the selected threshold.

In some aspects, a video search query is determined based on the reimbursement code. Accordingly, the analysis in 1508 uses the video search query to search in the intracorporeal video stream for the series of frames corresponding to the surgical event. For example, the video search query may include a short video depicting the surgical event in a different surgical procedure, and searching using the video search query may include searching the intracorporeal video stream for frames similar to the frames of the short video. In another example, the video search query may include an indication of one or more elements of the surgical event, such as medical equipment or anatomical structure, and searching using the video search query may include searching the intracorporeal video stream for frames depicting the one or more elements. In yet another example, the video search query may include an indication of a portion of the intracorporeal video stream (e.g., the portion between two other events depicted in the intracorporeal video stream), and searching using the video search query may include searching only for frames in the portion of the intracorporeal video stream.

In some aspects, a second series of frames depicting a prerequisite to the surgical event can be output and used in subsequent operations. In one example, the prerequisite may be determined based on the surgical event and/or the medical insurance claim and/or the reimbursement code. For example, a data-structure associating surgical events and/or medical insurance claims and/or reimbursement codes with prerequisites may be accessed based on the surgical event and/or the medical insurance claim and/or the reimbursement code to determine the prerequisite. In one example, the reimbursement code may indicate a laparoscopic cholecystectomy, the surgical event may be clipping and/or cutting an anatomical structure, and the prerequisite may be a prerequisite known to reduce the risk of damage to the bile duct in clipping and/or cutting an anatomical structure, such as reaching CVS. In one example, the second series of frames depicting the determined prerequisite may be identified by analyzing the intracorporeal video stream using a machine learning model. The machine learning model may be a machine learning model trained using training examples. An example of such training example may include a sample prerequisite and a sample surgical video, together with a label indicating a series of frames from the sample surgical video depicting the sample prerequisite.

As shown in process 1600, intracorporeal video stream 1602 can be analyzed based on reimbursement code 1604, directed towards laparoscopy and cholecystectomy. Accordingly, a series of frames 1606 can be identified from intracorporeal video stream 1602. The series of frames 1606 is only a portion of video stream 1602, and depict the surgical event of a laparoscopic cholecystectomy with cholangiography.

Returning to FIG. 15, in 1510, based on the identified series of frames from 1508, an action is initiated that corresponds to the medical insurance claim from 1502.

In some aspects, the action can include providing an indication of whether a reimbursable correlation exists between the series of frames and the reimbursement code. For example, a machine learning model may be trained using training examples to determine whether reimbursable correlation exists between surgical footage and reimbursement codes. An example of such training example may include a sample series of frames and a sample reimbursement code, together with a label indicating whether there is a reimbursable correlation between the sample series of frames and the sample reimbursement code. Further, the machine learning model may be used to analyze the series of frames and the reimbursement code to determine whether a reimbursable correlation exists between the series of frames and the reimbursement code.

In some aspects, the action can include determining whether a basis exists for the medical insurance claim. For example, a machine learning model may be trained using training examples to determine whether a basis exists for medical insurance claims in surgical footage. An example of such training example may include a sample medical insurance claim and a sample series of frames, together with a label indicating whether a basis exists for the sample medical insurance claim in the sample series of frames. The trained machine learning model may be used to analyze the medical insurance claim and the series of frames to determine whether a basis exists for the medical insurance claim.

In some aspects, the action can include transmitting (for example, using a digital communication device) the series of frames from 1508 to an entity for consideration. Some non-limiting examples of such entity may include an insurer, a medical coding auditor, a medical coder, an accounting department, and so forth. In other examples, the action may include presenting the series of frames from 1508 to an individual for consideration. For example, the series of frames may be presented via a user interface, using a display screen, using an extended reality appliance, and so forth.

When the action is initiated, a recommendation related to the medical insurance claim can be determined and the recommendation can be output. In one example, the recommendation may include a recommendation to accept the medical insurance claim. In another example, the recommendation may include a recommendation to reject the medical insurance claim. In yet another example, the recommendation may include a recommendation to conduct additional investigation related to the medical insurance claim. In yet another example, the recommendation may include a recommendation to modify the reimbursement code in the medical insurance claim and/or to add another reimbursement code to the medical insurance claim and/or to remove the reimbursement code from the medical insurance claim.

In some aspects, the recommendation can be determined by accessing a textual medical record of the medical insurance claim, where the recommendation is based on the textual medical record. The textual medical record can be, for example, a postoperative report of the particular surgical procedure or an electronic medical record of a patient on who the particular surgical procedure was performed. For example, the textual medical record may be analyzed using a Large Language Model to generate the recommendation. In another example, a multimodal model may be used to analyze the textual medical record and the intracorporeal video stream to generate the recommendation.

In some aspects, the recommendation can be based on an analysis of the intracorporeal video stream. For example, a convolution of at least part of the intracorporeal video stream can be calculated to obtain a result value, where the result value is used to determine the recommendation. In another example, a machine learning model can be used to analyze the intracorporeal video stream to determine the recommendation. The machine learning model can be trained similarly to the model described with reference to FIG. 12. In another example, an LLM may be used to analyze the medical insurance claim and the textual medical record to generate the recommendation.

In some aspects, the recommendation can include a recommendation to add an additional reimbursement code to the medical insurance claim. Then, the intracorporeal video stream can be analyzed to select the additional reimbursement code. In other aspects, the recommendation can include a recommendation to substitute the reimbursement code with an alternative reimbursement code to the medical insurance claim. Then, the intracorporeal video stream can be analyzed to select the alternative reimbursement code.

In some aspects, the reimbursement code can include a first reimbursement code and a second reimbursement code. If a recommendation is determined, then the recommendation can include a first recommendation related to the first reimbursement code and a second recommendation related to the second reimbursement code. In these aspects, the second recommendation differs from the first recommendation. For example, the first recommendation can be a recommendation to remove the first reimbursement code from the medical insurance claim. In another example, the first recommendation can be a recommendation to deny reimbursements from the first reimbursement code. In this example, the second recommendation can be a recommendation to approve reimbursements from the second reimbursement code.

As mentioned above, to obtain full reimbursement for all medical procedures, surgeons may be required to include codes in their bills for each surgical event in a procedure for which insurance reimbursement is sought. Identifying which codes are needed can be tedious and error prone. Embodiments provide computer readable mediums, methods and systems to automatically determine insurance codes from video by identifying the tools used in the video.

FIG. 17 is a flowchart of an example process for analyzing surgical video to support insurance reimbursement, according to some aspects of the present disclosure. It is to be appreciated that not all steps can be needed to perform the disclosure provided herein. Further, some of the steps can be performed simultaneously, or in a different order than shown in FIG. 17, as will be understood by a person of ordinary skill in the art.

Process 1700 can be implemented by devices, systems, and operations described in FIGS. 1-16 and using operations caused by computer system 2000. Process 1700 can also be understood with reference to FIG. 18. However, process 1700 is not limited to these example aspects.

In 1702, intracorporeal video footage captured during a surgical procedure on a patient is accessed. For example, the intracorporeal video footage may be read from memory, may be received from an external computing device (e.g., using a digital communication device), may be captured using at least one image sensor, may be accessed in a repository as described above, and so forth. In one example, at the time of accessing the intracorporeal video footage, the particular surgical procedure may be completed or in progress.

Figure 18:
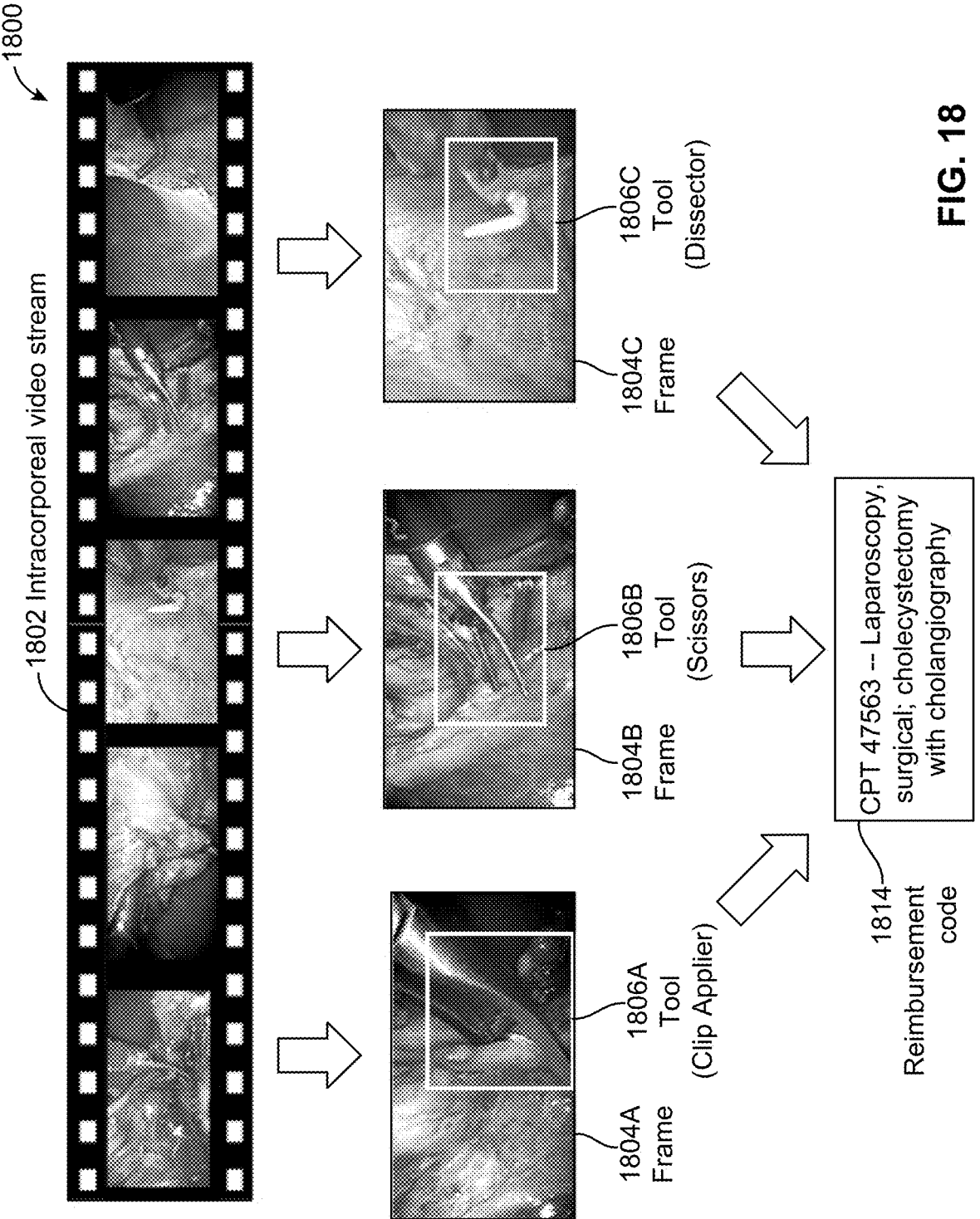
FIG. 18 is an illustration of an example process for analyzing surgical video to support insurance reimbursement, according to some aspects of the present disclosure.

FIG. 18 is an illustration of an example process 1800 for analyzing surgical video to support insurance reimbursement, according to some aspects of the present disclosure. As shown, process 1800 includes intracorporeal video stream 1802. Intracorporeal video stream 1802 can be the video footage accessed in 1702.

In 1704, the intracorporeal video footage is analyzed to detect a surgical tool. Computer vision may be used to identify one or more medical instruments used in a surgical procedure. Object detection/recognition is a computer vision technique that allows us to identify and locate objects in an image or video. With this kind of identification and localization, object detection can be used to count objects in a scene and determine and track their precise locations, all while accurately labeling them. An example object detection algorithm is the Viola-Jones algorithm. In one example, a convolution of at least part of the intracorporeal video footage may be calculated to obtain a result value. Further, the detection of the surgical tool may be based on the result value. For example, when the result value is a first numerical value, the surgical tool may be detected, and when the result value is a second numerical value, no surgical tool may be detected. In another example, when the result value is a first numerical value, a surgical tool of a first type may be detected, and when the result value is a second numerical value, a surgical tool of a second type may be detected. The second type may differ from the first type.

Process 1800 depicts the analysis of intracorporeal video stream 1802. For example, intracorporeal video stream 1802 can be analyzed for various surgical tools, such as a clip applier (i.e., tool 1806A), scissors (i.e., tool 1806B), or a dissector (i.e., tool 1806C).

In 1706, the intracorporeal video footage is analyzed to detect a reimbursable event associated with the surgical tool from 1704 within the intracorporeal video footage. In one example, a convolution of at least part of the intracorporeal video footage may be calculated to obtain a result value. Further, the detection of the reimbursable event may be based on the result value. For example, when the result value is a first result value, the reimbursable event may be detected, and when the result value is a second result value, no reimbursable event may be detected. In another example, when the result value is a first result value, a first reimbursable event may be detected, and when the result value is a second result value, a second reimbursable event may be detected. The second reimbursable event may differ from the first reimbursable event.

Frames of the intracorporeal video footage may be analyzed to detect a reimbursable event, such as a reimbursable event associated with a surgical tool. For example, a machine learning model may be trained using training examples to detect reimbursable events (such as reimbursable events associated with surgical tools) in images and/or videos. An example of such training example may include a sample intracorporeal image or video depicting a sample surgical tool, together with a label indicating a reimbursable event associated with the sample surgical tool in the sample intracorporeal image or video, a label indicating a frame or a portion of the sample intracorporeal image or video representative of the reimbursable event in the sample intracorporeal image or video, and/or a label indicating a medical reimbursement code corresponding to the reimbursable event in the sample intracorporeal image or video. The trained machine learning model may be used to analyze the intracorporeal video footage and detect the reimbursable event within the intracorporeal video footage. At least one frame of the intracorporeal video footage representative of the detected reimbursable event may be identified, for example using the same machine learning model. In some examples, the at least one representative frame may be extracted from the intracorporeal video footage.

Based on identification of the medical instrument, a particular reimbursable event may be identified at a location in the video footage corresponding to the medical instrument. Here, a location may refer to one or more frames in which the medical instrument appears and/or to portions of the frames depicting the medical instrument or surrounding the depiction of the medical instrument. For example, a scalpel or other instrument may indicate that an incision is being made and a marker identifying the incision may be included in the timeline at this location. In some aspects, anatomical structures may be identified in the video footage using the computer analysis. For example, the disclosed methods may include identifying organs, tissues, fluids or other structures of the patient to determine a reimbursable event. In some aspects, a reimbursable event may be determined based on an interaction between a medical instrument and the anatomical structure. For example, visual action recognition algorithms may be used to analyze the video and detect the interactions between the medical instrument and the anatomical structure. Other examples of features that may be used to determine a reimbursable event may include, motions of a surgeon or other medical professional, patient characteristics, surgeon characteristics or characteristics of other medical professionals, sequences of operations being performed, timings of operations or events, characteristics of anatomical structures, or medical conditions.

The detected reimbursable event can be or be based on at least one of a type of medical procedure that took place during the surgical procedure, or a complication that took place during the surgical procedure. In one example, the type of medical procedure that took place during the surgical procedure may be determined by analyzing the intracorporeal video footage using a visual classification algorithm to one of a plurality classes, where each class corresponds to a type of medical procedures, thereby determining the type of medical procedure that took place during the surgical procedure. In one example, the complication may be detected by analyzing the intracorporeal video footage. For example, a machine learning model may be trained using training examples to detect complications in surgical footage. An example of such training example may include a sample surgical footage, together with a label indicating whether the sample surgical footage depicts a complication and/or the type of the complication. The trained machine learning model may be used to analyze the intracorporeal video footage to detect the complication.

In some examples, the detected reimbursable event can be or include a surgical action performed in the surgical procedure, using a particular surgical tool (such as the surgical tool from 1704). In one example, the surgical action may be detected by analyzing the intracorporeal video footage using a visual action recognition algorithm. In some aspects, a surgical action can be at least one of removing material, stitching material, stopping blood flow, restarting blood flow, stitching, etc.

In some examples, the detected reimbursable event can include an interaction between the surgical tool and an anatomical structure of the patient. Some non-limiting examples of such interaction may include a physical contact between the surgical tool and the anatomical structure, a force applied by or via the surgical tool on the anatomical structure, a manipulation on the anatomical structure performed by or using the surgical tool, an interaction that is part of a surgical action, and so forth. For example, the interaction between the surgical tool and the anatomical structure may be detected by analyzing the intracorporeal video footage. For example, a region of a frame of the intracorporeal video footage depicting the surgical tool may be identified (for example, using semantic segmentation algorithm), a region of the frame of the intracorporeal video footage depicting the anatomical structure may be identified (for example, using semantic segmentation algorithm), and the interaction may be detected based on a distance between the two regions and/or the relative orientation between the two regions.

Process 1800 depicts analysis of intracorporeal video stream 1802. For example, intracorporeal video stream 1802 can be analyzed to detect reimbursable events corresponding to surgical tools, such as a clip applier (i.e., tool 1806A), scissors (i.e., tool 1806B), or a dissector (i.e., tool 1806C). The events can be those depicted in frame 1804A, frame 1804B, and frame 1804C, where frame 1804A depicts use of tool 1806A, frame 1804B depicts use of tool 1806B, and frame 1804C depicts use of tool 1806C.

Returning to FIG. 17, in 1708, based on the surgical tool from 1704, a medical reimbursement code related to the detected reimbursable event from 1706 is determined. The medical reimbursement code can be a universal medical alphanumeric code. In some aspects, the medical reimbursement code can be determined using the same machine learning model from 1706. The trained machine learning model may be used to analyze the intracorporeal video footage and determine the medical reimbursement code related to the detected reimbursable event. In some aspects, a data-structure associating surgical tools with medical reimbursement codes may be accessed based on the surgical tool from 1704 to determine the medical reimbursement code related to the detected reimbursable event. In one example, the data-structure may identify a plurality of alternative medical reimbursement codes related to the surgical tool from 1704. Further, the intracorporeal video footage may be analyzed to select the medical reimbursement code related to the detected reimbursable event of the plurality of alternative medical reimbursement codes. For example, a convolution of at least part of the intracorporeal video footage may be may be calculated to obtain a result value. Further, the selection of the medical reimbursement code related to the detected reimbursable event of the plurality of alternative medical reimbursement codes may be based on the result value. In one example, when the result value is a first numerical value, the medical reimbursement code related to the detected reimbursable event may be a first medical reimbursement code of the plurality of alternative medical reimbursement codes, and when the result value is a second numerical value, the medical reimbursement code related to the detected reimbursable event may be a second medical reimbursement code of the plurality of alternative medical reimbursement codes. The second medical reimbursement code may differ from the first medical reimbursement code. In some examples, the selection of the medical reimbursement code related to the detected reimbursable event of the plurality of alternative medical reimbursement codes may be based on at least one of a type of medical procedure that took place during the surgical procedure, a complication that took place during the surgical procedure, a surgical action performed in the surgical procedure, or an interaction between the surgical tool and an anatomical structure of the patient.

In some aspects, the medical reimbursement code can be based on a type of medical procedure that took place during the surgical procedure, a complication that took place during the surgical procedure, a surgical action performed in the surgical procedure, or an interaction between the surgical tool and an anatomical structure of the patient.

In aspects involving an interaction between the surgical tool and an anatomical structure of the patient, the intracorporeal video footage can be analyzed to detect the anatomical structure, for example using a visual object detection algorithm. The intracorporeal video footage can also be analyzed to determine a type of the interaction between the surgical tool and the anatomical structure. For example, a visual classification algorithm may be used to analyze the intracorporeal video footage and classify the interaction to one of a plurality of classes, where each class may correspond to a type of interaction, and thereby the type of the interaction may be determined. Further, this type can be used when determining the medical reimbursement code. For example, when the type of the interaction is a first type, the medical reimbursement code may be determined to be a first code, and when the type of the interaction is a second type, the medical reimbursement code may be determined to be a second code. The second code may differ from the first code.

In some aspects, the intracorporeal video footage can be analyzed to detect multiple anatomical structures. For example, a first anatomical structure and a second anatomical structure. For example, the anatomical structures may be detected by analyzing the intracorporeal video footage using a visual object detection algorithm. The first anatomical structure and the second anatomical structure can be different portions of a same organ of the patient, or different organs of the patient. Then, the intracorporeal video footage can be analyzed to detect multiple interactions, for example as described above. For example, a first interaction can be detected as an interaction between the surgical tool and the first anatomical structure. A second interaction can also be detected as an interaction between the surgical tool and the second anatomical structure. The determination of the medical reimbursement code can then be based, at least partially, on whether the first interaction precedes the second interaction in the surgical procedure. For example, when the first interaction precedes the second interaction in the surgical procedure, the medical reimbursement code may be determined to be a first code, and when the second interaction precedes the first interaction in the surgical procedure, the medical reimbursement code may be determined to be a second code. The second code may differ from the first code.

In some aspects, the intracorporeal video footage can be analyzed to detect a second surgical tool, for example as described above in relation to 1704. In one example, the reimbursable event may correspond to a surgical action performed by, or at least involving, both the surgical tool and the second surgical tool. The determination of the medical reimbursement code can then be based, at least partially, on the second surgical tool. For example a data-structure associating pairs of surgical tools with medical reimbursement codes may be accessed based on the surgical tool and the second surgical tool to determine the medical reimbursement code.

In some aspects, pre-procedure information related to the surgical procedure can be accessed. The pre-procedure information can be information available before a beginning of the surgical procedure. For example, the pre-procedure information may be read from memory, may be accessed in a database, may be accessed via an external computing device (for example, using a digital communication device), and so forth. Some non-limiting examples of such pre-procedure information may include medical records of the patient, surgical planning data, medical images of the patient, and so forth. Based on this pre-procedure information, the intracorporeal video footage can be analyzed to identify an elevated complexity of the surgical procedure. An elevated complexity can be elevated compared to a most likely complexity based on the pre-procedure information alone. In some aspects, a multimodal model may be used to analyze the intracorporeal video footage and the pre-procedure information to identify the elevated complexity of the surgical procedure compared to a most likely complexity based on the pre-procedure information alone. In some aspects, the intracorporeal video footage can be analyzed to detect an anatomical structure of the patient and to classify the anatomical structure, for example using an object recognition algorithm. This classification of the anatomical structure can be used to identify the elevated complexity of the surgical procedure. For example, a data-structure associating abnormal anatomical structures with elevated complexity may be accessed based on the classification of the anatomical structure to identify the elevated complexity of the surgical procedure. In some examples, the intracorporeal video footage can also be analyzed to identify a relationship among two or more anatomical structures of a patient. For example, regions depicting the two anatomical structures may be detected in the intracorporeal video footage using a semantic segmentation algorithm, and a distance and/or orientation of the two regions may be used to identify the relationship among two or more anatomical structures of the patient. The identified relationship can also be used to identify the elevated complexity of the surgical procedure. For example, when the distance between the two anatomical structures is below a selected threshold, the elevated complexity of the surgical procedure may be identified. In another example, when the orientation between the two anatomical structures is a particular orientation, the elevated complexity of the surgical procedure may be identified. Determination of the medical reimbursement code can be based, at least partially, on the identified elevated complexity. For example, when an elevated complexity is identified, the medical reimbursement code may be determined to be a first code, and when no elevated complexity is identified, the medical reimbursement code may be determined to be a second code. The second code may differ from the first code.

In some aspects, the intracorporeal video footage can be analyzed to determine a level of complexity of the surgical procedure. Accordingly, the determination of the medical reimbursement code can be further based on the level of complexity. For example when the level of complexity is a first level, a first medical reimbursement code may be determined, and when the level of complexity is a second level, a second medical reimbursement code may be determined. The second medical reimbursement code may differ from the first medical reimbursement code. In some examples, a machine learning model may be trained using training examples to determine levels of complexity of surgical procedures from surgical footage. An example of such training example may include a sample surgical footage capturing a sample surgical procedure, together with a label indicative of a complexity level of the sample surgical procedure. The trained machine learning model may be used to analyze the intracorporeal video footage to determine the level of complexity of the surgical procedure.

In some aspects, a summary can be generated for the surgical procedure. The summary can include an indication of the medical reimbursement code. In some examples, the summary may be a textual summary in a natural language. For example, a Large Language Model may be used to generate the textual summary based on at least one of the medical reimbursement code, a textual record associated with the surgical procedure (such as a textual medical record related to the patient), the patient, a surgeon performing the surgical procedure, or information determined based on an analysis of the intracorporeal video footage. In some examples, the summary may be a visual summary. For example, frames of the intracorporeal video footage may be selected (for example, as described above) and aggregated to generate the visual summary.

As shown in process 1800, a medical reimbursement code 1814 can be determined based on the events depicted in frame 1804A, frame 1804B, and frame 1804C. For example, based on use of tool 1806A (i.e., clip applier on an anatomical structure), use of tool 1806B (i.e., scissors on an anatomical structure), and use of tool 1806C (i.e., dissector on an anatomical structure), reimbursement code 1814 can be a reimbursement code related to a laparoscopic surgery of cholecystectomy with cholangiography.

Returning to FIG. 17, in 1710, the medical reimbursement code is output. For example, the medical reimbursement code and/or the at least one frame representative of the reimbursable event may be stored in memory, may be stored in a database, may be stored in a data-structure, may be transmitted to an external computing device (e.g., using a digital communication device), may be presented to an individual (e.g., via a user interface, using a display screen, using an extended reality appliance, etc.), and so forth. In one example, the medical reimbursement code may be provided to an insurer, to a medical coding auditor, to a medical coder, to an accounting department, and so forth.

In some aspects, at least one frame of the intracorporeal video footage is identified, for example as described above. The at least one frame can be representative of the detected reimbursable event. The at least one frame can be a single frame, can be multiple frames, can include a plurality of sequential or non-sequential frames, or can include a video clip. Then, the at least one of representative frame from the intracorporeal video footage can be extracted. The at least one representative frame can be output, for example as described above.

In some aspects, the intracorporeal video footage can also be analyzed to determine a level of compliance with one or more guidelines, for example as described above. For example, to determine a level of compliance with a surgical guideline. Accordingly, an indicator of the level of compliance can be output. For example, the level of compliance may be provided with the medical reimbursement code and/or the at least one frame representative of the reimbursable event.

FIG. 19 is a flowchart of an example process for analyzing surgical videos to identify a billing coding mismatch, according to some aspects of the present disclosure. It is to be appreciated that not all steps can be needed to perform the disclosure provided herein. Further, some of the steps can be performed simultaneously, or in a different order than shown in FIG. 19, as will be understood by a person of ordinary skill in the art.

Process 1900 can be implemented by devices, systems, and operations described in FIGS. 1-18 and using operations caused by computer system 2000. However, process 1900 is not limited to these example aspects.

Video analysis may be used to check whether surgical reimbursement claims are properly coded. After a surgery is coded for reimbursement, video analysis may determine whether the codes are correct, and if not, provide a notification. In some aspects, a non-transitory computer readable medium can contain instructions that, when executed by at least one processor, cause the at least one processor to execute operations to identify a billing coding mismatch.

In 1902, a medical reimbursement code associated with a surgical procedure is received. For example, the medical reimbursement code may be read from memory, may be received from an external computing device (e.g., using a digital communication device), may be received from an individual (e.g., using a user interface), may be generated automatically (for example, using 1700, based on an analysis of a post-operative report using an NLP algorithm, etc.), and so forth. In one example, the medical reimbursement code may be a medical reimbursement code from a medical insurance claim associated with the surgical procedure. In some other examples, 1902 may comprise receiving a medical reimbursement code associated with a surgical event within a surgical procedure.

In 1904, surgical video of the surgical procedure is received. For example, the surgical video may be read from memory, may be received from an external computing device (e.g., using a digital communication device), may be captured using at least one image sensor, and so forth. In one example, the surgical video may be an intracorporeal surgical video captured using an image sensor positioned within a body of a patient.

In 1906, image analysis is performed on the surgical video from 1904 to determine whether a match exists between the medical reimbursement code from 1902 and the surgical video.

The image analysis may be performed by analyzing the surgical video to determine a level of complexity of the surgical procedure, for example as described above. The image analysis can also include determining whether an alleged reimbursable event corresponding to the medical reimbursement code took place in the surgical procedure based on the determined level of complexity. For example, when the level of complexity is a first level, it may be determined that a match exists between the medical reimbursement code and the surgical video, and when the level of complexity is a second level, it may be determined that no match exists between the medical reimbursement code and the surgical video.

In some aspects, the image analysis is performed by analyzing the surgical video to determine a level of guideline compliance during the surgical procedure, for example as described above. The image analysis can also include determining whether an alleged reimbursable event corresponding to the medical reimbursement code took place in the surgical procedure based on the determined level of guideline compliance. For example, when the level of guideline compliance is a first level, it may be determined that the alleged reimbursable event took place in the surgical procedure, and when the level of guideline compliance is a second level, it may be determined that the alleged reimbursable event did not take place in the surgical procedure.

In some examples, a medical record of the patient can be accessed. For example, the medical record may be read from memory, may be received from an external computing device (for example, using a digital communication device), may be accessed in an Electronic Medical Record system, and so forth. Further, it can then be determined whether an alleged reimbursable event, corresponding to the medical reimbursement code, took place in the surgical procedure based on the medical record of the patient. For example, a binary NLP classification algorithm may be used to analyze the medical record of the patient and classify it to one of two classes, where one class may correspond to the alleged reimbursable event took place in the surgical procedure and the other class may correspond to the alleged reimbursable event did not take place in the surgical procedure. In another example, a binary multimodal classification algorithm may analyze the medical reimbursement code, the surgical video from 1904 and text from the medical record of the patient to classify the three to one of two classes, where one class may correspond to a match exists between the medical reimbursement code and the surgical video, and the other class may correspond to no match exists between the medical reimbursement code and the surgical video.

In some examples, an audio recording captured during the surgical procedure can be accessed. For example, the audio recording may be read from memory, may be received from an external computing device (for example, using a digital communication device), may be captured using an audio sensor during the surgical procedure, and so forth. Further, it can then be determined whether an alleged reimbursable event, corresponding to the medical reimbursement code, took place in the surgical procedure based on the medical record of the patient and/or the audio recording. For example, the audio recording may be analyzed using a speech recognition algorithm to obtain textual content, and a binary NLP classification algorithm may be used to analyze the textual content and classify it to one of two classes, where one class may correspond to the alleged reimbursable event took place in the surgical procedure and the other class may correspond to the alleged reimbursable event did not take place in the surgical procedure. In another example, a binary multimodal classification algorithm may analyze the medical reimbursement code, the surgical video from 1904 and text from the audio recording to classify the three to one of two classes, where one class may correspond to a match exists between the medical reimbursement code and the surgical video, and the other class may correspond to no match exists between the medical reimbursement code and the surgical video.

In some aspects, the surgical video can be analyzed to detect a surgical tool, for example as described above. The determination of whether the match exists between the medical reimbursement code and the surgical video can be based on the detected surgical tool. For example, when a surgical tool of a particular type is detected, it may be determined that a match exists between the medical reimbursement code and the surgical video, and when no surgical tool of the particular type is detected, it may be determined that no match exists between the medical reimbursement code and the surgical video. In another example, when a surgical tool of a first type is detected, it may be determined that a match exists between the medical reimbursement code and the surgical video, and when a surgical tool of a second type is detected, it may be determined that no match exists between the medical reimbursement code and the surgical video.

In some aspects, the surgical video can be analyzed to detect an anatomical structure, for example as described above. Further, the surgical video can be analyzed to determine a condition of the anatomical structure. For example, a machine learning model may be trained using training examples to determine conditions of anatomical structure from surgical footage. An example of such training example may include a sample surgical video depicting a sample anatomical structure, together with a label indicating a condition of the sample anatomical structure. The condition of the anatomical structure can include, for example, whether the anatomical structure is healthy, whether there is sufficient blood flow, whether the size is proper, whether there is an infection, etc. The determination of whether the match exists between the medical reimbursement code and the surgical video can be based on the condition of the anatomical structure. For example, when the condition of the anatomical structure is a first condition, it may be determined that a match exists between the medical reimbursement code and the surgical video, and when the condition of the anatomical structure is a second condition, it may be determined that no match exists between the medical reimbursement code and the surgical video.

In some aspects, the surgical video can be analyzed to detect an interaction between a surgical tool and an anatomical structure of the patient, for example as described above. The determination of whether the match exists between the medical reimbursement code and the surgical video can be based on the detected interaction. For example, when an interaction between a particular surgical tool and a particular anatomical structure is detected, it may be determined that a match exists between the medical reimbursement code and the surgical video, and when an interaction between a particular surgical tool and a particular anatomical structure is not detected, it may be determined that no match exists between the medical reimbursement code and the surgical video. In such aspects, the surgical video may be analyzed to determine a specific characteristic of the interaction between the surgical tool and the anatomical structure, where the determination whether the match exists between the medical reimbursement code and the surgical video can be based on the characteristic. For example, the characteristic can be at least one of a duration of the interaction, a type of the interaction, or a state of the surgical tool during the interaction. In one example, the surgical video may be analyzed using a visual classification algorithm to classify the interaction to one of a plurality of alternative classes, and the characteristic may be determined based on the class. In another example, the surgical video may be analyzed using a visual regression algorithm to determine a numerical characteristic of the interaction.

The surgical video may be analyzed to detect an adverse event in the surgical procedure. For example, a machine learning model may be trained using training examples to detect adverse events in surgical footage. An example of such training example may include a sample surgical video, together with a label indicating whether an adverse event is depicted in the sample surgical video. The determination of whether the match exists between the medical reimbursement code and the surgical video can be based on the detected adverse event. For example, when an adverse event is detected, it may be determined that a match exists between the medical reimbursement code and the surgical video, and when no adverse event is detected, it may be determined that no match exists between the medical reimbursement code and the surgical video. In another example, when an adverse event of a first type is detected, it may be determined that a match exists between the medical reimbursement code and the surgical video, and when no adverse event of a second type is detected, it may be determined that no match exists between the medical reimbursement code and the surgical video.

In some aspects, a convolution of at least part of the surgical video can be calculated to obtain a result value. The determination of whether the match exists between the medical reimbursement code and the surgical video can be based on the result value. For example, when the result value is a first numerical value, it may be determined that a match exists between the medical reimbursement code and the surgical video, and when the result value is a second numerical value, it may be determined that no match exists between the medical reimbursement code and the surgical video.

A machine learning model can be used to analyze the surgical video. This analysis can determine whether the match exists between the medical reimbursement code and the surgical video. For example, the machine learning model may be a machine learning model trained using training examples to determine whether matches exists between medical reimbursement codes and surgical footage. An example of such training example may include a sample medical reimbursement code and a sample surgical video, together with a label indicating whether a match exists between the sample medical reimbursement code and the sample surgical video.

The surgical video may be analyzed to detect multiple surgical events in the surgical procedure, for example as described above. For example, a first surgical event and a second surgical event can be detected. Then, the determination of whether the match exists between the medical reimbursement code and the surgical video can be based on whether the first surgical event precedes the second surgical event in the surgical procedure. For example, when the first surgical event precedes the second surgical event, it may be determined that a match exists between the medical reimbursement code and the surgical video, and when the second surgical event precedes the first surgical event, it may be determined that no match exists between the medical reimbursement code and the surgical video.

In 1908, when the match described in 1906 is determined not to exist, an indicator of a lack of support in the surgical video for the medical reimbursement code is output. For example, the indicator may be stored in memory, may be transmitted to an external computing device (for example, using a digital communication device), may be presented to an individual (e.g., via a user interface, visually, audibly, textually, graphically, etc.), and so forth. In one example, the indicator may be provided to an insurer, to a medical coding auditor, to a medical coder, to an accounting department, and so forth.

In some aspects, the surgical video can be analyzed to classify a mismatch between the medical reimbursement code and the surgical video. For example, a machine learning model may be trained using training examples to classify mismatches between medical reimbursement codes and surgical videos. An example of such training example may include a sample medical reimbursement code and a sample surgical video, together with a label indicating a type of a mismatch between the sample medical reimbursement code and the sample surgical video. The trained machine learning model may be used to classify the mismatch between the medical reimbursement code and the surgical video, for example based on an analysis of the medical reimbursement code and the surgical video. Further, the indicator can be based on the classification of the mismatch. For example, the indicator may include an indication of a type of the mismatch. In another example, when the mismatch is classified to a first class, a first indicator may be output to indicate the lack of support in the surgical video for the medical reimbursement code, and when the mismatch is classified to a second class, a second indicator may be output to indicate the lack of support in the surgical video for the medical reimbursement code. The second indicator may differ from the first indicator. Some non-limiting examples of such types may include an undercoding mismatch, an overcoding mismatch, a complete mismatch, and so forth.

In some aspects, an alternative medical reimbursement code can be determined through an analysis of the surgical video. For example, the surgical video may be analyzed as described above in relation to 1700 to determine the alternative medical reimbursement code. In another example, the surgical video and/or the medical reimbursement code may be analyzed using a machine learning model to determine the alternative medical reimbursement code. In one example, the machine learning model may be a machine learning model trained using training examples to suggest alternative medical reimbursement codes based on surgical footage and/or original alternative medical reimbursement codes. An example of such training example may include a sample surgical video and/or a sample medical reimbursement code, together with a label indicating a sample alternative medical reimbursement code. Further, an indication of the alternative medical reimbursement code can be output. For example, the indicator of the alternative medical reimbursement code may be stored in memory, may be transmitted to an external computing device (for example, using a digital communication device), may be presented to an individual (e.g., via a user interface, visually, audibly, textually, graphically, etc.), and so forth. In one example, the indicator of the alternative medical reimbursement code may be provided to an insurer, to a medical coding auditor, to a medical coder, to an accounting department, and so forth.

Figure 20:
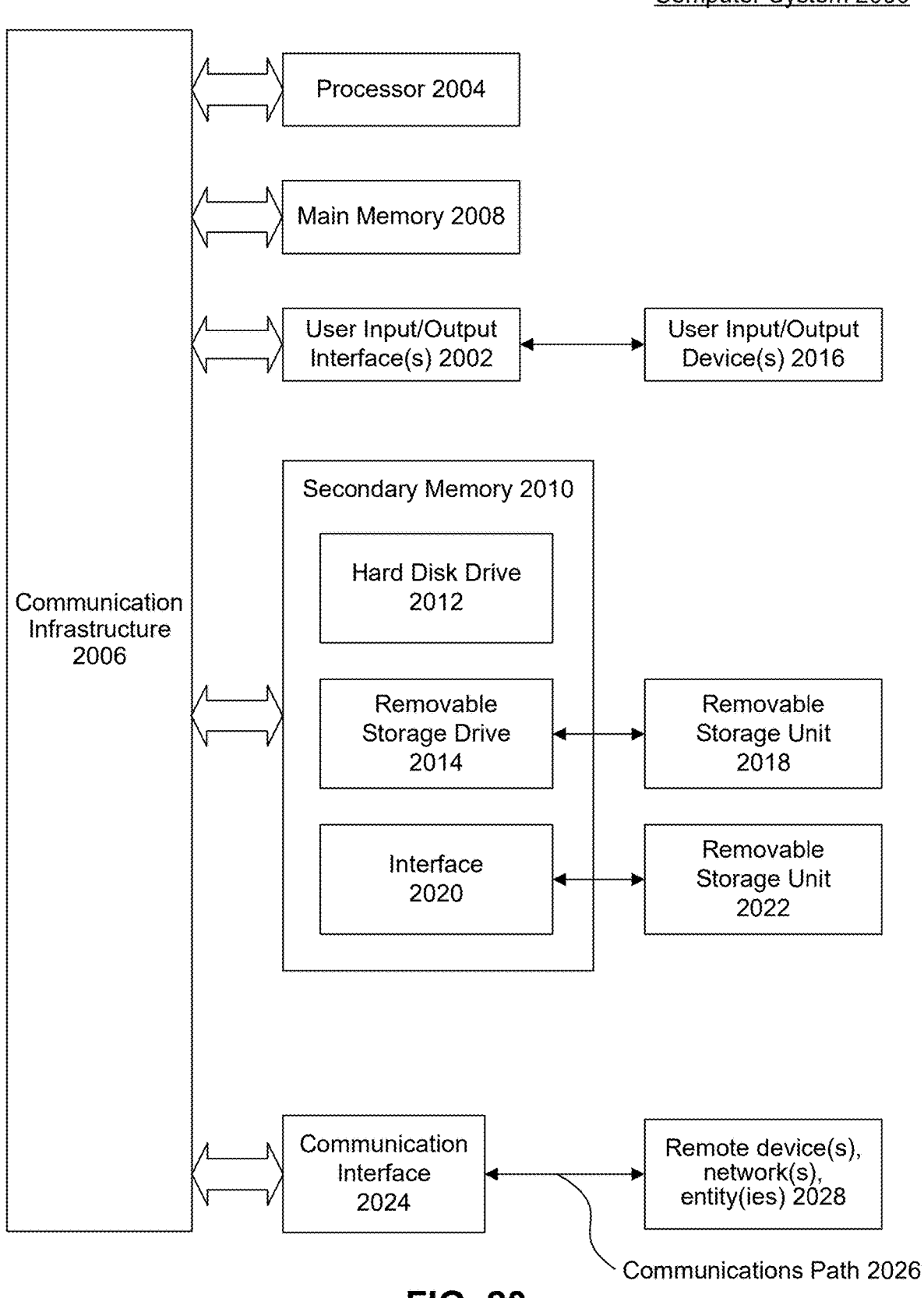
FIG. 20 is a block diagram of an example computer system useful for implementing various aspects.

Various aspects can be implemented, for example, using one or more computer systems, such as computer system 2000 shown in FIG. 20. Computer system 2000 can be used, for example, to implement a system for performing the processes described with reference to FIGS. 5, 9, 11, 12, 15, 17, and 19. For example, computer system 2000 can store and access various information (e.g., data structures, surgical guidelines, medical codes, etc.), can receive inputs (e.g., selections), can include an intracorporeal video footage repository, can conduct image analysis, can conduct compliance analysis, can conduct linguistic analysis, and can output indicators (e.g., notifications), actions, or information. Computer system 2000 can be any computer capable of performing the functions described herein.

Computer system 2000 can be any well-known computer capable of performing the functions described herein.

Computer system 2000 includes one or more processors (also called central processing units, or CPUs), such as a processor 2004. Processor 2004 is connected to a communication infrastructure or bus 2006.

One or more processors 2004 may each be a graphics processing unit (GPU). In an aspect, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 2000 also includes user input/output device(s) 2016, such as monitors, keyboards, pointing devices, etc., that communicate with communication infrastructure 2006 through user input/output interface(s) 2002.

Computer system 2000 also includes a main or primary memory 2008, such as random access memory (RAM). Main memory 2008 may include one or more levels of cache. Main memory 2008 has stored therein control logic (i.e., computer software) and/or data.

Computer system 2000 may also include one or more secondary storage devices or memory 2010. Secondary memory 2010 may include, for example, a hard disk drive 2012 and/or a removable storage device or drive 2014. Removable storage drive 2014 may be a floppy disk drive, a magnetic tape drive, a compact disk drive, an optical storage device, tape backup device, and/or any other storage device/drive.

Removable storage drive 2014 may interact with a removable storage unit 2018. Removable storage unit 2018 includes a computer usable or readable storage device having stored thereon computer software (control logic) and/or data. Removable storage unit 2018 may be a floppy disk, magnetic tape, compact disk, DVD, optical storage disk, and/any other computer data storage device. Removable storage drive 2014 reads from and/or writes to removable storage unit 2018 in a well-known manner.

According to an exemplary aspect, secondary memory 2010 may include other means, instrumentalities or other approaches for allowing computer programs and/or other instructions and/or data to be accessed by computer system 2000. Such means, instrumentalities or other approaches may include, for example, a removable storage unit 2022 and an interface 2020. Examples of the removable storage unit 2022 and the interface 2020 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 2000 may further include a communication or network interface 2024. Communication interface 2024 enables computer system 2000 to communicate and interact with any combination of remote devices, remote networks, remote entities, etc. (individually and collectively referenced by reference number 2028). For example, communication interface 2024 may allow computer system 2000 to communicate with remote devices 2028 over communications path 2026, which may be wired and/or wireless, and which may include any combination of LANs, WANs, the Internet, etc. Control logic and/or data may be transmitted to and from computer system 2000 via communication path 2026.

In an aspect, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 2000, main memory 2008, secondary memory 2010, and removable storage units 2018 and 2022, as well as tangible articles of manufacture embodying any combination of the foregoing. Such control logic, when executed by one or more data processing devices (such as computer system 2000), causes such data processing devices to operate as described herein.

Based on the teachings contained in this disclosure, it will be apparent to persons skilled in the relevant art(s) how to make and use aspects of this disclosure using data processing devices, computer systems and/or computer architectures other than that shown in FIG. 20. In particular, aspects can operate with software, hardware, and/or operating system implementations other than those described herein.

It is to be appreciated that the Detailed Description section, and not any other section, is intended to be used to interpret the claims. Other sections can set forth one or more but not all exemplary aspects as contemplated by the inventor(s), and thus, are not intended to limit this disclosure or the appended claims in any way.

While this disclosure describes exemplary aspects for exemplary fields and applications, it should be understood that the disclosure is not limited thereto. Other aspects and modifications thereto are possible, and are within the scope and spirit of this disclosure. For example, and without limiting the generality of this paragraph, aspects are not limited to the software, hardware, firmware, and/or entities illustrated in the figures and/or described herein. Further, aspects (whether or not explicitly described herein) have significant utility to fields and applications beyond the examples described herein.

Aspects have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative aspects can perform functional blocks, steps, operations, methods, etc. using orderings different than those described herein.

References herein to "one aspect," "an aspect," "an example aspect," or similar phrases, indicate that the aspect described can include a particular feature, structure, or characteristic, but every aspect can not necessarily include the particular feature, structure, or characteristic. Moreover, such phrases are not necessarily referring to the same aspect. Further, when a particular feature, structure, or characteristic is described in connection with an aspect, it would be within the knowledge of persons skilled in the relevant art(s) to incorporate such feature, structure, or characteristic into other aspects whether or not explicitly mentioned or described herein. Additionally, some aspects can be described using the expression "coupled" and "connected" along with their derivatives. These terms are not necessarily intended as synonyms for each other. For example, some aspects can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary aspects, but should be defined only in accordance with the following claims and their equivalents.

What is claimed is:

1. A non-transitory computer readable medium containing instructions that, when executed by at least one processor, cause the at least one processor to execute operations to perform intracorporeal video analysis operations for monitoring compliance with surgical guidelines, the operations comprising:

(a) presenting descriptors of a group of surgical guidelines;

(b) receiving a selection of a subgroup of surgical guidelines from the group of surgical guidelines, the subgroup of surgical guidelines including at least one but not all of the surgical guidelines from the group of surgical guidelines, the subgroup of surgical guidelines including a first video-associated medical guideline and a second non-video associated medical guideline;

(c) accessing a repository of intracorporeal video streams depicting performance, by at least one surgeon, of a plurality of surgical procedures governed by the subgroup of surgical guidelines;

(d) for each surgical procedure of the plurality of surgical procedures, performing image analysis on an intracorporeal video stream from the repository, the intracorporeal video stream capturing a respective surgical procedure, the image analysis being used to determine whether at least one surgical guideline was completed and to determine compliance with the first video-associated medical guideline, wherein the operations further comprise:

extracting a result value for a respective frame of the intracorporeal video stream by executing a convolution on pixel values of the respective frame, wherein the result value comprises at least a numerical value; and based on the numerical value, determining whether the at least one surgical guideline was completed for the first video-associated medical guideline in the respective frame;

(e) retrieving at least one record of at least one non-surgical action to support the respective surgical procedure; and (f) analyzing the at least one record to determine compliance with the second non-video associated medical guideline;

(g) based on the compliance with the first video-associated medical guideline from the image analysis and the compliance with the second non-video associated medical guideline, determining an aggregated compliance level indicative of compliance of the at least one surgeon with the subgroup of surgical guidelines; and (h) outputting an indicator of the aggregated compliance level.

2. The non-transitory computer readable medium of claim 1, wherein the presenting the descriptors comprises presenting a category for each surgical guideline.

3. The non-transitory computer readable medium of claim 1, wherein the presenting the descriptors comprises providing links to medical articles supporting the group of surgical guidelines.

4. The non-transitory computer readable medium of claim 1, wherein the presenting the descriptors comprises presenting a predicted effect to comply with each surgical guideline.

5. The non-transitory computer readable medium of claim 1, wherein the plurality of surgical procedures were performed over a period of time and the aggregated compliance level reflects an overall compliance of the subgroup of surgical guidelines over the period of time.

6. The non-transitory computer readable medium of claim 1, wherein the operations further comprise, when the aggregated compliance level is less than a threshold, presenting one or more recommendations to improve compliance of a specific surgical guideline from the subgroup of surgical guidelines.

7. The non-transitory computer readable medium of claim 1, wherein the at least one non-surgical action includes an action performed after the respective surgical procedure.

8. The non-transitory computer readable medium of claim 1, wherein the indicator includes a first indicator reflective of a compliance level to the first video-associated medical guideline and a second indicator reflective of a compliance level to the second non-video associated medical guideline.

9. The non-transitory computer readable medium of claim 1, wherein the operations further comprise:

performing image analysis on a particular intracorporeal video stream from the repository capturing a particular surgical procedure to detect a first set of intraoperative actions performed during the particular surgical procedure;

based on the first set of intraoperative actions, determining a series of video frames depicting a failure to comply with a particular surgical guideline during the particular surgical procedure;

selecting, from the repository, a specific reference video stream demonstrating adherence to the particular surgical guideline;

outputting the series of video frames depicting the failure to comply with the particular surgical guideline; and outputting the specific reference video stream demonstrating adherence to the particular surgical guideline.

10. The non-transitory computer readable medium of claim 9, wherein the operations further comprise presenting a user interface for display of the outputted series of video frames and the specific reference video stream.

11. The non-transitory computer readable medium of claim 10, wherein the user interface is configured to simultaneously present the outputted series of video frames and the specific reference video stream.

12. The non-transitory computer readable medium of claim 11, wherein the user interface is configured to present the outputted series of video frames and the specific reference video stream in an aligned timing sequence.

13. The non-transitory computer readable medium of claim 11, wherein the user interface is configured to modify at least one of the outputted series of video frames and the specific reference video stream to match one or more display parameters.

14. The non-transitory computer readable medium of claim 9, wherein the series of video frames includes at least one detected intraoperative action that took place prior to the failure to comply with the particular surgical guideline.

15. The non-transitory computer readable medium of claim 9, wherein the operations further comprise determining one or more characteristics of the particular surgical procedure, and wherein the selecting of the specific reference video stream is based on the one or more characteristics of the particular surgical procedure.

16. The non-transitory computer readable medium of claim 15, wherein the operations further comprise analyzing an additional intracorporeal video stream from the repository of intracorporeal video streams to identify other surgical procedures from the plurality of surgical procedures in which the particular surgical guideline was uncompiled with.

17. The non-transitory computer readable medium of claim 16, wherein the operations further comprise:

determining a likely reason for the failure to comply with the particular surgical guideline during the particular surgical procedure in view of the other surgical procedures, and outputting an indication of the likely reason.

18. The non-transitory computer readable medium of claim 1, wherein the performing the image analysis further comprises:

based on the numerical value, determining an action performed during the respective surgical procedure based on the numerical value; and based on the action performed during the respective surgical procedure, determining whether the at least one surgical guideline was completed for the first video-associated medical guideline in the respective frame based on the action performed during the respective surgical procedure.

19. A computer-implemented method for performing intracorporeal video analysis operations for monitoring compliance with surgical guidelines, comprising:

(a) presenting descriptors of a group of surgical guidelines;

(b) receiving a selection of a subgroup of surgical guidelines from the group of surgical guidelines, the subgroup of surgical guidelines including at least one but not all of the surgical guidelines from the group of surgical guidelines, the subgroup of surgical guidelines including a first video-associated medical guideline and a second non-video associated medical guideline;

(c) accessing a repository of intracorporeal video streams depicting performance, by at least one surgeon, of a plurality of surgical procedures governed by the subgroup of surgical guidelines;

(d) for each surgical procedure of the plurality of surgical procedures, performing image analysis on an intracorporeal video stream from the repository, the intracorporeal video stream capturing a respective surgical procedure, the image analysis being used to determine whether at least one surgical guideline was completed and to determine compliance with the first video-associated medical guideline, further comprising:

extracting a result value for a respective frame of the intracorporeal video stream by executing a convolution on pixel values of the respective frame, wherein the result value comprises at least a numerical value; and based on the numerical value, determining whether the at least one surgical guideline was completed for the first video-associated medical guideline in the respective frame;

(e) retrieving at least one record of at least one non-surgical action to support the respective surgical procedure; and (f) analyzing the at least one record to determine compliance with the second non-video associated medical guideline;

(g) based on the compliance with the first video-associated medical guideline from the image analysis and the compliance with the second non-video associated medical guideline, determining an aggregated compliance level indicative of compliance of the at least one surgeon with the subgroup of surgical guidelines; and (h) outputting an indicator of the aggregated compliance level.

20. A system for performing intracorporeal video analysis operations for monitoring compliance with surgical guidelines, the system comprising a processor configured to perform operations comprising:

(a) presenting descriptors of a group of surgical guidelines;

(b) receiving a selection of a subgroup of surgical guidelines from the group of surgical guidelines, the subgroup of surgical guidelines including at least one but not all of the surgical guidelines from the group of surgical guidelines, the subgroup of surgical guidelines including a first video-associated medical guideline and a second non-video associated medical guideline;

(c) accessing a repository of intracorporeal video streams depicting performance, by at least one surgeon, of a plurality of surgical procedures governed by the subgroup of surgical guidelines;

(d) for each surgical procedure of the plurality of surgical procedures, performing image analysis on an intracorporeal video stream from the repository, the intracorporeal video stream capturing a respective surgical procedure, the image analysis being used to determine whether at least one surgical guideline was completed and to determine compliance with the first video-associated medical guideline, wherein the operations further comprise:

extracting a result value for a respective frame of the intracorporeal video stream by executing a convolution on pixel values of the respective frame, wherein the result value comprises at least a numerical value; and based on the numerical value, determining whether the at least one surgical guideline was completed for the first video-associated medical guideline in the respective frame;

(e) retrieving at least one record of at least one non-surgical action to support the respective surgical procedure; and (f) analyzing the at least one record to determine compliance with the second non-video associated medical guideline;

(g) based on the compliance with the first video-associated medical guideline from the image analysis and the compliance with the second non-video associated medical guideline, determining an aggregated compliance level indicative of compliance of the at least one surgeon with the subgroup of surgical guidelines; and (h) outputting an indicator of the aggregated compliance level.

21. A non-transitory computer readable medium containing instructions that, when executed by at least one processor, cause the at least one processor to execute operations to perform intracorporeal video analysis operations for monitoring compliance with surgical guidelines, the operations comprising:

(a) presenting descriptors of a group of surgical guidelines;

(b) receiving a selection of a subgroup of surgical guidelines from the group of surgical guidelines, the subgroup of surgical guidelines including at least one but not all of the surgical guidelines from the group of surgical guidelines;

(c) accessing a repository of intracorporeal video streams depicting performance, by at least one surgeon, of a plurality of surgical procedures governed by the subgroup of surgical guidelines;

(d) for each surgical procedure of the plurality of surgical procedures, performing image analysis on an intracorporeal video stream from the repository, the intracorporeal video stream capturing a respective surgical procedure, the image analysis being used to determine whether the at least one surgical guideline was completed and to detect a first set of intraoperative actions performed during the surgical procedure, wherein the operations further comprise:

extracting a result value for a respective frame of the intracorporeal video stream by executing a convolution on pixel values of the respective frame, wherein the result value comprises at least a numerical value; and based on the numerical value, determining whether the at least one surgical guideline was completed in the respective frame;

(e) based on the image analysis, determining an aggregated compliance level indicative of compliance of the at least one surgeon with the subgroup of surgical guidelines;

(f) outputting an indicator of the aggregated compliance level;

(g) based on a detected first set of intraoperative actions, determining a series of video frames depicting a failure to comply with a particular surgical guideline during the respective surgical procedure;

(h) selecting, from the repository, a specific reference video stream demonstrating adherence to the particular surgical guideline;

(i) outputting the series of video frames depicting the failure to comply with the particular surgical guideline; and (j) outputting the specific reference video stream demonstrating adherence to the particular surgical guideline.

* * * * *